(12) United States Patent
Duke et al.

(10) Patent No.: US 7,790,434 B2
(45) Date of Patent: Sep. 7, 2010

(54) METHODS AND COMPOSITIONS FOR EXPRESSING NEGATIVE-SENSE VIRAL RNA IN CANINE CELLS

(75) Inventors: Gregory Duke, Redwood, CA (US); George Kemble, Saratoga, CA (US); James Young, Potomac, MD (US); Zhaoti Wang, Palo Alto, CA (US)

(73) Assignee: MedImmune, LLC, Gaithersburg, MD (US)

( * ) Notice: Subject to any disclaimer, the term of this patent is extended or adjusted under 35 U.S.C. 154(b) by 784 days.

(21) Appl. No.: 11/501,067

(22) Filed: Aug. 9, 2006

(65) Prior Publication Data

US 2007/0031941 A1    Feb. 8, 2007

Related U.S. Application Data

(63) Continuation-in-part of application No. 11/455,734, filed on Jun. 20, 2006.

(60) Provisional application No. 60/692,978, filed on Jun. 21, 2005, provisional application No. 60/699,555, filed on Jul. 15, 2005, provisional application No. 60/699,556, filed on Jul. 15, 2005, provisional application No. 60/702,006, filed on Jul. 22, 2005, provisional application No. 60/793,522, filed on Apr. 19, 2006, provisional application No. 60/793,525, filed on Apr. 19, 2006.

(51) Int. Cl.
C12N 7/00 (2006.01)
A61K 39/145 (2006.01)

(52) U.S. Cl. ................... 435/235.1; 424/206.1

(58) Field of Classification Search ........... None
See application file for complete search history.

(56) References Cited

U.S. PATENT DOCUMENTS

| | | | |
|---|---|---|---|
| 5,690,937 | A | 11/1997 | Parkin et al. |
| 5,789,229 | A | 8/1998 | Wertz et al. |
| 5,824,536 | A | 10/1998 | Webster et al. |
| 6,001,634 | A * | 12/1999 | Palese et al. ............. 435/235.1 |
| 6,146,642 | A | 11/2000 | Garcia-Sastre et al. |
| 6,649,372 | B1 | 11/2003 | Palese et al. |
| 6,887,699 | B1 | 5/2005 | Palese et al. |
| 6,951,754 | B2 | 10/2005 | Hoffmann |
| 2004/0002061 | A1 | 1/2004 | Kawaoka |
| 2004/0241139 | A1 | 12/2004 | Hobom et al. |
| 2004/0265987 | A1 | 12/2004 | Trager et al. |
| 2005/0003349 | A1 | 1/2005 | Kawaoka |
| 2005/0037487 | A1 | 2/2005 | Kawaoka |
| 2005/0158342 | A1 | 7/2005 | Kemble |
| 2005/0221489 | A1 | 10/2005 | Garcia-Sastre et al. |
| 2005/0266026 | A1 | 12/2005 | Hoffmann et al. |

FOREIGN PATENT DOCUMENTS

| | | |
|---|---|---|
| EP | 0702085 A1 | 3/1996 |
| EP | 780475 B1 | 6/1997 |
| WO | WO-96-15232 | 5/1996 |
| WO | WO-96-34625 | 11/1996 |
| WO | WO-97-12032 | 4/1997 |
| WO | WO-98-02530 | 1/1998 |
| WO | WO-98-13501 | 4/1998 |
| WO | WO-98-53078 | 11/1998 |
| WO | WO-99-02657 | 1/1999 |
| WO | WO-01-04333 | 1/2001 |
| WO | WO 0104333 A1 * | 1/2001 |
| WO | WO-01-83794 | 11/2001 |
| WO | WO-2004-112831 | 12/2004 |
| WO | WO-2006-067211 | 6/2006 |
| WO | WO-2007-002008 | 1/2007 |
| WO | WO-2007-002008 A3 | 1/2007 |
| WO | WO-2007-124327 | 11/2007 |

OTHER PUBLICATIONS

Garcia-Sastre et al. (Virology, 1998, vol. 252, pp. 324-330).*
Hatta et al. Science, 2001, vol. 293, pp. 1840-1842.*
de Wit, E., et al. "A Reverse-Genetics System for Influenza A Virus using T7 RNA Polymerase." *J.Gen.Virol.* (2007) 88: 1281-7.
de Wit, E., et al. "Efficient Generation and Growth of Influenza Virus A/PR/8/34 from Eight cDNA Fragments." *Virus Res.* (2004) 103: 155-61.
Dos Santos Afonso, E., et al. "The Generation of Recombinant Influenza A Viruses Expressing a PB2 Fusion Protein Requires the Conservation of a Packaging Signal Overlapping the Coding and Noncoding Regions at the 5' End of the PB2 Segment." *Virology* 341.1 (2005): 34-46.
Fodor, E., et al. "Rescue of Influenza A Virus from Recombinant DNA." *J.Virol.* (1999) 73: 9679-82.
Fodor, E., et al. "Attenuation of Influenza A Virus mRNA Levels by Promoter Mutations." *J.Virol.* (1998) 72: 6283-90.
Furminger, I. "Vaccine Production." *Textbook of Influenza.* Nicholson, R.G. et al. Ed., Chapter 24, pp. 324-332, Blackwell, Oxford, UK, 1998.
Grummt, I. "Life on a Planet of its Own: Regulation of RNA Polymerase I Transcription in the Nucleolus." *Genes Dev.* (2003) 17: 1691-702.
Hatta, M., et al. "Molecular Basis for High Virulence of Hong Kong H5N1 Influenza A Viruses." *Science* (New York, N.Y.) 293.5536 (2001): 1840-2.
Heix, J., et al. "Species Specificity of Transcription by RNA Polymerase I." *Curr.Opin.Genet.Dev.* (1995) 5: 652-6.
Hoffmann, E., et al. "Eight-Plasmid System for Rapid Generation of Influenza Virus Vaccines." *Vaccine* (2002) 20: 3165-70.
Hoffmann, E., et al. "Rescue of Influenza B Virus from Eight Plasmids." *Proc.Natl.Acad.Sci.U.S.A.* (2002) 99: 11411-6.
Hoffmann, E., et al. ""Ambisense" Approach for the Generation of Influenza A Virus: VRNA and mRNA Synthesis from One Template." *Virology* (2000) 267: 310-7.
Hoffmann, E., et al. "A DNA Transfection System for Generation of Influenza A Virus from Eight Plasmids." *Proc.Natl.Acad.Sci.U.S.A.* (2000) 97: 6108-13.

(Continued)

*Primary Examiner*—Stacy B Chen

(57) ABSTRACT

The present invention provides novel canine pol I regulatory nucleic acid sequences useful for the expression of nucleic acid sequences in canine cells such as MDCK cells. The invention further provides expression vectors and cells comprising such nucleic acids as well as methods of using such nucleic acids to make influenza viruses, including infectious influenza viruses.

11 Claims, 20 Drawing Sheets

OTHER PUBLICATIONS

Figure 1:
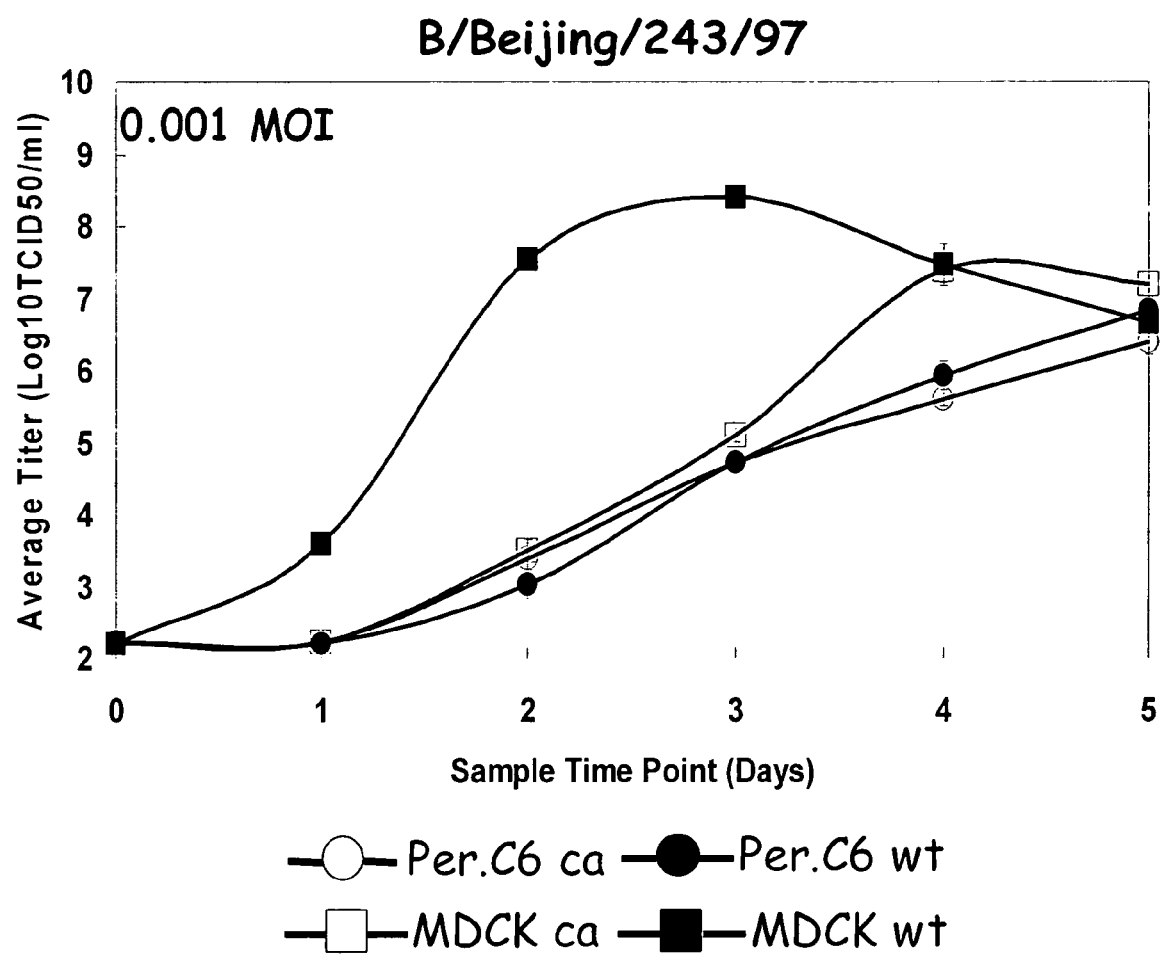

Hoffmann, E., et al. "Unidirectional RNA Polymerase I-Polymerase II Transcription System for the Generation of Influenza A Virus from Eight Plasmids." *J.Gen.Virol.* (2000) 81: 2843-7.

Hwang, J. S., et al. "Expression of Functional Influenza Virus RNA Polymerase in the Methylotrophic Yeast *Pichia pastoris.*" *J.Virol.* (2000) 74: 4074-84.

Massin, P., et al. "Cloning of the Chicken RNA Polymerase I Promoter and use for Reverse Genetics of Influenza A Viruses in Avian Cells." *J.Virol.* (2005) 79: 13811-6.

MedImmune Vaccines, Inc. "Written Opinion of the International Searching Authority for PCT/US2006/23867." : 1-4.

MedImmune Vaccines, Inc. "International Search Report and Written Opinion of the International Searching Authority for PCT/US2007/66895." : 1-10.

Merten, O. W., et al. "Production of Influenza Virus in Cell Cultures for Vaccine Preparation." *Adv.Exp.Med.Biol.* (1996) 397: 141-51.

Murakami, S., et al. "Establishment of Canine RNA Polymerase I-Driven Reverse Genetics for Influenza A Virus: Its Application for H5N1 Vaccine Production." *J.Virol.* (2008) 82: 1605-9.

Neumann, G., et al. "A Decade After the Generation of a Negative-Sense RNA Virus from Cloned cDNA—what have we Learned?" *J.Gen.Virol.* (2002) 83: 2635-62.

Neumann, G., et al. "Generation of Influenza a Viruses Entirely from Cloned cDNAs." *Proc.Natl.Acad.Sci.U.S.A.* (1999) 96: 9345-50.

Neumann, G., et al. "RNA Polymerase I-Mediated Expression of Influenza Viral RNA Molecules." *Virology* (1994) 202: 477-9.

Pleschka, S., et al. "A Plasmid-Based Reverse Genetics System for Influenza A Virus." *J.Virol.* (1996) 70: 4188-92.

Skinner, J. A., et al. "In Vitro Mutagenesis and Transcriptional Analysis of a Mouse Ribosomal Promoter Element." *Proc.Natl.Acad.Sci. U.S.A.* (1984) 81: 2137-41.

Spaete, R. R., et al. "The Alpha Sequence of the Cytomegalovirus Genome Functions as a cleavage/packaging Signal for Herpes Simplex Virus Defective Genomes." J.Virol. (1985) 54: 817-24.

Wang, Z., et al. "Cloning of the Canine RNA Polymerase I Promoter and Establishment of Reverse Genetics for Influenza A and B in MDCK Cells." *Virol.J.* (2007) 4: 102.

GenBank. "Accession No. CE554579, "Tigr-Gss-Dog-17000312351621 Dog Library Canis Familiaris Genomic, Genomic Survey Sequence." (Oct. 24, 2003) [Online] Retrieved from EBI."

GenBank. "Accession No. CE739435, "Tigr-Gss-Dog-17000315815994 Dog Library Canis Familiaris Genomic, Genomic Survey Sequence." (Oct. 4, 2003) [Online] Retrieved from EBI."

GenBank. "Accession No. CE553253, "Tigr-Gss-Dog-17000327447667 Dog Library Canis Familiaris Genomic, Genomic Survey Sequence." (Oct. 24, 2003) [Online] Retrieved from EBI."

GenBank. "Accession No. CE000081. "Tigr-Gss-Dog-17000320673734 Dog Library Canis Familiaris Genomic, Genomic Survey Sequence." (Sep. 25, 2003) [Online] Retrieved from EBI."

Makinen, A., et al. "Localization of 18S+28S and 5S Ribosomal RNA Genes in the Dog by Fluorescence in Situ Hybridization." Cytogenet.Cell Genet. (1997) 78: 231-5.

MedImmune Vaccines, Inc. "Extended European Search Report for PCT/US2006/023867." : 1-9.

Office Action for Co-pending U.S. Appl. No. 11/455,734, filed Jun. 20, 2006, mail date of Dec. 14, 2008.

Grummt, I. "Life on a Planet of its Own: Regulation of RNA Polymerase I Transcription in the Nucleolus." Genes & development 17.14 (2003): 1691-702.

Kirkness, E. F., et al. "The Dog Genome: Survey Sequencing and Comparative Analysis." Science (New York, N.Y.) 301.5641 (2003): 1898-903.

MedImmune Vaccines, Inc. "Extended European Search Report for PCT/US2007/7066895." : 1-8.

Wang, Z., and G. M. Duke. Abstract and Poster: "Cloning of the Canine RNA Polymerase I Promoter and Establishment of Reverse Genetics for Influenza A and B in MDCK Cells." 27th Annual Meeting of the Americal Society for Virology (ASV). Ithaca, New York, USA, Jul. 12-16, 2008.

\* cited by examiner

Replication of ca A/Vietnam/1203/2004 (H5N1) in MDCK cells

Fig. 5

Fig. 7

(SEQ ID NO:1)

```
aattctggag aaacagattg tgttataaga aagaaagaaa gaaagaaaga aagaaagaaa     60
gagaaaatcc ttatgttctt tgagcctccc ctcccccca gaattgagtt cctcttccac    120
gacctcttct cattcaaccc aatagacaag tatttggggg gggggtcag gtcccagacg    180
ctgagagggt ggaggtgaag gtggtgcggg gggggggggg cacaccgtcc tctccagcgc    240
ctttggttca gacctcttc gtgacctccc tccctccctc cctccctcct ccctcctcct    300
cctcctccct cttcgtctta taaatatata aataaaatcc taaagaaaag aaaaagaaaa    360
aaaaaaaaag gaaggacacg agaaaaaacg gtgcatccgt tgccgtcctg agagtcctcg    420
cctggtttcg gctctacgtt ccctccctga cctcggaaac gtgcctgagt cgtcccggga    480
gccccgcgcg gcgagcgcga ggctccccg gcggcagcg ggcccggacg gacggacgga    540
cggacggacg ggttttccaa ggctccccg ccccggga cggggttc gcggtgcgcg    600
gccgtgtgct ccgggccct ccgccgtccc cgggccgaga ggcgagatcc gaggcgcctg    660
acggcctcgc cgccggatc tgtcccgctg tcgttcgcgc cggttgtcgg gtgccactgg    720
cggccgcttt tatagagcgt gtccctccgg aggctccggg gcgacaggca aggaacagct    780
ttggtgtcgg tttcccgggg ccgagttcca ggaggagggc ggctccggcg cgagcgtctg    840
tcgcggggc ctcggcgcga tgcgctcgcc ggagattgga ctccggagct gcgagggagt    900
gtcgcgtcg cccgtgtcgc ccgtgtccgc tccgctcgc tcccggagga ggccgtgcgg    960
gccgcctggg tgggtcgacc agcaccgccg gtgcctctc ctcgcccgcg cggaccgacc   1020
tgggcgcctc gggggcgggg gacagggtgt gtcccgccgt ccgtcctgtg gctccgggcg   1080
atcttcgggc cttccttccg tgtcactcgg ttgtctcccg tggtcacgcc ctggcgacgg   1140
ggaccggtct gagcctggag gggaagcccg tgggtggcgc gacagacccg gctgcgggca   1200
```

Fig. 9A (SEQ ID NO:1 continued)

```
cgtgtggggg tccgggcgt cggacgcgat tttctcccct ttttccgagg cccgctgcgg 1260
aggtgggtcc cgggcggtcg gaccgggtgc cacgcggggg tgggcgggcc gtccgttcgg 1320
gcgtccggcc ccgtggcga ttcccggtga ggctgcctct gccgcgcgtg gccctccacc 1380
tcccctggcc cgagccgggg ttggggacgg cgtaggcac gggcggtcc tgagggccgc 1440
ggggacggc ctccgcacgg tgcctgcctc cggagaactt tgatgatttt tcaaagtctc 1500
ctcccgaga tcactgctt ggcggcgtgg cgcgtgtgcg cgcgtggcgg gtggcggcgt 1560
ggcggcgtgg cgtctccacc gaccgcgtat cgccccctcct ccccctcccc cccccccccg 1620
ttccctgggt cgaccagata gccctggggg ctccgtgggg gaggtcgcg gtgacctgtg 1680
ggggcaggtt ttggggacag ttggccgtgt cacggtcccg gaggtcgcg gtgacctgtg 1740
gctggtcccc gccggcaggc gcggttattt tcttgcccga gatgaacatt ttttgttgcc 1800
aggtaggtgc tgacacgttg tgtttcggcg acaggcagag agacgacagg cagacgtaaa 1860
agacagccgg accgtccgtc gctcgcgccg cagatgtggg cctctgggcg cgggtggggt 1920
tccgggcttg ctgcgcgccg cgagccggtc cctctccgtg gtggccggg cctgagccgt 1980
ccgcctgggc ctccggcacc cgaggagggg cgtgtgggc agtgtgcggt gggtcttta 2040
gccctccggt ctccatgccg tgggcaccg gccgttggcc gtgacaaccc ctgtctcgca 2160
ccccgtgcg ccgcgtgtca ggcgtcccc gctgtgtctg gggttgtccg gtcgctcctg 2220
aggctccgtg ccgggggtc gaggggcttg ccggtgaggc ggaagcaggt cccccggtc 2280
cccccccccc ctgggctttt gctgctctcc cgggccgggg aagcccctc gggccgcag cttgctgccg 2340
gcgtcctcg ctggctttt gctgctctcc cgtgctctcc tgggccgggc ctaagccgcg tcagacgagg 2400
atcgatcgat gtggtgatct cgtgctctcc ttctcgttct gcccgcgggc ccctccctcc 2460
gacgggcgtc cacgggcgat gcgaccgctc ttctcgttct gcccgcgggc ccctccctcc 2460
```

Fig. 9B (SEQ ID NO:1 continued)

| | | | | | | |
|---|---|---|---|---|---|---|
| ccggctcctc | cgcgcccggc | cgtcgtggcg | ggtgcgcggg | gggcgcgcgc | cggggtttggg | 2520 |
| ggtggtgcgg | actccggccc | gaccccggcc | tcccgccttc | ttgcctcgcg | gcgctggcgg | 2580 |
| gaccgggtc | ctcgacgcg | gcggacactc | tcgccggcct | ttcccgaagg | ccctggtcc | 2640 |
| gtggcgagcg | gccctcccct | cctccgcggg | ggagggccgg | cccgacgccg | cgctgctcac | 2700 |
| cgcccggcct | gggcgcgctt | gagcgcgttg | cgcccggccc | tccgtggtgc | ccctggagcg | 2760 |
| ctccaggtcg | cctcaggtgc | ctgaggccga | gcggtggcgt | cgtttccttc | cccggcgact | 2820 |
| cccctcgggc | tgccgccgcc | gtcgtcggcg | tgtccgagga | gcgggtggtg | gaagaagtcg | 2880 |
| gcaagggagg | cgcaccccgtg | cccctggcgg | gggcgcgggc | gcctcgtctt | ccttccctc | 2940 |
| tcctctcctc | cccctcgcg | cccctcgcg | gggtgggtgg | cgtggggcgg | tgtgactcgg | 3000 |
| aggacttggc | gggctcgtg | aggccgcggc | gggccggcc | acgccggc | gcttgccagc | 3060 |
| cgaggggctg | cccctctctc | cggcacgggt | cgtgtccccg | tctccgtccc | tctctctcgc | 3120 |
| gctcgcggga | ggcggggagc | tctctcctct | gggcggtgac | gtgaccacgc | cgtgcgcggg | 3180 |
| cgaggcgggg | gtggcgtcct | cgaggggca | ccggccgcga | gcgctcgggg | ttgccctgtg | 3240 |
| cctgtccctt | gccggagatc | cgcgcccccgc | cccgcgagcc | tgtcggcccc | ggagcgccgc | 3300 |
| ctggtggggc | ccgtttggga | ggacgaacgg | gtggggcgat | gcgccctcgg | tgagaaagcc | 3360 |
| ttctctagcg | atccgagagg | gtgccttggg | gtaccggagc | cccagccgc | tgccctcct | 3420 |
| ctgcgcgtgt | agtgtggcca | gcgacgcggg | gttggactcc | cgtcgcgacg | tgtttgggca | 3480 |
| gagtgccgct | ctttgcctac | ctacccgcgc | cctccgagac | ggggag | | 3537 |

Fig. 9C pAD4000 vector
(SEQ ID NO:29)

```
   1    ACCTA CCTGG CAACA AAAAA TGTTC ATCTC GGGCA AGAAA ATAAC CGCGC
  51    CTGCC GGCGG GGACC AGCCA CAGGT CACCG CGACC TCCCG GGACC GTGAC
 101    ACGGC CAACT GTCCC CAAAA CCTGC CCCAC GGCGC CCCCC CACCC CCACC
 151    CCACG GAGCC CCCAG GGCTA TCTGG TCGAC CCAGG GAACG GGGGG GGGGG
 201    GGGAG GGGAG GAGGG GCGAT ACGCG GTCGG TGGAG ACGCC ACGCC GCCAC
 251    GCCGC CACGC CGCCA CGCCG CCACG CCGCC ACGCC GCCAA GCCAG TGATC
 301    TCCGG GAGGA GACTT TGAAA AATCA TCAAA GTTCT CCGGA GGCAG GCACC
 351    GTGCG GAGGC CGTCC CCCGC GGCCC TCAGG ACCGC CCCGT GCCTA CCGCC
 401    GTCCC CAACC CCGGC TCGGG CCAGG GGAGG TGGAG GGCCA CGCGC GGCAG
 451    AGGCA GCCTC ACCGG GAATA TCGGG CCCGT CACCT CAGAC ATGAT AAGAT
 501    ACATT GATGA GTTTG GACAA ACCAC AACTA GAATG CAGTG AAAAA AATGC
 551    TTTAT TTGTG AAATT TGTGA TGCTA TTGCT TTATT TGTAA CCATT ATAAG
 601    CTGCA ATAAA CAAGG ATCTG CATTA ATGAA TCGGC CAACG CGCGG GGAGA
 651    GGCGG TTTGC GTATT GGGCG CTCTT CCGCT TCCTC GCTCA CTGAC TCGCT
 701    GCGCT CGGTC GTTCG GCTGC GGCGA GCGGT ATCAG CTCAC TCAAA GGCGG
 751    TAATA CGGTT ATCCA CAGAA TCAGG GGATA ACGCA GGAAA GAACA TGTGA
 801    GCAAA AGGCC AGCAA AAGGC CAGGA ACCGT AAAAA GGCCG CGTTG CTGGC
 851    GTTTT TCCAT AGGCT CCGCC CCCCT GACGA GCATC ACAAA AATCG ACGCT
 901    CAAGT CAGAG GTGGC GAAAC CCGAC AGGAC TATAA AGATA CCAGG CGTTT
 951    CCCCC TGGAA GCTCC CTCGT GCGCT CTCCT GTTCC GACCC TGCCG CTTAC
1001    CGGAT ACCTG TCCGC CTTTC TCCCT TCGGG AAGCG TGGCG CTTTC TCAAT
1051    GCTCA CGCTG TAGGT ATCTC AGTTC GGTGT AGGTC GTTCG CTCCA AGCTG
1101    GGCTG TGTGC ACGAA CCCCC CGTTC AGCCC GACCG CTGCG CCTTA TCCGG
1151    TAACT ATCGT CTTGA GTCCA ACCCG GTAAG ACACG ACTTA TCGCC ACTGG
1201    CAGCA GCCAC TGGTA ACAGG ATTAG CAGAG CGAGG TATGT AGGCG GTGCT
1251    ACAGA GTTCT TGAAG TGGTG GCCTA ACTAC GGCTA CACTA GAAGG ACAGT
1301    ATTTG GTATC TGCGC TCTGC TGAAG CCAGT TACCT TCGGA AAAAG AGTTG
1351    GTAGC TCTTG ATCCG GCAAA CAAAC CACCG CTGGT AGCGG TGGTT TTTTT
1401    GTTTG CAAGC AGCAG ATTAC GCGCA GAAAA AAAGG ATCTC AAGAA GATCC
1451    TTTGA TCTTT TCTAC GGGGT CTGAC GCTCA GTGGA ACGAA AACTC ACGTT
1501    AAGGG ATTTT GGTCA TGAGA TTATC AAAAA GGATC TTCAC CTAGA TCCTT
1551    TTAAA TTAAA AATGA AGTTT TAAAT CAATC TAAAG TATAT ATGAG TAAAC
1601    TTGGT CTGAC AGTTA CCAAT GCTTA ATCAG TGAGG CACCT ATCTC AGCGA
1651    TCTGT CTATT TCGTT CATCC ATAGT TGCCT GACTC CCCGT CGTGT AGATA
1701    ACTAC GATAC GGGAG GGCTT ACCAT CTGGC CCCAG TGCTG CAATG ATACC
1751    GCGAG ACCCA CGCTC ACCGG CTCCA GATTT ATCAG CAATA AACCA GCCAG
1801    CCGGA AGGGC CGAGC GCAGA AGTGG TCCTG CAACT TTATC CGCCT CCATC
1851    CAGTC TATTA ATTGT TGCCG GGAAG CTAGA GTAAG TAGTT CGCCA GTTAA
1901    TAGTT TGCGC AACGT TGTTG CCATT GCTAC AGGCA TCGTG GTGTC ACGCT
1951    CGTCG TTTGG TATGG CTTCA TTCAG CTCCG GTTCC CAACG ATCAA GGCGA
2001    GTTAC ATGAT CCCCC ATGTT GTGCA AAAAA GCGGT TAGCT CCTTC GGTCC
2051    TCCGA TCGTT GTCAG AAGTA AGTTG GCCGC AGTGT TATCA CTCAT GGTTA
2101    TGGCA GCACT GCATA ATTCT CTTAC TGTCA TGCCA TCCGT AAGAT GCTTT
2151    TCTGT GACTG GTGAG TACTC AACCA AGTCA TTCTG AGAAT AGTGT ATGCG
2201    GCGAC CGAGT TGCTC TTGCC CGGCG TCAAT ACGGG ATAAT ACCGC GCCAC
```

Fig. 13A

2251 ATAGC AGAAC TTTAA AAGTG CTCAT CATTG GAAAA CGTTC TTCGG GGCGA
2301 AAACT CTCAA GGATC TTACC GCTGT TGAGA TCCAG TTCGA TGTAA CCCAC
2351 TCGTG CACCC AACTG ATCTT CAGCA TCTTT TACTT TCACC AGCGT TTCTG
2401 GGTGA GCAAA AACAG GAAGG CAAAA TGCCG CAAAA AAGGG AATAA GGGCG
2451 ACACG GAAAT GTTGA ATACT CATAC TCTTC CTTTT TCAAT ATTAT TGAAG
2501 CATTT ATCAG GGTTA TTGTC TCATG AGCGG ATACA TATTT GAATG TATTT
2551 AGAAA AATAA ACAAA TAGGG GTTCC GCGCA CATTT CCCCG AAAAG TGCCA
2601 CCTGA CGTCG ATATG CCAAG TACGC CCCCT ATTGA CGTCA ATGAC GGTAA
2651 ATGGC CCGCC TGGCA TTATG CCCAG TACAT GACCT TATGG GACTT TCCTA
2701 CTTGG CAGTA CATCT ACGTA TTAGT CATCG CTATT ACCAT GGTGA TGCGG
2751 TTTTG CAGT ACATC AATGG GCGTG GATAG CGGTT TGACT CACGG GGATT
2801 TCCAA GTCTC CACCC CATTG ACGTC AATGG GAGTT TGTTT TGGCA CCAAA
2851 ATCAA CGGGA CTTTC CAAAA TGTCG TAACA ACTCC GCCCC ATTGA CGCAA
2901 ATGGG CGGTA GGCGT GTACG GTGGG AGGTC TATAT AAGCA GAGCT CTCTG
2951 GCTAA CTAGA GAACC CACTG CTTAC TGGCT TATCG AAATT AATAC GACTC
3001 ACTAT AGGGA GACCC AAGCT GTTAA CGCTA GCTAG CAGTT AACCG GAGTA
3051 CTGGT CGACC TCCGA AGTTG GGGGG GAGAG TCTTC TCGAG TAGAA GACCG
3101

Fig. 13B

BPB1.as4
BPB1.2.1
BPB1.as5
BPB1.1

MDV-B PB1

2369 bp

BNS.1                                             BNS.as1.1

MDV-B NS 1098 bp

Fig. 14

| Primer | Sequence | Position | |
|---|---|---|---|
| BPB1.1 | GGCACTAATGGTCACAACTG | 357-346 | (SEQ ID NO: 34) |
| BPB1.2.1 | ATCAGAGGGTTTGTATTAGTAG | 763-784 | (SEQ ID NO: 35) |
| BPB1.as4 | TGGGCTGTCTCTGGTTATTC | 992-1011 | (SEQ ID NO: 36) |
| BPB1.as5 | TCTCTTTATGAGGAAACCCT | 611-630 | (SEQ ID NO: 37) |

| Primer | Sequence | Position | |
|---|---|---|---|
| BNS.1 | GTGAGCCTGAAAGTAAAAGG | 238-257 | (SEQ ID NO: 38) |
| BNS.as1.1 | GCAACAAGTTTAGCAACAAG | 696-715 | (SEQ ID NO: 39) |

Fig. 15

```
360                                                                          429
MDV-B NS   (SEQ ID NO:32)
AAAAATTCCTCAAATAGCAACTGTCCAAACTGCAATTGGACCGATTACCCTCCAACACCAGGAAAGTGCC

Rescued MDV-B NS with silent mutations (SEQ ID NO:33)
AAAAATTCCTCAAATAGCAACTGTCCAAACTGCAATTGGACCGATTACCCTCCAACGCCAGGAAAGTGCC 430                                        478
MDV-B NS
TTGATGACATAGAAGAAGAACCGGAGAATGTTGATGACCCAACTGAAAT Rescued MDV-B NS with silent mutations
TTGATGACATAGAAGAAGAACCGGAGAATGTTGATGACCCAACTGAAAT
```

Fig. 16A 530                                                                        599
MDV-B PB1   (SEQ ID NO:40)
TCATTGATTCATTGGACAAACCTGAAATGACTTTCTTCTCGGTAAAGAATATAAAGAAAAAATTGCCTGC

Rescued MDV-B PB1 with silent mutations (SEQ ID NO:41)
TCATTGATTCATTGGACAAACCTGAAATGACCTTCTTCTCGGTAAAGAATATAAAGAAAAAATTGCCTGC 600                                                                        669
MDV-B PB1
TAAAAACAGAAAGGGTTTCCTCATAAAGAGAATACCAATGAAGGTAAAAGACAGAATAACCAGAGTGGAA Rescued MDV-B PB1 with silent mutations
TAAAAACAGAAAGGGTTTCCTCATAAAGAGAATACCAATGAAGGTAAAAGACAGAATAACCAGAGTGGAA 670                                                                        739
MDV-B PB1
TACATCAAAAGAGCATTATCATTAAACACAATGACAAAAGATGCTGAAAGAGGCAAACTAAAAAGAAGAG Rescued MDV-B PB1 with silent mutations
TACATCAAAAGAGCATTATCATTAAACACAATGACAAAAGATGCTGAAAGAGGCAAACTAAAAAGAAGAG 740                                                                        809
MDV-B PB1
CAATTGCCACCGCTGGGATACAAATCAGAGGGTTTGTATTAGTAGTTGAAAACTTGGCTAAAAATATCTG Rescued MDV-B PB1 with silent mutations
CAATTGCCACCGCTGGGATACAAATCAGAGGGTTTGTATTAGTAGTTGAAAACTTGGCTAAAAATATCTG 810                                                                        879
MDV-B PB1
TGAAAATCTAGAACAAAGTGGTTTGCCAGTAGGTGGGAACGAGAAGAAGGCCAAACTGTCAAATGCAGTG Rescued MDV-B PB1 with silent mutations
TGAAAATCTAGAACAAAGTGGTTTGCCAGTAGGTGGGAACGAGAAGAAGGCCAAACTGTCAAATGCAGTG 880                                                                        949
MDV-B PB1
GCCAAAATGCTCAGTAACTGCCCACCAGGAGGGATCAGCATGACAGTGACAGGAGACAATACTAAATGGA Rescued MDV-B PB1 with silent mutations
GCCAAAATGCTCAGTAACTGCCCACCAGGAGGGATCAGCATGACGGTGACAGGAGACAATACTAAATGGA

950
MDV-B PB1
ATG

Rescued MDV-B PB1 with silent mutations
ATG

Fig. 16B

SEQUENCE LISTING

<160> NUMBER OF SEQ ID NOS: 41

<210> SEQ ID NO 1
<211> LENGTH: 3537

<212> TYPE: DNA
<213> ORGANISM: Canis familiaris

<400> SEQUENCE: 1

```
aattctggag aaacagattg tgttataaga agaaagaaa gaaagaaaga aagaaagaaa      60
gagaaaatcc ttatgttctt tgagcctccc ctccccccca gaattgagtt cctcttccac    120
gacctcttct cattcaaccc aatagacaag tatttggggg gggggtcag gtcccagacg    180
ctgagagggt ggaggtgaag gtggtgcggg ggggggggg cacaccgtcc tctccagcgc    240
ctttggttca gacctccttc gtgacctccc tccctccctc cctccctcct cctcctcct    300
cctcctccct cttcgtctta taatatata aataaaatcc taaagaaaag aaaagaaaa    360
aaaaaaaag gaaggacacg agaaaaaacg gtgcatccgt tgccgtcctg agagtcctcg    420
cctggtttcg gctctacgtt ccctccctga cctcggaaac gtgcctgagt cgtcccggga    480
gccccgcgcg gcgagcgcga ccccctttcg ggcggcagcg ggcccggacg gacgacgga    540
cggacggacg ggttttccaa ggctccccg ccccgggagg acggggttc gcggtgcgcg    600
gccgtgtgct ccggggccct ccgccgtccc cgggccgaga ggcgagatcc gaggcgcctg    660
acggcctcgc cgcccggatc tgtcccgctg tcgttcgcgc cggttgtcgg gtgccactgg    720
cggccgcttt tatagagcgt gtccctccgg aggctcggcg gcgacaggca aggaacagct    780
ttggtgtcgg tttcccggggg ccgagttcca ggaggagggc ggctccggcg cgagcgtctg    840
tcgccggggc ctcggcgcga tgcgctcgcc ggagattgga ctccggagct gcgagggagt    900
gtcgccgtcg cccgtgtcgc ccgtgtccgc tccgcctcgc tcccggagga ggccgtgcgg    960
gccgcctggg tgggtcgacc agcaccgccg gtggctcctc ctcgcccgcg cggaccgacc   1020
tgggcgcctc gggggcgggg gacagggtgt gtcccgccgt ccgtcctgtg gctccgggcg   1080
atcttcgggc cttccttccg tgtcactcgg ttgtctcccg tggtcacgcc ctggcgacgg   1140
ggaccggtct gagcctggag gggaagcccg tgggtggcgc gacagacccg gctgcgggca   1200
cgtgtggggg tcccgggcgt cggacgcgat tttctcccct ttttccgagg cccgctgcgg   1260
aggtgggtcc cgggcggtcg gacccgggtgc cacgcgggggg tgggcgggcc gtccgttcgg   1320
gcgtccggcc ccggtggcga ttcccggtga ggctgcctct gccgcgcgtg gccctccacc   1380
tccccctggcc cgagccgggg ttggggacgg cggtaggcac ggggcggtcc tgagggccgc   1440
gggggacggc ctccgcacgg tgcctgcctc cggagaactt tgatgatttt tcaaagtctc   1500
ctcccggaga tcactggctt ggcggcgtgg cggcgtggcg gcgtggcggc gtggcggcgt   1560
ggcggcgtgg cgtctccacc gaccgcgtat cgcccctcct cccctccccc ccccccccg   1620
ttccctgggt cgaccagata gccctggggg ctccgtgggg tggggtggg ggggcgccgt   1680
ggggcaggtt ttgggggacag ttggccgtgt cacggtcccg ggaggtcgcg gtgacctgtg   1740
gctggtcccc gccggcaggc gcggttattt tcttgcccga gatgaacatt ttttgttgcc   1800
aggtaggtgc tgacacgttg tgtttcggcg acaggcagac agacgacagg cagacgtaaa   1860
agacagccgg tccgtccgtc gctcgcctta gagatgtggg cctctgggcg cgggtggggt   1920
tccgggcttg accgcgcggc cgagccggtc cctgtcctcg ctcgctggag cctgagccgt   1980
ccgcctgggc ctgcgcgccg gctctcgtgc tggactccag gtggcccggg tcgcggtgtc   2040
gccctccggt ctccggcacc cgaggagggg cggtgtgggc aggtggcggt gggtctttta   2100
ccccccgtgcg ctccatgccg tgggcacccg gccgttggcc gtgacaaccc ctgtctcgca   2160
aggtccgtg ccgcgtgtca ggcgtccccc gctgtgtctg gggttgtccg gtcgctcctg   2220
cccccccccc cccgggggtc gaggggcttg ccggtgaggc ggaagcaggt ccccccggtc   2280
```

```
gccgtcctcg ctgggctttt gctcctcggg aagcccctc ggggccgcag cttgctgccg    2340
atcgatcgat gtggtgatct cgtgctctcc tgggccgggc ctaagccgcg tcagacgagg    2400
gacgggcgtc cacggcggat gcgaccgctc ttctcgttct gcccgcgggc ccctccctcc    2460
ccggctcctc cgcgcccggc cgtcgtggcg ggtgcgcggg gggcgcgcgc cggggtgggg    2520
ggtggtgcgg actccggccc gaccccggcc tccgccttc ttgcctcgcg cgcctggcgg    2580
gaccggggtc ctcggacgcg gcggacactc tcgccggcct ttcccgaagg ccctgggtcc    2640
gtggcgagcg gccctcccct cctccgcggg ggagggccgg cccgacgccg cgctgctcac    2700
cgcccggcct gggcgcgctt gagcgcgttg cgcccgccc tccgtggtgc cctggagcg     2760 ctccaggtcg cctcaggtgc ctgaggccga gcggtggcgt cgtttccttc cccggcgact    2820
cccctcgggc tgccgccgcc gtcgtcgcg tgtccgagga gcggtggtg gaagaagtcg     2880 gcaagggagg cgcacccgtg ccctggcgg gggcgcgggc gcctcgtctt cctttccctc    2940
tcctctcctc cccctcgcg cgccggcggg gggtgggtgg cgtggggcgg tgtgactcgg    3000
aggacttggc ggggctcgtg aggccgcggc gggccgggcc acgccgcggc gcttgccagc    3060 cgagggggctg cccctctctc cggcacgggt cgtgtccccg tctccgtccc tctctctcgc    3120
gctcgcggga ggcggggagc tctctcctct gggcggtgac gtgaccacgc cgtgcgcggg    3180
cgaggcgggg gtggcgtcct cgagggggca ccggccgcga gcgctcgggg ttgccctgtg    3240 cctgtcccctt gccggagatc cgccccccgc cccgcgagcc tgtcggcccc ggagcgccgc    3300 ctggtgggc ccgtttggga ggacgaacg gtggggcgat gcgccctcgg tgagaaagcc     3360
ttctctagcg atccgagagg gtgccttggg gtaccggagc cccagccgc tgcccctcct    3420 ctgcgcgtgt agtgtggcca gcgacgcggg gttggactcc cgtcgcgacg tgtttgggca    3480
gagtgccgct ctttgcctac ctacccgcgc tgcgctcccc cctccgagac gggggag      3537

<210> SEQ ID NO 2
<211> LENGTH: 333
<212> TYPE: DNA
<213> ORGANISM: Canis familiaris

<400> SEQUENCE: 2
ttgatgattt ttcaaagtcc tcccggagat cactggcttg gcggcgtggc ggcgtggcgg      60
cgtggcggcg tggcggcgtg gcggcgtggc gtctccaccg acccgtatcg cccctcctcc    120
cctccccccc cccccccgtt ccctgggtcg accagatagc cctgggggct ccgtgggggtg   180 ggggtggggg ggcgccgtgg ggcaggtttt ggggacagtt ggccgtgtca cggtcccggg    240
aggtcgcggt gacctgtggc tggtccccgc cggcaggcgc ggttattttc ttgcccgaga    300
tgaacatttt ttgttgccag gtaggtgctg aca                                 333

<210> SEQ ID NO 3
<211> LENGTH: 168
<212> TYPE: DNA
<213> ORGANISM: Canis familiaris

<400> SEQUENCE: 3
gggctccgtg gggtgggggt gggggggcgc cgtggggcag gttttgggga cagttggccg     60
tgtcacggtc ccgggaggtc gcggtgacct gtggctggtc cccgccggca ggcgcggtta    120
ttttcttgcc cgagatgaac atttttgtt gccaggtagg tgctgaca                  168

<210> SEQ ID NO 4
<211> LENGTH: 140
```

```
<212> TYPE: DNA
<213> ORGANISM: Canis familiaris

<400> SEQUENCE: 4
gccgtggggc aggttttggg gacagttggc cgtgtcacgg tcccgggagg tcgcggtgac      60
ctgtggctgg tccccgccgg caggcgcggt tattttcttg cccgagatga acattttttg     120
ttgccaggta ggtgctgaca                                                  140

<210> SEQ ID NO 5
<211> LENGTH: 114
<212> TYPE: DNA
<213> ORGANISM: Canis familiaris

<400> SEQUENCE: 5
tggccgtgtc acggtcccgg gaggtcgcgg tgacctgtgg ctggtccccg ccggcaggcg      60
cggttatttt cttgcccgag atgaacattt tttgttgcca ggtaggtgct gaca           114

<210> SEQ ID NO 6
<211> LENGTH: 85
<212> TYPE: DNA
<213> ORGANISM: Canis familiaris

<400> SEQUENCE: 6
gtgacctgtg gctggtcccc gccggcaggc gcggttattt tcttgcccga gatgaacatt      60
ttttgttgcc aggtaggtgc tgaca                                            85

<210> SEQ ID NO 7
<211> LENGTH: 59
<212> TYPE: DNA
<213> ORGANISM: Canis familiaris

<400> SEQUENCE: 7
aggcgcggtt attttcttgc ccgagatgaa cattttttgt tgccaggtag gtgctgaca       59

<210> SEQ ID NO 8
<211> LENGTH: 164
<212> TYPE: DNA
<213> ORGANISM: Canis familiaris

<400> SEQUENCE: 8
ttgatgattt ttcaaagtcc tcccggagat cactggcttg gcggcgtggc ggcgtggcgg      60
cgtggcggcg tggcggcgtg gcggcgtggc gtctccaccg acccgtatcg cccctcctcc     120
cctccccccc ccccccgtt ccctgggtcg accagatagc cctg                       164

<210> SEQ ID NO 9
<211> LENGTH: 137
<212> TYPE: DNA
<213> ORGANISM: Canis familiaris

<400> SEQUENCE: 9
ttgatgattt ttcaaagtcc tcccggagat cactggcttg gcggcgtggc ggcgtggcgg      60
cgtggcggcg tggcggcgtg gcggcgtggc gtctccaccg acccgtatcg cccctcctcc     120
cctccccccc ccccccc                                                    137

<210> SEQ ID NO 10
<211> LENGTH: 109
<212> TYPE: DNA
<213> ORGANISM: Canis familiaris

<400> SEQUENCE: 10
```

```
ttgatgattt tcaaagtcc tcccggagat cactggcttg gcggcgtggc ggcgtggcgg    60
cgtggcggcg tggcggcgtg gcggcgtggc gtctccaccg acccgtatc             109

<210> SEQ ID NO 11
<211> LENGTH: 55
<212> TYPE: DNA
<213> ORGANISM: Canis familiaris

<400> SEQUENCE: 11
ttgatgattt tcaaagtcc tcccggagat cactggcttg gcggcgtggc ggcgt         55

<210> SEQ ID NO 12
<211> LENGTH: 299
<212> TYPE: DNA
<213> ORGANISM: Canis familiaris

<400> SEQUENCE: 12
ttgatgattt tcaaagtcc tcccggagat cactggcttg gcggcgtggc ggcgtggcgg    60
cgtggcggcg tggcggcgtg gcggcgtggc gtctccaccg acccgtatcg cccctcctcc   120 cctcccccc ccccccgtt ccctgggtcg accagatagc cctgggggct ccgtggggtg    180
ggggtggggg ggcgccgtgg ggcaggtttt ggggacagtt ggccgtgtca cggtcccggg   240
aggtcgcggt gacctgtggc tggtccccgc cggcaggcgc ggttattttc ttgcccgag   299

<210> SEQ ID NO 13
<211> LENGTH: 244
<212> TYPE: DNA
<213> ORGANISM: Canis familiaris

<400> SEQUENCE: 13
ggcggcgtgg cggcgtggcg gcgtggcggc gtggcgtctc caccgacccg tatcgcccct    60
cctcccctcc ccccccccc ccgttccctg ggtcgaccag atagccctgg gggctccgtg   120
gggtgggggt ggggggcgc cgtggggcag gttttgggga cagttggccg tgtcacggtc   180 ccggaggtc gcggtgacct gtggctggtc cccgccggca ggcgcggtta ttttcttgcc   240
cgag                                                              244

<210> SEQ ID NO 14
<211> LENGTH: 190
<212> TYPE: DNA
<213> ORGANISM: Canis familiaris

<400> SEQUENCE: 14
gcccctcctc cctcccccc ccccccccgt tccctgggtc gaccagatag ccctgggggc    60
tccgtggggt ggggtgggg gggcgccgtg ggcaggttt tggggacagt tggccgtgtc   120
acggtcccgg gaggtcgcgg tgacctgtgg ctggtccccg ccggcaggcg cggttatttt   180
cttgcccgag                                                        190

<210> SEQ ID NO 15
<211> LENGTH: 134
<212> TYPE: DNA
<213> ORGANISM: Canis familiaris

<400> SEQUENCE: 15
gggctccgtg gggtgggggt ggggggcgc cgtggggcag gttttgggga cagttggccg    60
tgtcacggtc ccggaggtc gcggtgacct gtggctggtc cccgccggca ggcgcggtta   120
ttttcttgcc cgag                                                   134
```

<210> SEQ ID NO 16
<211> LENGTH: 106
<212> TYPE: DNA
<213> ORGANISM: Canis familiaris

<400> SEQUENCE: 16

```
gccgtggggc aggttttggg gacagttggc cgtgtcacgg tcccgggagg tcgcggtgac    60
ctgtggctgg tccccgccgg caggcgcggt tattttcttg cccgag                  106
```

<210> SEQ ID NO 17
<211> LENGTH: 80
<212> TYPE: DNA
<213> ORGANISM: Canis familiaris

<400> SEQUENCE: 17

```
tggccgtgtc acggtcccgg gaggtcgcgg tgacctgtgg ctggtccccg ccggcaggcg    60
cggttatttt cttgcccgag                                                80
```

<210> SEQ ID NO 18
<211> LENGTH: 217
<212> TYPE: DNA
<213> ORGANISM: Canis familiaris

<400> SEQUENCE: 18

```
ggcgtggcgt ctccaccgac ccgtatcgcc cctcctcccc tccccccccc ccccgttcc    60 ctgggtcgac cagatagccc tgggggctcc gtggggtggg ggtgggggggg cgccgtgggg  120 caggttttgg ggacagttgg ccgtgtcacg gtcccgggag gtcgcggtga cctgtggctg  180
gtccccgccg gcaggcgcgg ttattttctt gcccgag                            217
```

<210> SEQ ID NO 19
<211> LENGTH: 56
<212> TYPE: DNA
<213> ORGANISM: Canis familiaris

<400> SEQUENCE: 19

```
tcgcggtgac ctgtggctgg tccccgccgg caggcgcggt tattttcttg cccgag        56
```

<210> SEQ ID NO 20
<211> LENGTH: 336
<212> TYPE: DNA
<213> ORGANISM: Canis familiaris

<400> SEQUENCE: 20

```
ttgatgattt ttcaaagtct cctcccggag atcactggct tggcggcgtg gcggcgtggc    60
ggcgtggcgg cgtggcggcg tggcggcgtg gcgtctccac cgaccgcgta tcgcccctcc  120
tccccctccc cccccccccc gttccctggg tcgaccagat agccctgggg gctccgtggg  180 gtggggggtgg ggggcgccg tggggcaggt tttggggaca gttggccgtg tcacggtccc  240
gggaggtcgc ggtgacctgt ggctggtccc cgccggcagg cgcggttatt tcttgcccg   300 agatgaacat ttttttgttgc caggtaggtg ctgaca                             336
```

<210> SEQ ID NO 21
<211> LENGTH: 167
<212> TYPE: DNA
<213> ORGANISM: Canis familiaris

<400> SEQUENCE: 21

```
ttgatgattt ttcaaagtct cctcccggag atcactggct tggcggcgtg gcggcgtggc    60
```

```
ggcgtggcgg cgtggcggcg tggcggcgtg gcgtctccac cgaccgcgta tcgcccctcc    120 tccccctcccc cccccccccc gttccctggg tcgaccagat agccctg                 167

<210> SEQ ID NO 22
<211> LENGTH: 140
<212> TYPE: DNA
<213> ORGANISM: Canis familiaris

<400> SEQUENCE: 22
ttgatgattt ttcaaagtct cctcccggag atcactggct tggcggcgtg gcggcgtggc    60
ggcgtggcgg cgtggcggcg tggcggcgtg gcgtctccac cgaccgcgta tcgcccctcc    120 tccccctcccc cccccccccc                                               140

<210> SEQ ID NO 23
<211> LENGTH: 112
<212> TYPE: DNA
<213> ORGANISM: Canis familiaris

<400> SEQUENCE: 23
ttgatgattt ttcaaagtct cctcccggag atcactggct tggcggcgtg gcggcgtggc    60
ggcgtggcgg cgtggcggcg tggcggcgtg gcgtctccac cgaccgcgta tc            112

<210> SEQ ID NO 24
<211> LENGTH: 57
<212> TYPE: DNA
<213> ORGANISM: Canis familiaris

<400> SEQUENCE: 24
ttgatgattt ttcaaagtct cctcccggag atcactggct tggcggcgtg gcggcgt       57

<210> SEQ ID NO 25
<211> LENGTH: 302
<212> TYPE: DNA
<213> ORGANISM: Canis familiaris

<400> SEQUENCE: 25
ttgatgattt ttcaaagtct cctcccggag atcactggct tggcggcgtg gcggcgtggc    60
ggcgtggcgg cgtggcggcg tggcggcgtg gcgtctccac cgaccgcgta tcgcccctcc    120 tccccctcccc cccccccccc gttccctggg tcgaccagat agccctgggg gctccgtggg   180 gtggggggtgg gggggcgccg tggggcaggt tttggggaca gttggccgtg tcacggtccc   240
gggaggtcgc ggtgacctgt ggctggtccc cgccggcagg cgcggttatt ttcttgcccg    300
ag                                                                   302

<210> SEQ ID NO 26
<211> LENGTH: 469
<212> TYPE: DNA
<213> ORGANISM: Canis familiaris

<400> SEQUENCE: 26
attcccggtg aggctgcctc tgccgcgcgt ggccctccac ctcccctggc ccgagccggg    60
gttggggacg gcggtaggca cggggcggtc ctgagggccg cggggggacgg cctccgcacg   120 gtgcctgcct ccggagaaact ttgatgattt ttcaaagtct cctcccggag atcactggct   180
tggcggcgtg gcggcgtggc ggcgtggcgg cgtggcggcg tggcggcgtg gcgtctccac   240
cgaccgcgta tcgcccctcc tccccctcccc cccccccccc gttccctggg tcgaccagat   300
agccctgggg gctccgtggg gtggggggtgg gggggcgccg tggggcaggt tttggggaca   360
```

```
gttggccgtg tcacggtccc gggaggtcgc ggtgacctgt ggctggtccc cgccggcagg    420
cgcggttatt ttcttgcccg agatgaacat tttttgttgc caggtaggt                469

<210> SEQ ID NO 27
<211> LENGTH: 245
<212> TYPE: DNA
<213> ORGANISM: Canis familiaris

<400> SEQUENCE: 27
ggcggcgtgg cggcgtggcg gcgtggcggc gtggcgtctc caccgaccgc gtatcgcccc     60
tcctcccctc ccccccccc cccgttccct gggtcgacca gatagccctg ggggctccgt    120
ggggtggggg tggggggcg ccgtggggca ggttttgggg acagttggcc gtgtcacggt     180
cccgggaggt cgcggtgacc tgtggctggt ccccgccggc aggcgcggtt attttcttgc    240
ccgag                                                               245

<210> SEQ ID NO 28
<211> LENGTH: 218
<212> TYPE: DNA
<213> ORGANISM: Canis familiaris

<400> SEQUENCE: 28
ggcgtggcgt ctccaccgac cgcgtatcgc ccctcctccc ctccccccccc ccccccgttc     60 cctgggtcga ccagatagcc ctgggggctc cgtggggtgg gggtgggggg cgccgtggg    120 gcaggttttg gggacagttg gccgtgtcac ggtcccggga ggtcgcggtg acctgtggct    180
ggtccccgcc ggcaggcgcg gttattttct tgcccgag                           218

<210> SEQ ID NO 29
<211> LENGTH: 3100
<212> TYPE: DNA
<213> ORGANISM: Artificial
<220> FEATURE:
<223> OTHER INFORMATION: plasmid

<400> SEQUENCE: 29
acctacctgg caacaaaaaa tgttcatctc gggcaagaaa ataaccgcgc ctgccggcgg     60
ggaccagcca caggtcaccg cgacctcccg ggaccgtgac acggccaact gtccccaaaa    120
cctgccccac ggcgcccccc caccccaccc ccacggagcc cccagggcta tctggtcgac    180
ccagggaacg gggggggggg gggaggggag gaggggcgat acgcggtcgg tggagacgcc    240
acgccgccac gccgccacgc cgccacgccg ccacgccgcc acgccgccaa gccagtgatc    300
tccgggagga gactttgaaa aatcatcaaa gttctccgga ggcaggcacc gtgcggaggc    360
cgtcccccgc ggccctcagg accgcccgt gcctaccgcc gtccccaacc ccggctcggg    420
ccaggggagg tggagggcca cgcgcggcag aggcagcctc accgggaata tcgggcccgt    480
cacctcagac atgataagat acattgatga gtttggacaa accacaacta gaatgcagtg    540
aaaaaaatgc tttatttgtg aaatttgtga tgctattgct ttatttgtaa ccattataag    600
ctgcaataaa caaggatctg cattaatgaa tcggccaacg cgcggggaga ggcggtttgc    660
gtattgggcg ctcttccgct tcctcgctca ctgactcgct gcgctcggtc gttcggctgc    720
ggcgagcggt atcagctcac tcaaaggcgg taatacggtt atccacagaa tcaggggata    780
acgcaggaaa gaacatgtga gcaaaaggcc agcaaaaggc caggaaccgt aaaaaggccg    840
cgttgctggc gtttttccat aggctccgcc ccctgacga gcatcacaaa aatcgacgct    900
caagtcagag gtggcgaaac ccgacaggac tataaagata ccaggcgttt ccccctggaa    960
```

```
gctccctcgt gcgctctcct gttccgaccc tgccgcttac cggataccctg tccgcctttc   1020 tcccttcggg aagcgtggcg ctttctcaat gctcacgctg taggtatctc agttcggtgt   1080
aggtcgttcg ctccaagctg gctgtgtgc acgaacccccc cgttcagccc gaccgctgcg   1140
ccttatccgg taactatcgt cttgagtcca acccggtaag acacgactta tcgccactgg   1200
cagcagccac tggtaacagg attagcagag cgaggtatgt aggcggtgct acagagttct   1260
tgaagtggtg gcctaactac ggctacacta gaaggacagt atttggtatc tgcgctctgc   1320
tgaagccagt taccttcgga aaaagagttg gtagctcttg atccggcaaa caaaccaccg   1380
ctggtagcgg tggttttttt gtttgcaagc agcagattac gcgcagaaaa aaggatctc   1440 aagaagatcc tttgatcttt tctacggggt ctgacgctca gtggaacgaa aactcacgtt   1500
aagggatttt ggtcatgaga ttatcaaaaa ggatcttcac ctagatcctt ttaaattaaa   1560
aatgaagttt taaatcaatc taaagtatat atgagtaaac ttggtctgac agttaccaat   1620
gcttaatcag tgaggcacct atctcagcga tctgtctatt tcgttcatcc atagttgcct   1680
gactccccgt cgtgtagata actacgatac gggagggctt accatctggc cccagtgctg   1740
caatgatacc gcgagaccca cgctcaccgg ctccagattt atcagcaata aaccagccag   1800
ccggaagggc cgagcgcaga agtggtcctg caactttatc cgcctccatc cagtctatta   1860
attgttgccg ggaagctaga gtaagtagtt cgccagttaa tagtttgcgc aacgttgttg   1920
ccattgctac aggcatcgtg gtgtcacgct cgtcgtttgg tatggcttca ttcagctccg   1980
gttcccaacg atcaaggcga gttacatgat cccccatgtt gtgcaaaaaa gcggttagct   2040
ccttcggtcc tccgatcgtt gtcagaagta agttggccgc agtgttatca ctcatggtta   2100
tggcagcact gcataattct cttactgtca tgccatccgt aagatgcttt tctgtgactg   2160
gtgagtactc aaccaagtca ttctgagaat agtgtatgcg gcgaccgagt tgctcttgcc   2220
cggcgtcaat acgggataat accgcgccac atagcagaac tttaaaagtg ctcatcattg   2280
gaaaacgttc ttcggggcga aaactctcaa ggatcttacc gctgttgaga tccagttcga   2340
tgtaacccac tcgtgcaccc aactgatctt cagcatcttt tactttcacc agcgtttctg   2400
ggtgagcaaa aacaggaagg caaaatgccg caaaaaaggg aataagggcg acacggaaat   2460
gttgaatact catactcttc ctttttcaat attattgaag catttatcag ggttattgtc   2520
tcatgagcgg atacatattt gaatgtattt agaaaaataa acaaataggg gttccgcgca   2580
catttccccg aaaagtgcca cctgacgtcg atatgccaag tacgcccct attgacgtca   2640 atgacggtaa atggcccgcc tggcattatg cccagtacat gaccttatgg actttccta   2700 cttggcagta catctacgta ttagtcatcg ctattaccat ggtgatgcgg ttttggcagt   2760
acatcaatgg gcgtggatag cggtttgact cacggggatt tccaagtctc cacccattg   2820 acgtcaatgg gagtttgttt tggcaccaaa atcaacggga ctttccaaaa tgtcgtaaca   2880
actccgcccc attgacgcaa atgggcggta ggcgtgtacg gtgggaggtc tatataagca   2940
gagctctctg gctaactaga gaacccactg cttactggct tatcgaaatt aatacgactc   3000
actataggga gacccaagct gttaacgcta gctagcagtt aaccggagta ctggtcgacc   3060
tccgaagttg gggggagag tcttctcgag tagaagaccg                          3100
```

<210> SEQ ID NO 30
<211> LENGTH: 18
<212> TYPE: DNA
<213> ORGANISM: Artificial
<220> FEATURE:
<223> OTHER INFORMATION: sythetic linker

```
<400> SEQUENCE: 30
aggagacggt accgtctc                                                 18

<210> SEQ ID NO 31
<211> LENGTH: 24
<212> TYPE: DNA
<213> ORGANISM: Artificial
<220> FEATURE:
<223> OTHER INFORMATION: sythetic linker

<400> SEQUENCE: 31
agagtcttct cgagtagaag accg                                          24

<210> SEQ ID NO 32
<211> LENGTH: 119
<212> TYPE: DNA
<213> ORGANISM: Influenza B virus

<400> SEQUENCE: 32 aaa

```
<212> TYPE: DNA
<213> ORGANISM: Artificial
<220> FEATURE:
<223> OTHER INFORMATION: sythetic primer

<400> SEQUENCE: 37
tctctttatg aggaaaccct                                                    20

<210> SEQ ID NO 38
<211> LENGTH: 20
<212> TYPE: DNA
<213> ORGANISM: Canis familiaris

<400> SEQUENCE: 38
gtgagcctga aagtaaaagg                                                    20

<210> SEQ ID NO 39
<211> LENGTH: 20
<212> TYPE: DNA
<213> ORGANISM: Artificial
<220> FEATURE:
<223> OTHER INFORMATION: sythetic primer

<400> SEQUENCE: 39
gcaacaagtt tagcaacaag                                                    20

<210> SEQ ID NO 40
<211> LENGTH: 423
<212> TYPE: DNA
<213> ORGANISM: Influenza B virus

<400> SEQUENCE: 40
tcattgattc attggacaaa cctgaaatga ctttcttctc ggtaaagaat ataaagaaaa         60
aattgcctgc taaaaacaga aagggtttcc tcataaagag aataccaatg aaggtaaaag       120
acagaataac cagagtggaa tacatcaaaa gagcattatc attaaacaca atgacaaaag       180
atgctgaaag aggcaaacta aaaagaagag caattgccac cgctgggata caaatcagag       240
ggtttgtatt agtagttgaa aacttggcta aaaatatctg tgaaaatcta aacaaagtg       300
gtttgccagt aggtgggaac gagaagaagg ccaaactgtc aaatgcagtg gccaaaatgc       360
tcagtaactg cccaccagga gggatcagca tgacagtgac aggagacaat actaaatgga       420
atg                                                                    423

<210> SEQ ID NO 41
<211> LENGTH: 423
<212> TYPE: DNA
<213> ORGANISM: Influenza B virus

<400> SEQUENCE: 41
tcattgattc attggacaaa cctgaaatga ccttcttctc ggtaaagaat ataaagaaaa         60
aattgcctgc taaaaacaga aagggtttcc tcataaagag aataccaatg aaggtaaaag       120
acagaataac cagagtggaa tacatcaaaa gagcattatc attaaacaca atgacaaaag       180
atgctgaaag aggcaaacta aaaagaagag caattgccac cgctgggata caaatcagag       240
ggtttgtatt agtagttgaa aacttggcta aaaatatctg tgaaaatcta aacaaagtg       300
gtttgccagt aggtgggaac gagaagaagg ccaaactgtc aaatgcagtg gccaaaatgc       360
tcagtaactg cccaccagga gggatcagca tgacggtgac aggagacaat actaaatgga       420
atg                                                                    423
```

METHODS AND COMPOSITIONS FOR EXPRESSING NEGATIVE-SENSE VIRAL RNA IN CANINE CELLS

1. CROSS REFERENCE TO RELATED APPLICATIONS

This application is a continuation in part and claims the benefit under 35 U.S.C. §120 of U.S. patent application Ser. No. 11/455,734, filed Jun. 20, 2006, which claims priority under 35 U.S.C. §119(e) of the following U.S. Provisional Application Nos.: U.S. 60/793,522, filed Apr. 19, 2006; U.S. 60/793,525, filed Apr. 19, 2006; U.S. 60/702,006, filed Jul. 22, 2005; U.S. 60/699,556, filed Jul. 15, 2005; U.S. 60/699,555, filed Jul. 15, 2005; U.S. 60/692,965 filed Jun. 21, 2005; and U.S. 60/692,978 filed Jun. 21, 2005. The priority applications are hereby incorporated by reference herein in their entirety for all purposes.

2. FIELD OF THE INVENTION

In one aspect, the present invention provides an isolated nucleic acid comprising a canine RNA polymerase I regulatory sequence. In other aspects, the invention provides expression vectors and cells comprising such nucleic acids as well as methods of using such nucleic acids to make influenza viruses, including infectious influenza viruses.

3. BACKGROUND

Influenza pandemics are defined by a dramatic global increase in morbidity and mortality due to influenza illness. Several factors combine to modulate the severity and extent of the pandemic including the low degree of immunity in the population and the efficiency with which the virus can transmit among humans. The latter is generally influenced not only by the virus itself but the density of the population and ease of travel into and out of a region. The virus responsible for the pandemic is generally a recently emerged antigenic variant that the majority of the population have not had prior experience with and, therefore, have little or no immunity to. In addition, efficient human to human transmission is a prerequisite for rapid spread and, in the case of zoonotic introduction of animal viruses into human populations, the virus must adapt to replication in humans and be capable of efficient transmission.

Pandemic influenza spreads very quickly and can have devastating impact. The most severe pandemic of the 20$^{th}$ century, the 1918 pandemic, killed over 500,000 U.S. citizens and between 20 to 40 million people worldwide. The pandemic may produce waves of disease, with peaks of incidence separated by several weeks to months. The relatively rapid onset and spread of pandemic influenza presents several problems for responding to a global attack of this magnitude and imposes overwhelming burdens on emergency responders and health care workers. Rapid identification and response to the emerging pandemic is clearly a necessary element of the solution; several programs are currently in place worldwide to monitor emerging influenza viruses including avian influenza viruses that infrequently cause disease in humans. These surveillance data are used in conjunction with predefined pandemic alert levels in order to identify the likelihood of the threat and provide guidance for an effective response.

Vaccination is the most important public health measure for preventing disease caused by annual epidemics of influenza. The short interval between identification of a potential pandemic and the onset of significantly increased disease levels present significant challenges for producing sufficient vaccine to protect a large segment of the population. Having vaccine technology and manufacturing infrastructure in place prior to the emergence of the next pandemic will be critical in ameliorating a significant amount of illness and death. The short response times needed to produce a "pandemic vaccine" will not allow for prolonged research or process development to be conducted in order to provide an effective response.

To date, all commercially available influenza vaccines for non-pandemic strains in the United States have been propagated in embryonated hen's eggs. Although influenza virus grows well in hen's eggs, production of vaccine is dependent on the availability of eggs. Supplies of eggs must be organized, and strains for vaccine production selected months in advance of the next flu season, limiting the flexibility of this approach, and often resulting in delays and shortages in production and distribution. Unfortunately, some influenza vaccine strains, such as the prototype A/Fujian/411/02 strain that circulated during the 2003-04 season, do not replicate well in embryonated chicken eggs, and have to be isolated by cell culture in a costly and time consuming procedure.

Systems for producing influenza viruses in cell culture have also been developed in recent years (See, e.g., Furminger. Vaccine Production, in Nicholson et al. (eds) *Textbook of Influenza* pp. 324-332; Merten et al. (1996) Production of influenza virus in cell cultures for vaccine preparation, in Cohen & Shafferman (eds) *Novel Strategies in Design and Production of Vaccines* pp. 141-151). Typically, these methods involve the infection of suitable immortalized host cells with a selected strain of virus. While eliminating many of the difficulties related to vaccine production in hen's eggs, not all pathogenic strains of influenza grow well and can be produced according to established tissue culture methods. In addition, many strains with desirable characteristics, e.g., attenuation, temperature sensitivity and cold adaptation, suitable for production of live attenuated vaccines, have not been successfully grown in tissue culture using established methods.

In addition to cell culture-based methods that rely on infecting the cell culture with live virus, fully infectious influenza viruses have been produced in cell culture using recombinant DNA technology. Production of influenza viruses from recombinant DNA significantly increases the flexibility and utility of tissue culture methods for influenza vaccine production. Recently, systems for producing influenza A and B viruses from recombinant plasmids incorporating cDNAs encoding the viral genome have been reported See, e.g., Neumann et al. (1999) Generation of influenza A virus entirely from cloned cDNAs. *Proc Natl Acad Sci USA* 96:9345-9350; Fodor et al. (1999) Rescue of influenza A virus from recombinant DNA. *J. Virol* 73:9679-9682; Hoffmann et al. (2000) A DNA transfection system for generation of influenza A virus from eight plasmids *Proc Natl Acad Sci USA* 97:6108-6113; WO 01/83794; Hoffmann and Webster (2000), *Unidirectional RNA polymerase I-polymerase II transcription system for the generation of influenza A virus from eight plasmids,* 81:2843-2847; Hoffmann et al. (2002), *Rescue of influenza B viruses from 8 plasmids,* 99(17): 11411-11416; U.S. Pat. Nos. 6,649,372 and 6,951,754; U.S. publication nos. 20050003349 and 20050037487, which are incorporated by reference herein. These systems, often referred to as "plasmid rescue," offer the potential to produce recombinant viruses expressing the immunogenic HA and NA proteins from any selected strain.

However, these recombinant methods rely on use of expression vectors comprising RNA polymerase I (RNA pol I) regulatory elements to drive transcription of viral genomic rRNA. Such regulatory elements are necessary to produce the defined 5' and 3' ends of the influenza genomic RNA such that a fully infectious influenza virus can be made. Current recombinant systems, such as those described above, use the human RNA pol I regulatory system to express viral RNA. Because of the species specificity of the RNA pol I promoter, these regulatory elements are only active in human or primate cells. Thus, plasmid rescue of influenza virus has to date been possible only by transfecting appropriate plasmids into human or primate cells.

Further, such human or primate cells frequently do not yield a sufficient titer of influenza virus required for vaccine manufacture. Instead, Madin-Darby canine kidney cells (MDCK cells) can be used to replicate vaccine strains to a sufficient titer to manufacture commercial vaccines. Thus, production of an influenza vaccine using plasmid rescue presently requires use of at least two different cell cultures. Identification and cloning of the canine RNA pol I regulatory sequences would allow plasmid rescue to be performed in the same cell culture as viral replication, eliminating the need for a separate rescue culture. As such, there remains a need for identification and cloning of canine RNA pol I regulatory elements which can be utilized to construct appropriate vectors for plasmid rescue in MDCK and other canine cells. These and other unmet needs are provided by the present invention.

Citation or discussion of a reference herein shall not be construed as an admission that such is prior art to the present invention. In addition, citation of a patent shall not be construed as an admission of its validity.

4. SUMMARY

Disclosed herein are nucleic acids which comprise regulatory elements that can be used to express, for example, influenza genomic RNA in canine cells. Compositions such as isolated nucleic acids, vectors, and cells comprising the canine regulatory sequences of the invention, and methods of using the same are embodiments of the subject invention.

Accordingly, in certain aspects, isolated nucleic acids of the invention comprise a canine RNA polymerase I (pol I) regulatory sequence. In certain embodiments, the regulatory sequence comprises a promoter. In certain embodiments, the regulatory sequence comprises an enhancer. In certain embodiments, the regulatory sequence comprises both a promoter and an enhancer. In one embodiment, the regulatory sequence comprises nucleotides −250 to −1 (in relation to the first nucleotide transcribed from the promoter, also known as the +1 nucleotide) of the corresponding native promoter or a functional derivative thereof. In one embodiment, the regulatory sequence is operably linked to a viral DNA, e.g., a cloned viral cDNA. In one embodiment, the cloned viral cDNA encodes viral RNA of a negative or positive strand virus or the corresponding cRNA. In certain embodiments, the cloned viral cDNA encodes genomic viral RNA (or the corresponding cRNA) of an influenza virus.

In one embodiment, isolated nucleic acids of the invention comprise a canine RNA polymerase I regulatory sequence and a transcriptional termination sequence. In certain embodiments, the transcriptional termination sequence is an RNA polymerase I termination sequence. In a specific embodiment, the transcriptional termination sequence is a human, monkey, or canine pol I termination sequence.

In certain aspects, the present invention provides an isolated nucleic acid that comprises a canine RNA pol I promoter. Preferably, the canine RNA pol I promoter is operably linked to a nucleic acid to be transcribed, such as, e.g., an influenza genomic RNA. In one embodiment, introduction of the nucleic acid into a canine cell results in transcription of the influenza genomic RNA, and, in the presence of suitable influenza proteins, the RNA transcript can be packed into an infectious influenza virus. In one embodiment, isolated nucleic acids are provided which comprise a canine RNA regulatory sequence of the invention (e.g., a canine RNA pol I promoter), wherein the regulatory sequence is operably linked to a nucleic acid to be transcribed and, in the presence of suitable proteins (e.g., an RNP complex in the case of a nucleic acid encoding a influenza vRNA segment) in vitro or in vivo, is transcribed. In one embodiment, the nucleic acid operably linked to said regulatory sequence is an influenza vRNA segment.

In certain embodiments, nucleic acids of the invention comprise a polynucleotide sequence or a functionally active fragment thereof, e.g., a canine RNA pol I regulatory sequence, that binds a human, primate, mouse or canine pol I polypeptide and is at least 100% or about 99%, 98%, 97%, 96%, 95%, 90%, 85%, 80%, 75%, 70%, or 65% identical to one or more nucleotide sequences selected from the group consisting of: SEQ ID Nos: 1-28. In one embodiment, the polynucleotide sequence or functionally active fragment thereof further retains the ability to initiate transcription, in the presence of appropriate polypeptides (e.g., human, primate, mouse or canine pol I polypeptides), of a second polynucleotide sequence operatively linked to the nucleotide sequence. In one embodiment, "functionally active fragments" of the nucleic acids set forth in SEQ ID Nos: 1-28 retain one or more functional activities described herein of the full length sequences of SEQ ID Nos: 1-28. For instance, functionally active fragments of the regulatory sequence set forth as SEQ ID NO:1 are provided whereby the regulatory sequence fragment is operably linked to a nucleic acid to be transcribed and, in the presence of suitable proteins in vitro or in vivo, is transcribed.

In certain embodiments, nucleic acids of the invention comprise a polynucleotide sequence or a fragment thereof, e.g., a canine RNA pol I regulatory sequence, that binds a human, primate, mouse or canine pol I polypeptide and/or is 100% or at least or about 99%, 98%, 97%, 96%, 95%, 90%, 85%, 80%, 75%, 70%, or 65% identical to one or more nucleotide sequences selected from the group consisting of: SEQ ID Nos: 1-28. In one embodiment, the polynucleotide sequence or fragment thereof further retains the ability to initiate transcription, in the presence of appropriate polypeptides (e.g., human, primate, mouse or canine pol I polypeptides), of a second polynucleotide sequence operatively linked to the nucleotide sequence.

In other embodiments, isolated nucleic acids of the invention comprise a canine RNA polymerase I regulatory sequence and a ribozyme sequence. This may be, for example, the hepatitis delta virus genomic ribozyme sequence or a functional derivative thereof.

In one embodiment, nucleic acids of the invention encode genomic viral RNA from any negative-strand RNA virus known by one of skill in the art without limitation. In certain embodiments, the viral RNA encodes genomic viral RNA of a virus from the order Mononegavirales. In certain embodiments, the viral RNA encodes genomic viral RNA of a virus from the family Paramyxoviridae, Pneumovirinae, Rhabdoviridae, Filoviridae, Bornaviridae, Orthomyxoviridae, Bunyaviridae, or Arenaviridae. In certain embodiments, the viral RNA encodes genomic viral RNA of a virus from the genus Respirovirus, Morbillivirus, Rubulavirus, Henipavirus, Avulavirus, Pneumovirus, Metapneumovirus, Vesiculovirus, Lyssavirus, Ephemerovirus, Cytorhabdovirus, Nucleorhabdovirus, Novirhabdovirus, Marburgvirus, Ebolavirus, Bomavirus, Influenzavirus A, Influenzavirus B, Influenzavirus C, Thogotovirus, Isavirus, Orthobunyavirus, Hantavirus, Nairovirus, Phlebovirus, Tospovirus, Arenavirus, Ophiovirus, Tenuivirus, or Deltavirus. In certain embodiments, the viral RNA encodes genomic viral RNA of a virus selected from the group consisting of Sendai virus, Measles virus, Mumps virus, Hendra virus, Newcastle disease virus, Human respiratory syncytial virus, Avian pneumovirus, Vesicular stomatitis Indiana virus, Rabies virus, Bovine ephemeral fever virus, Lettuce necrotic yellows virus, Potato yellow dwarf virus, Infectious hematopoietic necrosis virus, Lake Victoria marburgvirus, Zaire ebolavirus, Borna disease virus, Influenza A virus, Influenza B virus, Influenza C virus, Thogoto virus, Infectious salmon anemia virus, Bunyamwera virus, Hantaan virus, Dugbe virus, Rift Valley fever virus, Tomato spotted wilt virus, Lymphocytic choriomeningitis virus, Citrus psorosis virus, Rice stripe virus, and Hepatitis delta virus.

In another aspect, the invention provides a vector comprising a nucleic acid of the invention. In certain embodiments, the vector is an expression vector. In certain embodiments, the vector comprises a bacterial origin of replication. In certain embodiments, the vector comprises a eukaryotic origin of replication. In certain embodiments, the vector comprises a selectable marker that can be selected in a prokaryotic cell. In certain embodiments, the vector comprises a selectable marker that can be selected in a eukaryotic cell. In certain embodiments, the vector comprises a multiple cloning site. In certain embodiments, the multiple cloning site is oriented relative to the canine RNA polymerase I regulatory sequence to allow transcription of polynucleotide sequence introduced into the multiple cloning site from the regulatory sequence. In certain embodiments, vector comprises a polynucleotide sequence that can be expressed in canine cells, e.g., in MDCK cells.

In one embodiment, the invention provides expression vectors useful for recombinantly rescuing a virus from cell culture, e.g., MDCK cell cultures. Generally, the vectors are useful for rescuing any virus known to one skilled in the art to require production of RNA with defined ends during its lifecycle. Such viruses include, but are not limited to, negative-sense strand RNA viruses, such as those described above. Preferably, the virus is an influenza virus, e.g., an influenza A, influenza B, or influenza C virus.

In certain embodiments, one or more of the vectors of the invention further comprises a RNA transcription termination sequence. In certain embodiments, the transcription termination sequence is selected from the group consisting of a RNA polymerase I transcription termination sequence, RNA polymerase II transcription termination sequence, RNA polymerase III transcription termination sequence, and a ribozyme.

In certain embodiments, the expression vectors are unidirectional expression vectors. In other embodiments, the expression vectors are bi-directional expression vectors. In some embodiments, the bi-directional expression vectors of the invention incorporate a first promoter inserted between a second promoter and a polyadenylation site, e.g., an SV40 polyadenylation site. In certain embodiments, the first promoter is a canine RNA pol I promoter. In certain embodiments, the second promoter is a canine RNA pol I promoter. In one embodiment, the first promoter and the second promoter can be situated in opposite orientations flanking at least one cloning site.

In certain embodiments, the expression vectors comprise a ribozyme sequence or transcription termination sequence 3' of at least one cloning site relative to the canine RNA pol I promoter. In certain embodiments, the expression vectors comprise a ribozyme sequence or transcription termination sequence 3' of at least one cloning site relative to the canine RNA pol I promoter such that vRNA can be intracellularly synthesized with exact 5' and 3' ends.

In one embodiment, in the bi-directional expression vectors of the invention, a gene or cDNA is located between an upstream pol II promoter and a downstream canine pol I regulatory sequence (e.g., a pol I promoter) of the invention. Transcription of the gene or cDNA from the pol II promoter produces capped positive-sense viral mRNA and transcription from the canine pol I regulatory sequence produces negative-sense, uncapped vRNA. Alternatively, in a unidirectional vector system of the invention, the gene or cDNA is located downstream of a pol I and a pol II promoter. The pol II promoter produces capped positive-sense viral mRNA and the pol I promoter produces uncapped positive-sense viral cRNA.

In another aspect, the invention provides a composition that comprises one, two, three, four, five, six, seven, eight, nine, ten, eleven, twelve, thirteen, fourteen, fifteen, sixteen, or seventeen vectors, wherein the vectors comprise one or more nucleic acids of the invention (e.g., a canine pol I regulatory sequence of the invention) operably linked to viral cDNA, e.g, influenza viral cDNA.

In certain embodiments, one, two, three, four, five, six, seven, eight, nine, ten, eleven, twelve, or more than twelve of the vectors of the invention are present in a single plasmid. In certain embodiments, at least one, two, three, four, five, six, seven, eight, nine, ten, eleven, or twelve of the vectors are present in a separate plasmid. In certain embodiments, each vector is on a separate plasmid.

In certain embodiments, the vectors of the invention are bi-directional expression vectors. A bi-directional expression vector of the invention typically includes a first promoter and a second promoter, wherein the first and second promoters are operably linked to alternative strands of the same double stranded cDNA encoding the viral nucleic acid including a segment of the influenza virus genome. Generally, at least one of these promoters is a canine RNA pol I promoter. Optionally, the bi-directional expression vector can include a polyadenylation signal and/or a termination sequence. For example, the polyadenylation signal and/or the termination sequence can be located flanking a segment of the influenza virus genome internal to the two promoters. One favorable polyadenylation signal is a SV40 polyadenylation signal.

In one embodiment, the invention comprises a bidirectional plasmid-based expression system and a unidirectional plasmid-based expression system, wherein viral cDNA is inserted between a canine pol I regulatory sequence (e.g., a pol I promoter) of the invention and termination sequences (inner transcription unit). This inner transcription unit is flanked by an RNA polymerase II (pol II) promoter and a polyadenylation site (outer transcription unit). In the unidirectional system, the pol I and pol II promoters are upstream of the cDNA and produce positive-sense uncapped cRNA (from the pol I promoter) and positive-sense capped mRNA (from the pol II promoter). The pol I promoter, pol I termination sequence, pol II promoter and polyadenylation signal in the unidirectional system may be referred to as comprising an "upstream-to-downstream orientation". In the bidirectional system, the pol I and pol II promoters are on opposite sides of the cDNA wherein an upstream pol II promoter produces positive-sense capped mRNA and a downstream pol I promoter produces negative-sense uncapped viral RNA (vRNA). These pol I-pol II systems start with the initiation of transcription of the two cellular RNA polymerase enzymes from their own promoters, presumably in different compartments of the nucleus. The pol I promoter and pol I termination sequence in the bidirectional system may be referred to as comprising a "downstream-to-upstream orientation" whereas the pol II promoter and polyadenylation signal in the bidirectional system may be referred to as comprising an "upstream-to-downstream orientation."

In other aspects, the invention disclosed herein includes compositions comprising an expression vector that comprises a polynucleotide sequence transcribable by canine RNA polymerase I. In certain embodiments, the polynucleotide produces an influenza vRNA or cRNA. In certain embodiments, the composition comprises a plurality of expression vectors that each comprises a polynucleotide sequence transcribable by canine RNA polymerase I. In certain embodiments, the polynucleotides produce a plurality of influenza vRNAs or cRNAs. In certain embodiments, the polynucleotides produce all eight influenza vRNAs or cRNAs In other aspects, the invention disclosed herein includes compositions comprising a plurality of expression vectors of the invention that, when introduced into a canine cell in the absence/presence of a helper virus, results in production of an influenza genome.

In certain embodiments, the compositions of the invention comprises a plurality of expression vectors that, when introduced into a canine cell in the absence/presence of a helper virus, results in production of an infectious influenza virus. In certain embodiments, the infectious influenza virus is a cold-sensitive influenza virus. In certain embodiments, the infectious influenza virus is an attenuated influenza virus. In certain embodiments, the infectious influenza virus is a temperature sensitive influenza virus. In certain embodiments, the infectious influenza virus is a cold-adapted influenza virus. In certain embodiments, the infectious influenza virus is an attenuated, temperature sensitive, cold-adapted influenza virus.

In certain embodiments, compositions of the invention comprise a vector comprising, from 5' to 3', a promoter operably linked to 5' non-coding influenza virus sequences linked to cDNA linked to 3' non-coding influenza virus sequences linked to a transcription termination sequence. In certain embodiments, one or more of the cDNAs in the vectors is in the sense orientation. In certain embodiments, one or more of the cDNAs in the vectors is in the anti-sense orientation.

In certain embodiments, the invention provides compositions which comprise a plurality of vectors, wherein the plurality of vectors comprise a vector comprising a canine regulatory sequence of the invention operably linked to an influenza virus polymerase acidic protein (PA) cDNA linked to a transcription termination sequence, a vector comprising a canine regulatory sequence operably linked to an influenza virus polymerase basic protein 1 (PB1) cDNA linked to a transcription termination sequence, a vector comprising a canine regulatory sequence operably linked to an influenza virus polymerase basic protein 2 (PB2) cDNA linked to a transcription termination sequence, a vector comprising a canine regulatory sequence operably linked to an influenza virus hemagglutinin (HA) cDNA linked to a transcription termination sequence, a vector comprising a canine regulatory sequence operably linked to an influenza virus nucleoprotein (NP) cDNA linked to a transcription termination sequence, a vector comprising a canine regulatory sequence operably linked to an influenza virus neuraminidase (NA) cDNA linked to a transcription termination sequence, a vector comprising a canine regulatory sequence operably linked to an influenza virus matrix protein cDNA linked to a transcription termination sequence, and a vector comprising a canine regulatory sequence operably linked to an influenza virus NS cDNA linked to a transcription termination sequence. In certain embodiments, the composition further comprises one or more expression vectors that express an mRNA encoding one or more influenza polypeptide selected from the group consisting of: PB2, PB1, PA, HA, NP, NA, matrix protein 1 (M1), matrix protein 2 (M2), and non-structural proteins 1 and 2 (NS1 and NS2). In one embodiment, the composition, when introduced into a canine cell, results in the production of infectious influenza virus. In certain embodiments, the infectious influenza virus is a cold-sensitive influenza virus. In certain embodiments, the infectious influenza virus is an attenuated influenza virus. In certain embodiments, the infectious influenza virus is a temperature sensitive influenza virus. In certain embodiments, the infectious influenza virus is a cold-adapted influenza virus. In certain embodiments, the infectious influenza virus is an attenuated, temperature sensitive, cold-adapted influenza virus.

In certain embodiments, the invention provides a composition which generates infectious influenza viruses from cloned viral cDNA, comprising a set of plasmids wherein each plasmid comprises cDNA encoding at least one viral genomic segment, and wherein viral cDNA corresponding to the viral genomic segment is inserted between a canine RNA polymerase I regulatory sequence of the invention and a regulatory element (e.g., a canine pol I termination sequence) for the synthesis of vRNA or cRNA with an exact 3' end, which results in expression of vRNA or cRNA.

In certain embodiments, the invention provides a composition which generates infectious influenza viruses from cloned viral cDNA, comprising a set of plasmids wherein each plasmid comprises cDNA encoding at least one viral genomic segment, and wherein viral cDNA corresponding to the viral genomic segment is inserted between a canine RNA polymerase I regulatory sequence of the invention and a regulatory element (e.g., a canine pol I termination sequence) for the synthesis of vRNA or cRNA with an exact 3' end, which results in expression of vRNA or cRNA, wherein the canine RNA polymerase I regulatory sequence, viral cDNA, and a regulatory element for the synthesis of vRNA or cRNA with an exact 3' end are in turn inserted between an RNA polymerase II (pol II) promoter and a polyadenylation signal, which results in expression of viral mRNA and a corresponding viral protein, wherein the expression of the full set of vRNAs or cRNAs and viral proteins results in assembly of an infectious influenza virus.

In certain embodiments, the regulatory element for the synthesis of vRNA or cRNA with an exact 3' end is an RNA polymerase I (pol I) termination sequence. As one skilled in the art is aware, efficient replication and transcription of influenza vRNA requires very specific sequences at the 5' and 3' ends of the vRNA. The skilled artisan can use a RNA polymerase I (pol I) termination sequence to ensure that the sequence of the 3' end of the RNA transcript made is defined to be the exact end desired for efficient replication and/or transcription of this genomic RNA. In certain embodiments, the regulatory element for the synthesis of vRNA or cRNA with an exact 3' end is a ribozyme sequence. In certain embodiments, the pol I promoter is proximal to the polyadenylation signal and the pol I termination sequence is proximal to the pol II promoter. In certain embodiments, the pol I promoter is proximal to the pol II promoter and the pol I termination sequence is proximal to the polyadenylation signal. In certain embodiments, the influenza virus is an influenza A virus. In certain embodiments, the influenza virus is an influenza B virus.

In another aspect, the invention provide a method for producing an influenza genomic RNA, comprising transcribing a nucleic acid of the invention, thereby producing an influenza genomic RNA. In certain embodiments, the influenza genomic RNA is transcribed in a cell-free system. In certain embodiments, the influenza genomic RNA is transcribed in a canine cell, e.g., an MDCK cell.

In one embodiment, the methods comprise comprising transcribing a plurality of nucleic acids of the invention, thereby producing a plurality of RNA molecules, e.g., a plurality of influenza genomic RNAs. In certain embodiments, one, two, three, four, five, six, seven, or eight influenza genomic RNAs are transcribed. In certain embodiments, a complete set of influenza genomic RNAs is transcribed. In certain embodiments, the influenza genomic RNA, when transcribed in a canine cell, e.g., an MDCK cell, in the presence of PA, PB1, PB2, and NP, expresses an influenza protein. In certain embodiments, the influenza protein is selected from the group consisting of PB2, PB1, PA, HA, NP, NA, M1, M2, NS1, and NS2. In certain embodiments, the complete set of influenza genomic RNAs, when transcribed in a canine cell, e.g., an MDCK cell, in the presence of PA, PB1, PB2, and NP, express an infectious influenza virus. In certain embodiments, the methods comprise introducing PA, PB1, PB2, and NP together with influenza genomic RNAs. In certain embodiments, PA, PB1, PB2, and NP are provided by a helper virus. In certain embodiments, the complete set of influenza genomic RNAs is from a cold-adapted, temperature-sensitive, attenuated influenza virus.

In one embodiment, a method of transcribing a vRNA segment of an influenza virus is provided, said method comprising the steps of 1) contacting a polynucleotide comprising a nucleic acid (or active fragment thereof) selected from the group consisting of: Nos: 1-28 with one or more influenza proteins PB1, PB2, NP, and PA, wherein said nucleic acid is operably linked to a cDNA molecule encoding said vRNA segment; and 2) isolating a transcribed vRNA segment. In one specific embodiment, helper virus is used in the method.

In one aspect, the invention provides a method of producing recombinant infectious recombinant viruses comprising a segmented RNA genome (e.g., an infectious influenza virus), comprising the steps of culturing canine host cells, e.g., MDCK cells, comprising one or more expression vectors of the invention that comprise viral cDNA corresponding to each gene in the viral genome and one or more expression vectors that express viral mRNA that encodes one or more viral polypeptides; and isolating an infectious virus population. In one embodiment, the infectious virus population is an influenza virus population. In one embodiment, the method further comprises the step of introducing the one or more expression vectors into the canine host cells prior to said step of culturing. In one embodiment, the method further comprises the step of making the one or more expression vectors prior to said step of introducing.

In one embodiment, a method of producing recombinant infectious recombinant viruses comprising a segmented RNA genome (e.g., an infectious influenza virus) is provided wherein the method comprises the steps of: a) inserting into one or more expression vectors of the invention viral cDNA corresponding to each gene in the viral genome; (b) introducing (e.g., by electroporation) said expression vectors and one or more expression vectors that express viral mRNA that encodes one or more viral polypeptides into a host cell (e.g., a canine cell) or a population of host cells; (c) incubating said host cells; and d), isolating an infectious virus population. In one embodiment, the infectious recombinant virus is influenza. In certain embodiments, the influenza virus is a cold-adapted, temperature-sensitive, attenuated influenza virus.

In one embodiment, a method of producing an infectious recombinant virus comprising a segmented RNA genome (e.g., an infectious influenza virus) is provided wherein the method comprises the steps of: a) inserting into one or more expression vectors of the invention a viral cDNA corresponding to each gene in the viral genome; (b) introducing (e.g., by electroporation) said expression vectors into a host cell (e.g., a canine cell) or a population of host cells; (c) incubating said host cells; and d), isolating an infectious virus population. In one embodiment, the infectious recombinant virus is influenza. In certain embodiments, the influenza virus is a cold-adapted, temperature-sensitive, attenuated influenza virus.

In one embodiment, the present invention provides for methods of generating infectious recombinant influenza virus in host cells using expression vectors of the invention to express the vRNA segments or corresponding cRNAs and influenza virus proteins, in particular PB1, PB2, PA and NA. In accordance with this embodiment, helper virus may or may not be used to generate the infectious recombinant influenza viruses.

In another embodiment, the invention provides a method for producing a recombinant influenza virus, comprising culturing canine cells comprising a plurality of nucleic acids comprising a canine RNA polymerase I regulatory sequence operably linked to one or more cDNAs encoding each influenza genomic RNA and one or more expression vectors that express viral mRNA that encodes one or more influenza polypeptides: PB2, PB1, PA, HA, NP, NA, M1, M2, NS1 and NS2; and isolating said recombinant influenza virus from the cells.

In certain embodiments, the methods comprise introducing into canine cells expression vectors which direct the expression in the cells of genomic or antigenomic viral RNA segments, a nucleoprotein, and an RNA-dependent polymerase, so that ribonucleoprotein complexes can be formed and viral particles can be assembled in the absence of helper virus; and (b) culturing the cells wherein viral particles are packaged and rescued. In certain embodiments, the recombinant negative strand virus is a non-segmented virus. In certain embodiments, the recombinant negative strand RNA virus is a segmented virus. In certain embodiments, the negative strand RNA virus is an influenza virus.

In certain embodiments, the methods comprise introducing into cultured canine cells expression vectors which direct the expression of the genomic or antigenomic RNA segments of a segmented negative strand RNA virus, a nucleoprotein, and an RNA dependent polymerase under conditions permitting formation of RNP complexes containing the genomic RNA segments of the virus and assembly of viral particles in the absence of helper virus; and culturing the cells wherein the viral particles are produced. In certain embodiments, the expression vectors direct expression of genomic RNA segments of the virus.

In certain embodiments, the canine cells used in the methods of the invention comprise one or more expression vectors that express one or more proteins selected from the nucleoprotein and the subunits of the RNA-dependent RNA polymerase. In certain embodiments, the expression vectors direct expression of one or more of the nucleoprotein and the subunits of said RNA-dependent RNA polymerase. In certain embodiments, the expression of the one or more viral proteins from the expression vectors is under the control of a regulatory sequence selected from the adenovirus 2 major late promoter linked to the spliced tripartite leader sequence of human adenovirus type 2 or the human cytomegalovirus immediate-early promoter, or a functional derivative of the regulatory sequence.

In certain embodiments, the virus is an influenza virus of type A, B or C. In certain embodiments, the virus is a reassortant virus having vRNA segments derived from more than one parent virus.

In certain embodiments, the methods of the invention comprise introducing a plurality of vectors of the invention, each of which incorporates a portion of an influenza virus into a population of host cells capable of supporting viral replication. The host cells can be cultured under conditions permissive for viral growth, and influenza viruses can be recovered. In some embodiments, the influenza viruses are attenuated viruses, cold adapted viruses and/or temperature sensitive viruses. For example, in certain embodiments, the vector-derived recombinant influenza viruses can be attenuated, cold adapted, temperature sensitive viruses, such as are suitable for administration as a live attenuated vaccine, e.g., in a intranasal vaccine formulation. In an exemplary embodiment, the viruses are produced by introducing a plurality of vectors incorporating all or part of an influenza B/Ann Arbor/1/66 virus genome, e.g., a ca B/Ann Arbor/1/66 virus genome.

In some embodiments, a plurality of vectors comprising cDNA encoding at least the 6 internal genome segments (e.g., genome segments encoding all influenza proteins except for HA and NA) of one influenza strain and cDNA encoding one or more genome segments (e.g., HA and NA vRNA segments) of a different influenza strain can be introduced into a population of host cells. For example, at least the 6 internal genome segments ("the backbone") of a selected attenuated, cold adapted and/or temperature sensitive influenza A or B strain, e.g., a ca, att, ts strain of B/Ann Arbor/1/66 or an artificially engineered ca, att, ts influenza A or B strain, can be introduced into a population of host cells along with one or more segments encoding immunogenic antigens derived from another virus strain. Typically the immunogenic surface antigens include either or both of the hemagglutinin (HA) and/or neuraminidase (NA) antigens. In embodiments where a single segment encoding an immunogenic surface antigen is introduced, the 7 complementary segments of the selected virus are also introduced into the host cells.

In certain embodiments, the expression vectors are transfected into the cells by electroporation. In certain embodiments, the expression vectors are introduced into cells by transfection into cells in the presence of a liposomal transfection reagent or by means of calcium phosphate precipitation. In certain embodiments, the expression vectors are plasmids. In certain embodiments, the expression vectors comprise a separate expression vector for expression of each genomic RNA segment of said virus or the corresponding coding RNAs. In certain embodiments, the expression of each genomic RNA segment or coding RNA is under the control of a promoter sequence derived from a canine Pol I promoter as described herein.

In certain embodiments, a plurality of plasmid vectors incorporating influenza virus genome segments are introduced into a population of host cells. For example, in certain embodiments, 8 plasmids, each of which incorporates a different genome segment can be utilized to introduce a complete influenza genome into the host cells. Alternatively, a greater number of plasmids, incorporating smaller genomic subsequences can be employed.

In another aspect, the present invention provides a method for generating in cultured cells infectious viral particles of a segmented negative-strand RNA virus having greater than 3 genomic vRNA segments, for example an influenza virus such as an influenza A virus, said method comprising: (a) introducing into a population of cells capable of supporting growth of said virus a first set of expression vectors capable of expressing in said cells genomic vRNA segments to provide the complete genomic vRNA segments of said virus; (b) introducing into said cells a second set of expression vectors capable of expressing mRNA encoding one or more polypeptides of said virus; and (c) culturing said cells whereby said viral particles are produced. In certain embodiments, the cells are canine cells. In certain embodiments, the cells are MDCK cells. In certain embodiments, the virus is influenza B virus. In certain embodiments, the first set of expression vectors is contained in 1-8 plasmids. In certain embodiments, the first set of expression vectors is contained in one plasmid. In certain embodiments, the second set of expression vectors is contained in 1-8 plasmids. In certain embodiments, the second set of expression vectors is contained in one plasmid. In certain embodiments, the first, second, or both sets of expression vectors are introduced by electroporation. In certain embodiments, the first set of expression vectors encode each vRNA segment of an influenza virus. In certain embodiments, the second set of expression vectors encode the mRNA of one or more influenza polypeptide. In certain embodiments, the first set or second set of expression vectors (or both sets) comprise a nucleic acid of the invention, for example, a canine regulatory sequence of the invention (e.g., canine pol I). In certain embodiments, the first set or second set of expression vectors (or both sets) encode a vRNA or mRNA of a second virus. For instance, a set of vectors comprises one or more vectors encoding the HA and/or NA mRNA and/or vRNA of a second influenza virus.

The present invention also provides a method for generating in cultured cells infectious viral particles of a segmented negative-strand RNA virus having greater than 3 genomic vRNA segments, for example an influenza virus such as an influenza A virus, said method comprising: (a) introducing into a population of cells capable of supporting growth of said virus a set of expression vectors capable of both expressing in said cells genomic vRNA segments to provide the complete genomic vRNA segments of said virus and capable of expressing mRNA encoding one or more polypeptides of said virus; (b) culturing said cells whereby said viral particles are produced. In certain embodiments, the cells are canine cells. In certain embodiments, the cells are MDCK cells. In certain embodiments, the virus is influenza B virus. In certain embodiments, the set of expression vectors is contained in 1-17 plasmids. In certain embodiments, the set of expression vectors is contained in 1-8 plasmid. In certain embodiments, the set of expression vectors is contained in 1-3 plasmids. In certain embodiments, the sets of expression vectors are introduced by electroporation. In certain embodiments, the set of expression vectors encode each vRNA segment of an influenza virus. In certain embodiments, the set of expression vectors encode the mRNA of one or more influenza polypeptide. In certain embodiments, the set of expression vectors encode each vRNA segment of an influenza virus and the mRNA of one or more influenza polypeptide. In certain embodiments, the set of expression vectors comprise a nucleic acid of the invention, for example, a canine regulatory sequence of the invention (e.g., canine pol I). In certain embodiments, the set of expression vectors encode a vRNA or mRNA of a second virus. For instance, the set of vectors comprises one or more vectors encoding the HA and/or NA mRNA and/or vRNA of a second influenza virus. In certain embodiments, the first set or second set of expression vectors (or both sets) encode a vRNA or mRNA of a second virus. For instance, a set of vectors comprises one or more vectors encoding the HA and/or NA mRNA and/or vRNA of a second influenza virus.

In certain embodiments, the methods further comprise amplifying viral particles produced by the canine cells by one or more further cellular infection steps employing cells which are the same or different from the canine cells. In certain embodiments, the methods further comprise isolating infectious viral particles. In certain embodiments, the methods further comprise a viral attenuation or killing step. In certain embodiments, the methods further comprise incorporating attenuated or killed viral particles into a vaccine composition.

In one embodiment, methods of producing viruses of the invention result in virus titers (24 hours, or 36, or 48 hours, or 3 days, or 4 days after introducing vectors of the invention into host cells) of at least $0.1 \times 10^3$ PFU/ml, or at least $0.5 \times 10^3$ PFU/ml, or at least $1.0 \times 10^3$ PFU/ml, or at least $2 \times 10^3$ PFU/ml, or at least $3 \times 10^3$ PFU/ml, or at least $4 \times 10^3$ PFU/ml, or at least $5 \times 10^3$ PFU/ml, or at least $6 \times 10^3$ PFU/ml, or at least $7 \times 10^3$ PFU/ml, or at least $8 \times 10^3$ PFU/ml, or at least $9 \times 10^3$ PFU/ml, or at least $1 \times 10^4$ PFU/ml, or at least $5 \times 10^4$ PFU/ml, or at least $1 \times 10^5$ PFU/ml, or at least $5 \times 10^5$ PFU/ml, or at least $1 \times 10^6$ PFU/ml, or at least $5 \times 10^6$ PFU/ml, or at least $1 \times 10^7$ PFU/ml, or in the range of $0.1$-$1 \times 10^3$ PFU/ml, or in the range of $1 \times 10^3$-$1 \times 10^4$ PFU/ml, or in the range of $1 \times 10^4$-$1 \times 10^5$ PFU/ml, or in the range of $1 \times 10^5$-$1 \times 10^6$ PFU/ml, or in the range of $1 \times 10^6$-$1 \times 10^7$ PFU/ml, or greater than $1 \times 10^7$ PFU/ml. Accordingly, the present invention provides methods for rescuing viruses, wherein the titer of the rescued virus at 24 to 36 hours or 2-3 days is at least $0.1 \times 10^3$ PFU/ml, or at least $0.5 \times 10^3$ PFU/ml, or at least $1.0 \times 10^3$ PFU/ml, or at least $2 \times 10^3$ PFU/ml, or at least $3 \times 10^3$ PFU/ml, or at least $4 \times 10^3$ PFU/ml, or at least $5 \times 10^3$ PFU/ml, or at least $6 \times 10^3$ PFU/ml, or at least $7 \times 10^3$ PFU/ml, or at least $8 \times 10^3$ PFU/ml, or at least $9 \times 10^3$ PFU/ml, or at least $1 \times 10^4$ PFU/ml, or at least $5 \times 10^4$ PFU/ml, or at least $1 \times 10^5$ PFU/ml, or at least $5 \times 10^5$ PFU/ml, or at least $1 \times 10^6$ PFU/ml, or at least $5 \times 10^6$ PFU/ml, or at least $1 \times 10^7$ PFU/ml or in the range of $0.1$-$1 \times 10^3$ PFU/ml, or in the range of $1 \times 10^3$-$1 \times 10^4$ PFU/ml, or in the range of $1 \times 10^4$-$1 \times 10^5$ PFU/ml, or in the range of $1 \times 10^5$-$1 \times 10^6$ PFU/ml, or in the range of $1 \times 10^6$-$1 \times 10^7$ PFU/ml, or greater than $1 \times 10^7$ PFU/ml.

In some embodiments, the influenza viruses correspond to an influenza B virus. In some embodiments, the influenza viruses correspond to an influenza A virus. In certain embodiments, the methods include recovering recombinant and/or reassortant influenza viruses capable of eliciting an immune response upon administration, e.g., intranasal administration, to a subject. In some embodiments, the viruses are inactivated prior to administration, in other embodiments, live-attenuated viruses are administered. Recombinant and reassortant influenza A and influenza B viruses produced according to the methods of the invention are also a feature of the invention. In certain embodiments, the viruses include an attenuated influenza virus, a cold adapted influenza virus, a temperature sensitive influenza virus, or a virus with any combination of these desirable properties. In one embodiment, the influenza virus incorporates an influenza B/Ann Arbor/1/66 strain virus, e.g., a cold adapted, temperature sensitive, attenuated strain of B/Ann Arbor/1/66. In another embodiment, the influenza virus incorporates an influenza A/Ann Arbor/6/60 strain virus, e.g., a cold adapted, temperature sensitive, attenuated strain of A/Ann Arbor/6/60.

Optionally, reassortant viruses are produced by introducing vectors encoding the six internal vRNAs of a viral strain selected for its favorable properties regarding vaccine production, in combination with vectors encoding vRNA segments of the surface antigens (HA and NA) of a selected, e.g., pathogenic strain. For example, the HA segment can be favorably selected from a pathogenically relevant H1, H3 or B strain, as is routinely performed for vaccine production. Similarly, the HA segment can be selected from an emerging pathogenic strain such as an H2 strain (e.g., H2N2), an H5 strain (e.g., H5N1) or an H7 strain (e.g., H7N7). Alternatively, the seven complementary gene segments of the first strain are introduced in combination with either the HA or NA encoding segment. In certain embodiments, the internal gene segments are derived from the influenza B/Ann Arbor/1/66 or the A/Ann Arbor/6/60 strain. In addition, an influenza virus may be produced (e.g., an H5N1, H9N2, H7N7, or HxNy (where x=1-9 and y=1-15) that comprises a modified HA gene. For example, the HA gene may be modified by removal of the polybasic cleavage site.

In another aspect, the invention provides a host cell comprising a nucleic acid or expression vector of the invention. In certain embodiments, the cell is a canine cell. In certain embodiments, the canine cell is a kidney cell. In certain embodiments, the canine kidney cell is an MDCK cell. In other embodiments, the cell is selected from the group consisting of Vero cells, Per.C6 cells, BHK cells, PCK cells, MDCK cells, MDBK cells, 293 cells (e.g., 293T cells), and COS cells. In some embodiments, co-cultures of a mixture of at least two of these cell lines, e.g., a combination of COS and MDCK cells or a combination of 293T and MDCK cells, constitute the population of host cells.

The host cells comprising the influenza vectors of the invention can be grown in culture under conditions permissive for replication and assembly of viruses. Typically, host cells incorporating the influenza plasmids can be cultured at a temperature below 37° C., preferably at a temperature equal to, or less than, 35° C. In certain embodiments, the cells are cultured at a temperature between 32° C. and 35° C. In some embodiments, the cells are cultured at a temperature between about 32° C. and 34° C., e.g., at about 33° C. Following culture for a suitable period of time to permit replication of the virus to particular titer, recombinant viruses can be recovered. Optionally, the recovered viruses can be inactivated.

In yet another aspect, the invention provides a method for engineering an influenza virus such that its growth is restricted to particular cell types including, but not limited to, MRC-5, WI-38, FRhL-2, PerC6, 293, NIH 3T3, CEF, CEK, DF-1, Vero, MDCK, Mvl Lu, human epithelial cells and SF9 cell types. In one embodiment, growth is restricted such that an influenza virus can not grow in a human primary cell (e.g., PerC6). In another embodiment, growth is restricted such that an influenza virus can not grow in an human epithelial cell. One skilled in the art will recognize that the growth restriction phenotype may be combined with one or more additional phenotypes such as cold adapted, temperature sensitive, attenuated, etc. It will also be recognized that a mutation responsible for a growth restricted phenotype may also contribute and/or be responsible for additional phenotypes such as those listed above.

In another aspect, the invention provides novel methods for rescuing recombinant or reassortant influenza A or influenza B viruses (i.e., wild type and variant strains of influenza A and/or influenza viruses) from MDCK cells in culture. In certain embodiments, a plurality of vectors incorporating an influenza virus genome whose transcription is controlled by a canine regulatory sequence of the invention is electroporated into a population of MDCK cells. The cells can be grown under conditions permissive for viral replication, e.g., in the case of cold adapted, attenuated, temperature sensitive virus strains, the MDCK cells are grown at a temperature below 37° C., preferably at a temperature equal to, or less than, 35° C.

Typically, the cells are cultured at a temperature between 32° C. and 35° C. In some embodiments, the cells are cultured at a temperature between about 32° C. and 34° C., e.g., at about 33° C. Optionally (e.g., for vaccine production), the MDCK cells are grown in serum free medium without any animal-derived products.

In some embodiments of the methods described above, influenza viruses can be recovered following culture of the host cells incorporating the influenza genome plasmids. In some embodiments, the recovered viruses are recombinant viruses. In some embodiments, the viruses are reassortant influenza viruses having genetic contributions from more than one parental strain of virus. Optionally, the recovered recombinant or reassortant viruses are further amplified by passage in cultured cells or in hens' eggs.

Optionally, the recovered viruses can be inactivated. In some embodiments, the recovered viruses comprise an influenza vaccine. For example, the recovered influenza vaccine can be a reassortant influenza viruses (e.g., 6:2 or 7:1 reassortant viruses) having an HA and/or NA antigen derived from a selected strain of influenza A or influenza B. In one embodiment, the HA or NA antigen is modified. In certain favorable embodiments, the reassortant influenza viruses have an attenuated phenotype. Optionally, the reassortant viruses are cold adapted and/or temperature sensitive, e.g., an attenuated, cold adapted or temperature sensitive influenza A or B virus. Such influenza viruses are useful, for example, as live attenuated vaccines for the prophylactic production of an immune response specific for a selected, e.g., pathogenic influenza strain. Influenza viruses, e.g., attenuated reassortant viruses, produced according to the methods of the invention are an additional feature of the invention.

In another aspect, the invention relates to methods for producing a recombinant influenza virus vaccine comprising introducing a plurality of vectors incorporating an influenza virus genome whose transcription is controlled by a canine regulatory sequence of the invention (e.g., a canine RNA pol I promoter) into a population of host cells capable of supporting replication of influenza virus, culturing the host cells at a temperature less than or equal to 35° C., and recovering an influenza virus capable of eliciting an immune response upon administration to a subject. The vaccines can comprise either influenza A or influenza B strain viruses.

In some embodiments, the influenza vaccine viruses include an attenuated influenza virus, a cold adapted influenza virus, or a temperature sensitive influenza virus. In certain embodiments, the viruses possess a combination of these desirable properties. In an embodiment, the influenza virus contains an influenza A/Ann Arbor/6/60 strain virus. In another embodiment, the influenza virus incorporates an influenza B/Ann Arbor/1/66 strain virus. Alternatively, the vaccine includes artificially engineered influenza A or influenza B viruses incorporating at least one substituted amino acid which influences the characteristic biological properties of ca A/Ann Arbor/6/60 or ca/B/Ann Arbor/1/66, such as a unique amino acid of these strains.

In one embodiment, a vaccine comprising a population of recombinant viruses (or viruses derived therefrom) produced by the methods of the invention is provided. In a specific embodiment, the vaccine comprises a live virus produced by the methods. In another specific embodiment, the vaccine comprises a killed or inactivated virus produced by the methods. In another specific embodiment, the vaccine comprises an immunogenic composition prepared from a live, killed or inactivated virus produced by the methods. In another specific embodiment, the vaccine comprises an immunogenic composition prepared from a live attenuated, cold adapted, temperature-sensitive influenza virus produced by the method. In another specific embodiment, the vaccine comprises a live attenuated, cold adapted, temperature-sensitive influenza virus produced by the method or a virus derived therefrom.

5. BRIEF DESCRIPTION OF THE FIGURES

FIG. 1 presents growth curves of wt and ca B strain (B/Beijing/243/97) in both PerC6 and MDCK cells; virus titer for each time point was determined by TCID50 assay.

Figure 2:
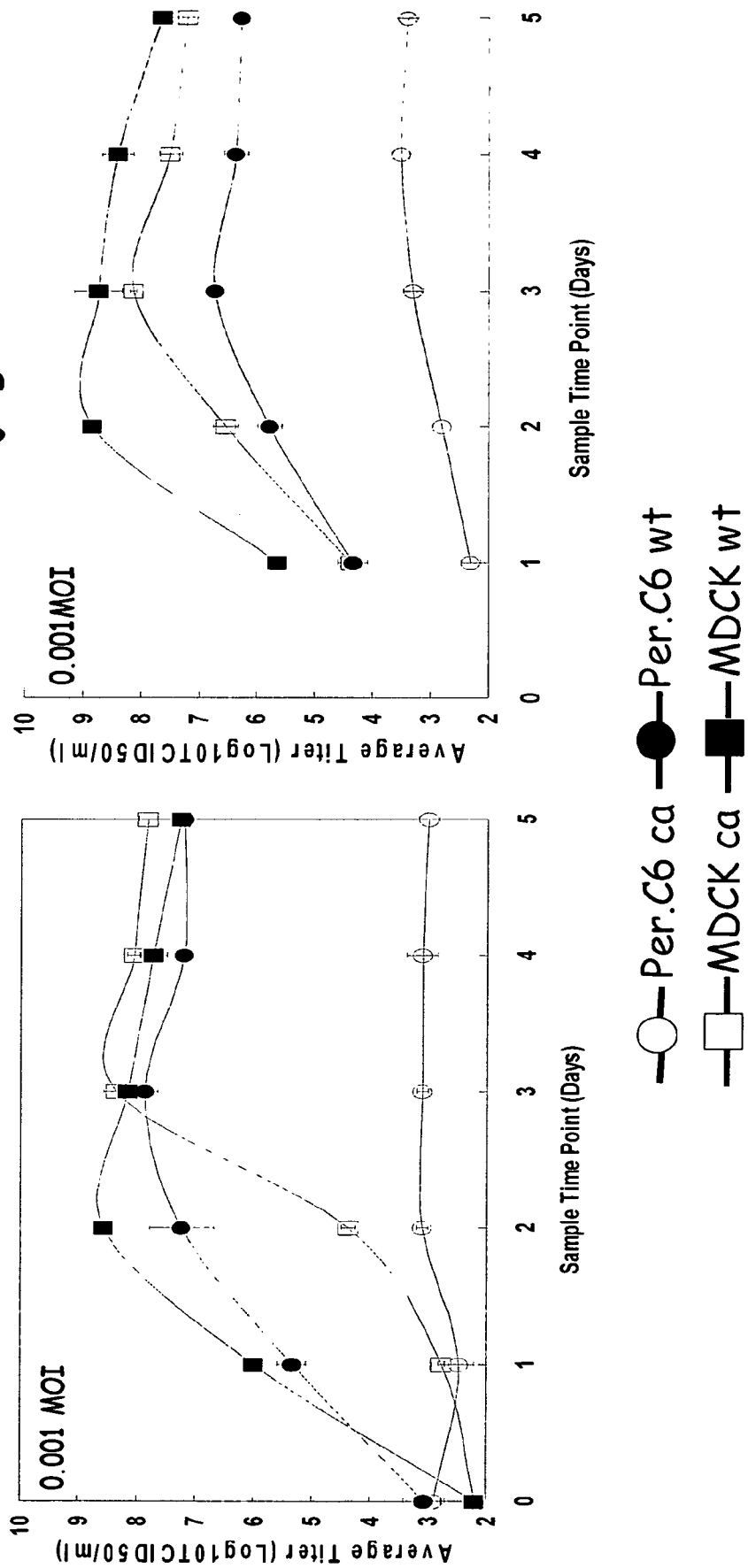

FIG. 2 presents growth curves of wt and ca A strains (A/Sydney/05/97 and A/Beijing/262/95) in both PerC6 and MDCK cells; virus titer for each time point was determined by TCID50 assay.

Figure 3:
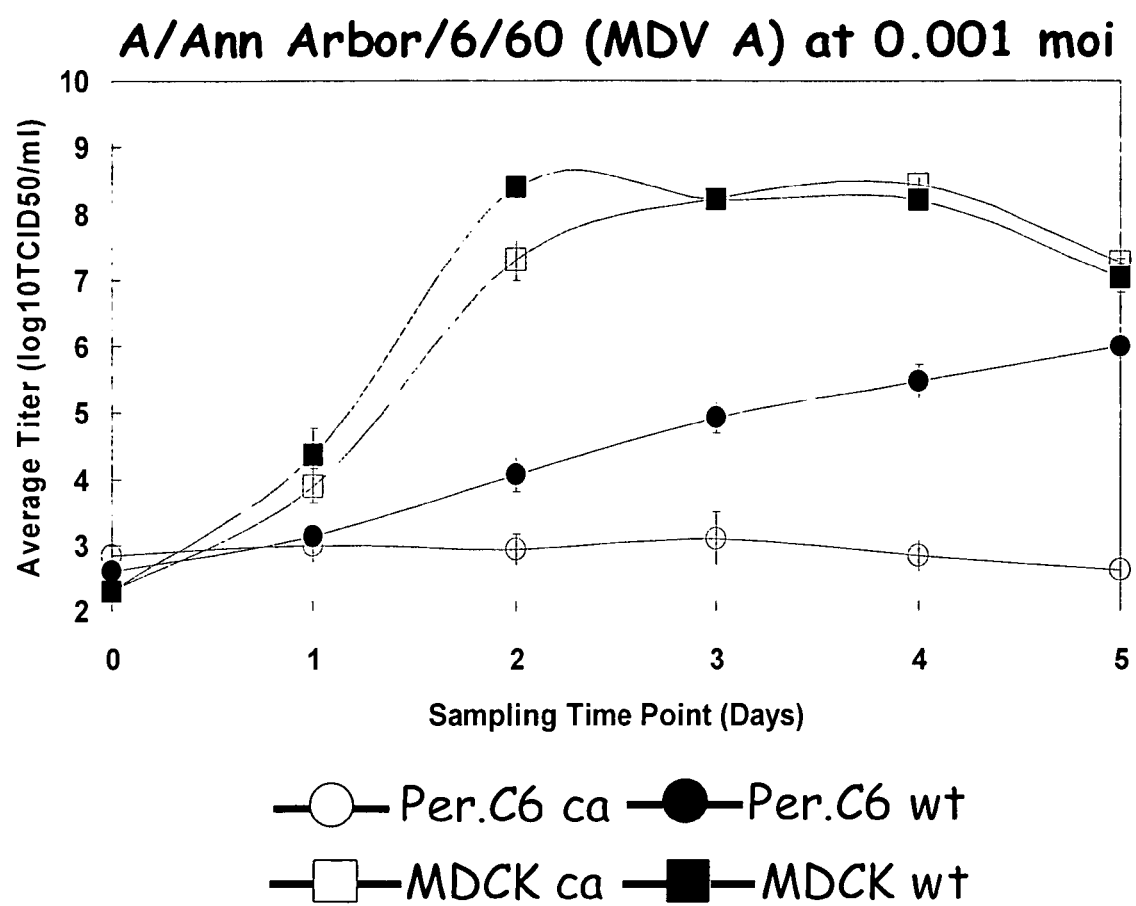

FIG. 3 presents growth curves of wt and ca A strain (A/Ann Arbor/6/60) in both PerC6 and MDCK cells; virus titer for each time point was determined by TCID50 assay.

Figure 4:
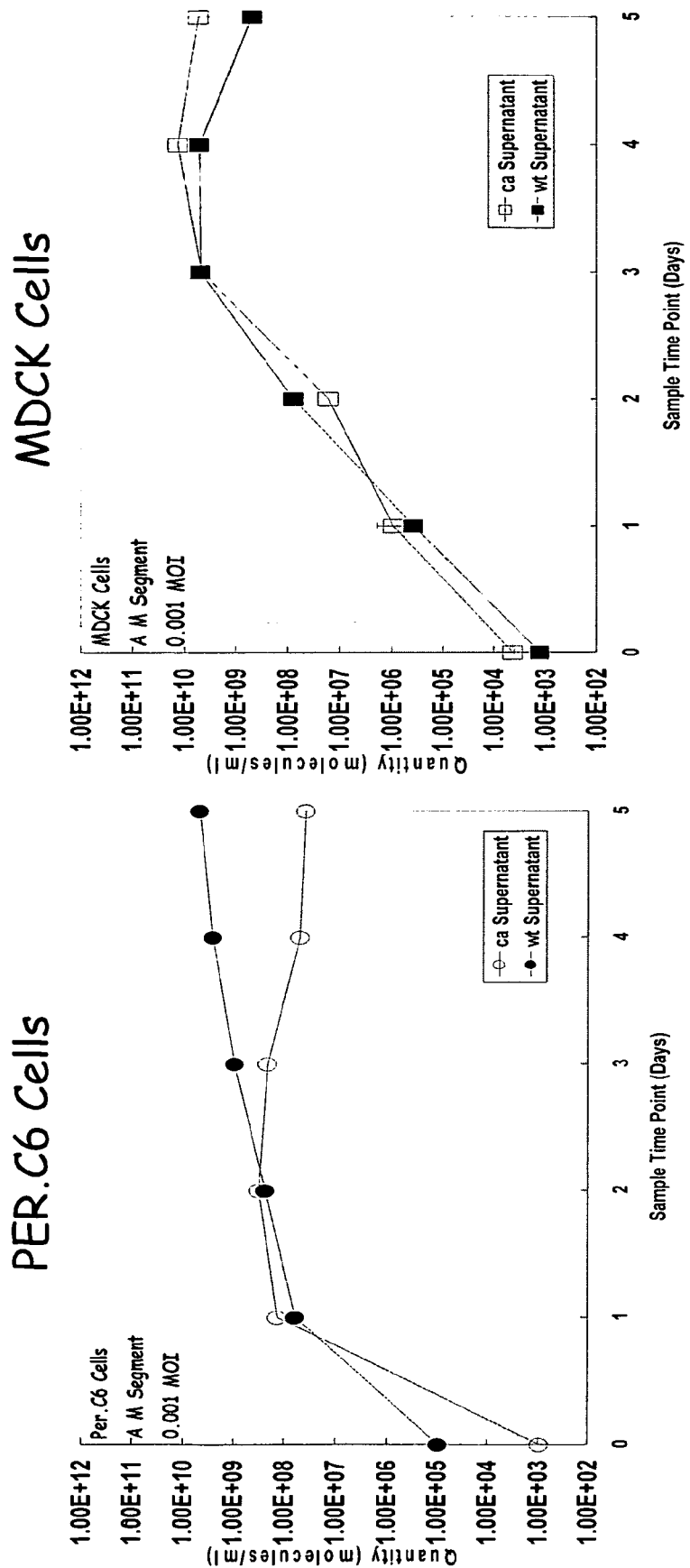

FIG. 4 presents real time analysis of viral RNA of A/Sydney in PerC6 and MDCK cells, using Taqman® (Roche Molecular Systems; Palo Alto, Calif.) probes specific for the M segment of the viral RNA.

FIG. 5 presents growth curves of ca A/Vietnam/1203/2004 (H5N1) in MDCK cells; virus titer for each time point was determined by TCID50 assay.

Figure 6:
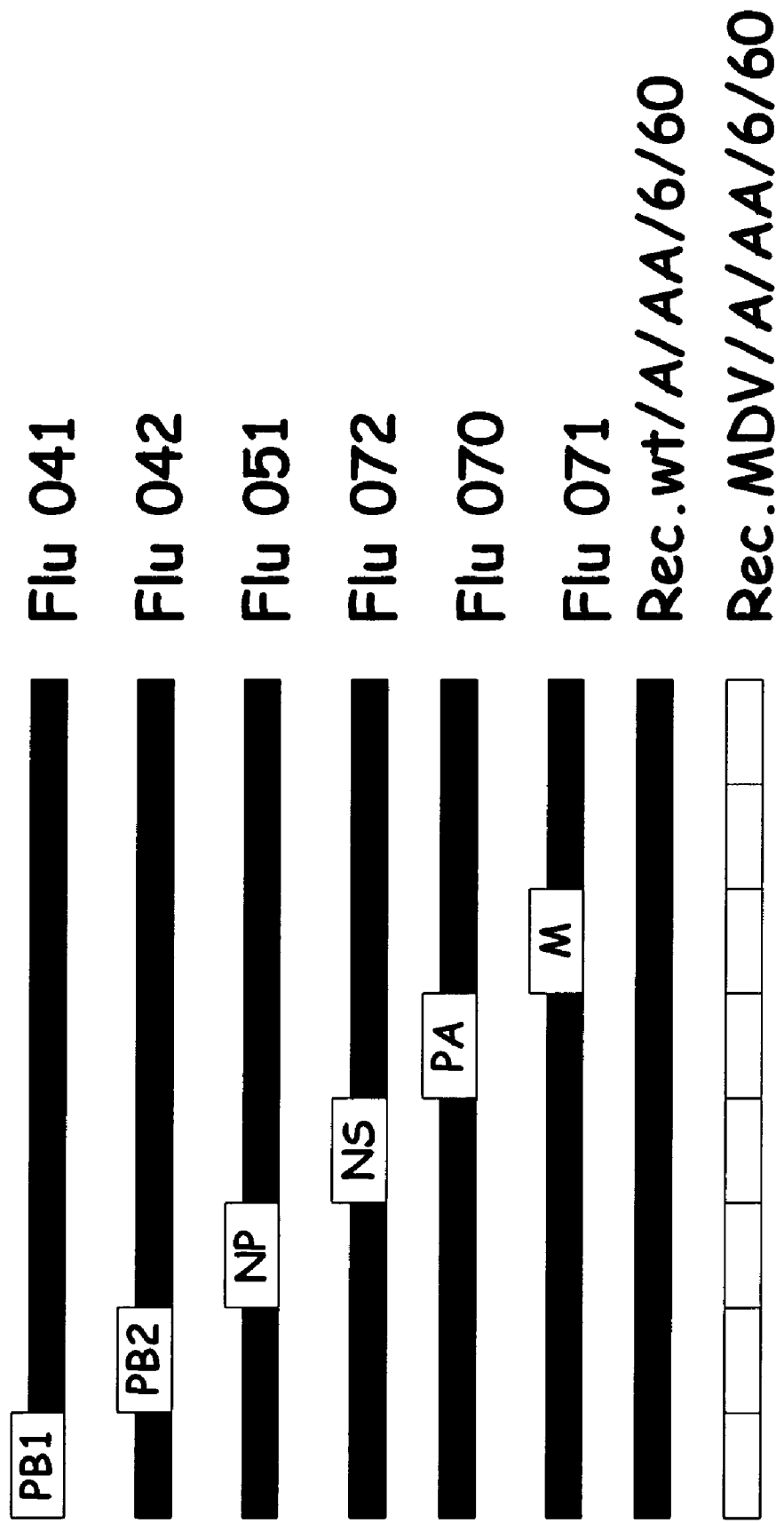

FIG. 6 presents a diagram showing rescue of each influenza gene segment as a 7:1 reassortant generated by the eight-plasmid rescue technique.

FIG. 7 presents growth curves of each of the 7:1 reassortants in PerC6 cells; virus titer for each time point was determined by TCID50 assay.

Figure 8:
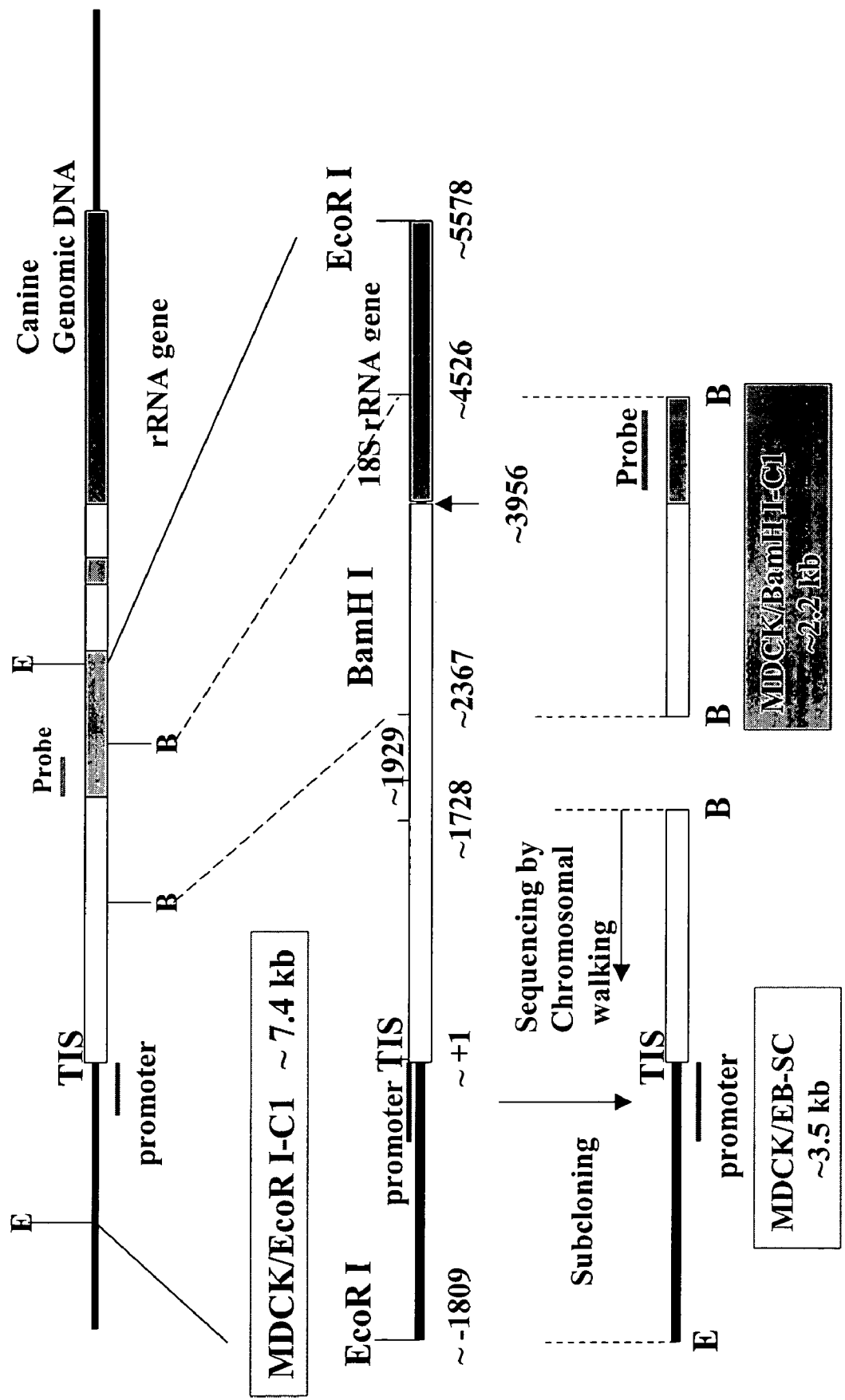

FIG. 8 presents a restriction map of an Eco RI fragment that comprises a canine RNA pol I regulatory sequence.

FIGS. 9A, 9B and 9C presents the nucleotide sequence (SEQ ID NO:1) of an approximately 3.5 kB nucleic acid cloned from canine genomic DNA, which encodes at least a portion of the 18s rRNA gene, beginning at nucleotide 1809 (+1) in the sequence presented.

Figure 10:
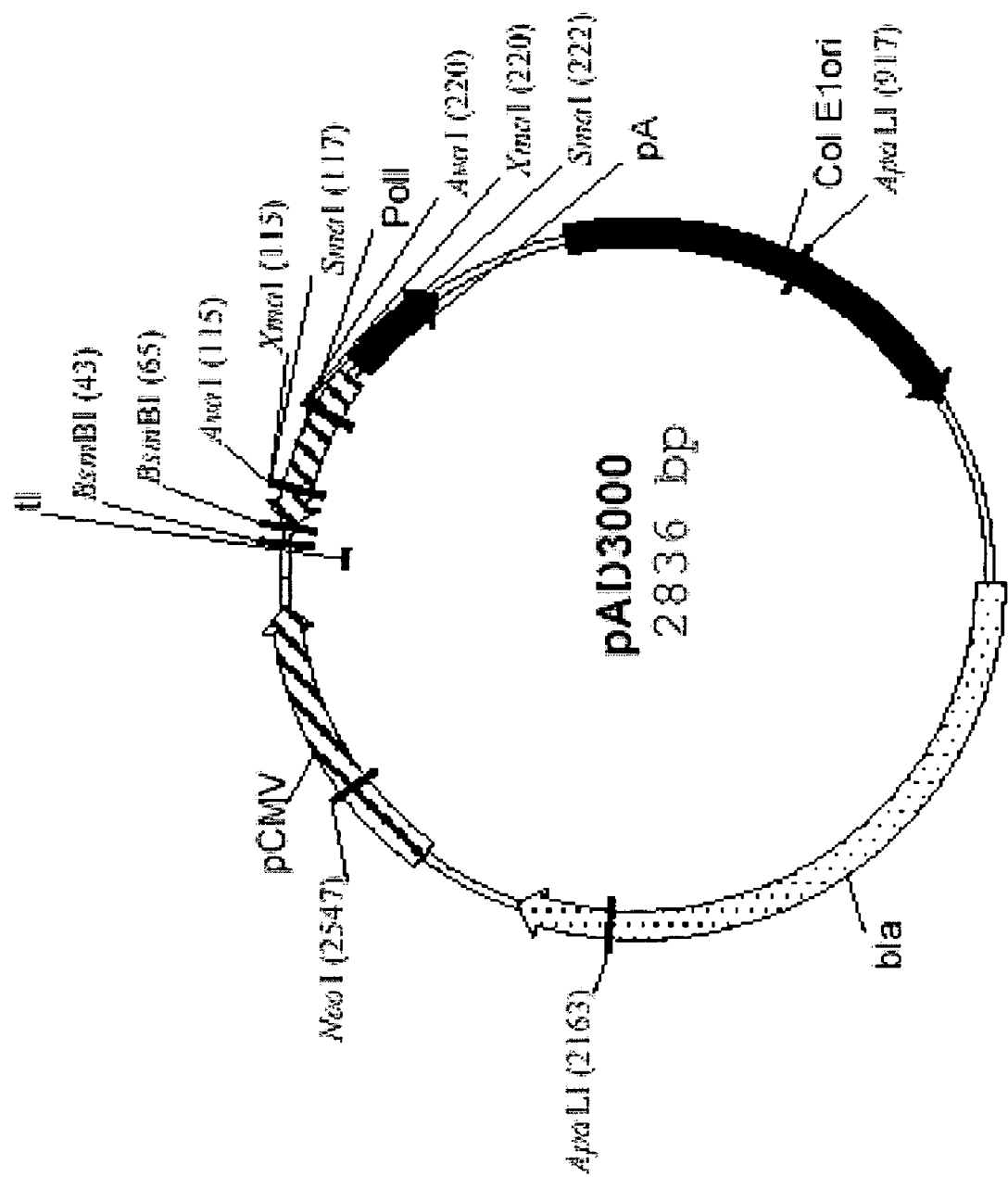

FIG. 10 presents a map of plasmid pAD3000, which can be readily adapted to make an expression vector of the invention.

Figure 11:
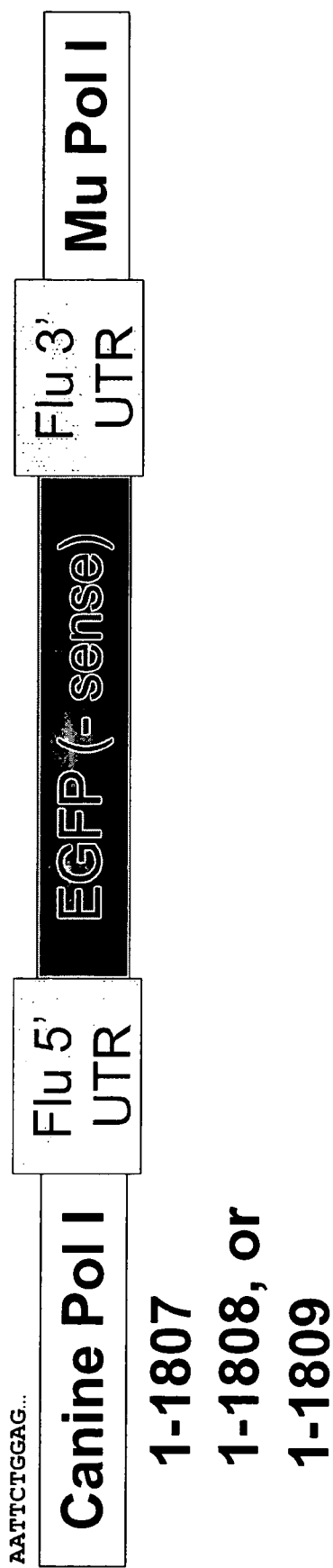

FIG. 11 presents a diagram of the MDCK pol I promoter constructs used in the mini-genome assay.

Figure 12:
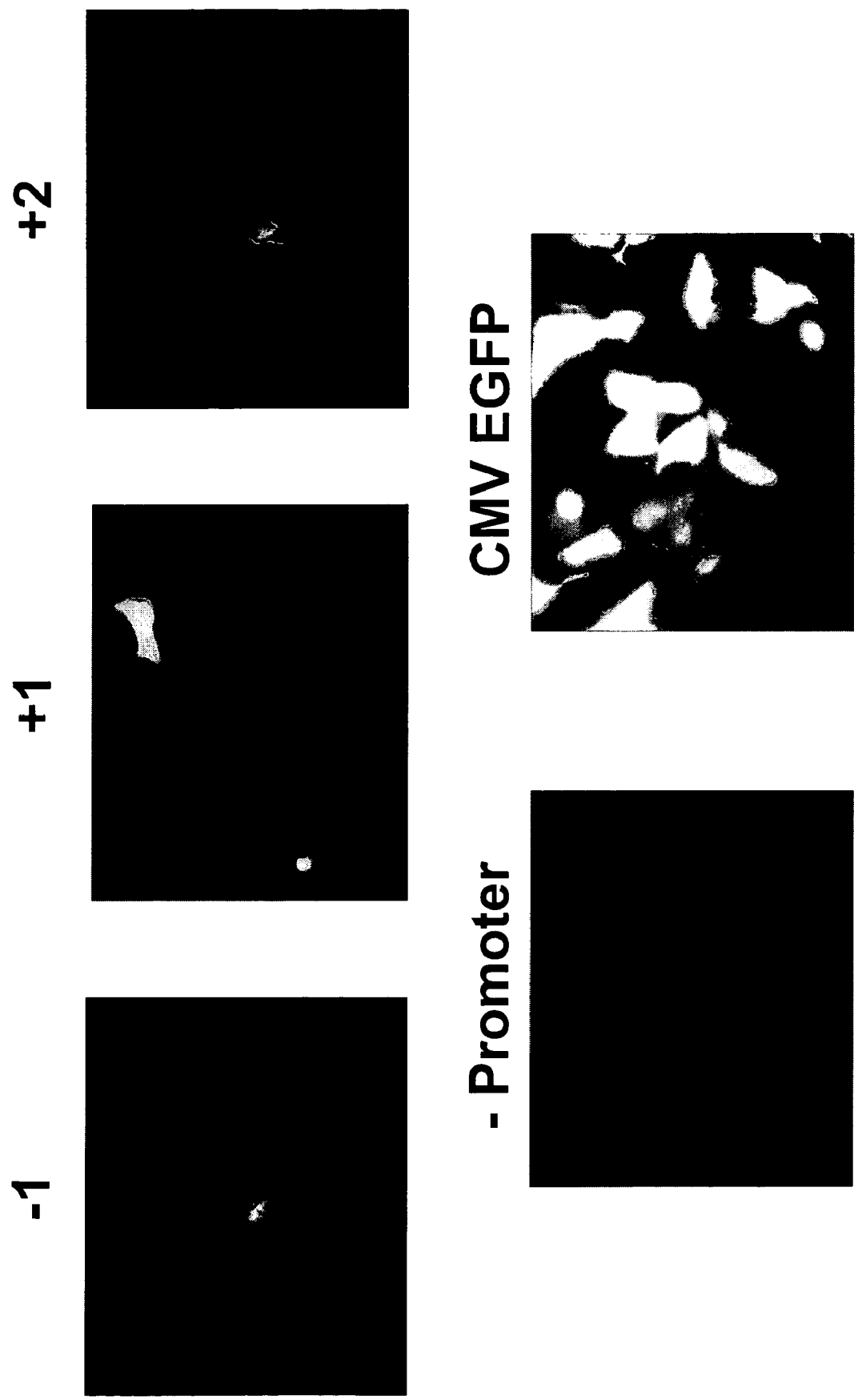

FIG. 12 presents the results of a mini-genome assay. The EGFP signal generated from the −1, +1 and +2 MDCK pol I promoter constructs are shown in the top left, middle and right panels, respectively. A minus promoter control shows only background fluorescence (bottom left). As a positive control cells were also transfected with a CMV-EGFP construct (bottom right).

FIG. 13 presents the sequence of plasmid expression vector pAD4000 (SEQ ID NO:29) that comprises a 469 bp fragment (bases 1-469 in pAD4000) from the MDCK EcoRI-BamHI subclone (bases 1340-1808 of SEQ ID NO:1). Note: The 469 bp fragment is shown in reverse complement orientation and the linker sequence is underlined and bolded.

FIG. 14 indicated the annealing positions of the primers used to conduct the RT-PCR reactions on the RNA of rescued virus.

FIG. 15 presents the sequences of primers used to conduct the RT-PCR reactions on the RNA of rescued virus.

FIGS. 16A-B show the partial sequences of NS and PB1 segments and the positions of the introduced silent mutations.

6. DETAILED DESCRIPTION OF THE INVENTION

Plasmid rescue of influenza virus generally comprises introduction of expression vectors for expressing viral proteins and transcribing viral genomic RNA into suitable host cells. Transcription of the viral genomic RNA is generally performed with an RNA polymerase I enzyme, as these enzymes produce transcripts with ends suitable for use as viral genomes. Thus, RNA pol I promoters and other regulatory elements are used to initiate transcription of genomic RNAs during plasmid rescue. Unfortunately, RNA pol I promoters are highly species-specific. That is, RNA pol I from one species may or may not bind efficiently to an RNA pol I promoter from an unrelated species. Accordingly, the availability of RNA pol I promoters limits the cells in which plasmid rescue can be performed. Prior to the present invention, plasmid rescue was not possible in canine cells. For the first time, plasmid rescue in canine cells is possible based on the disclosure of the present invention as follows.

Accordingly, in a first aspect, isolated nucleic acids of the invention comprising a canine RNA polymerase I regulatory sequences are provided. In certain embodiments, the regulatory sequence is a promoter. In one embodiment, the regulatory sequence is a canine pol I promoter sequence. In another embodiment, the regulatory sequence is operably linked to cloned viral cDNA. In yet another embodiment, the cloned viral cDNA encodes viral RNA of a negative or positive strand virus or the corresponding cRNA. In one specific embodiment, the cloned viral cDNA encodes genomic viral RNA (or the corresponding cRNA) of an influenza virus.

In one specific embodiment, isolated nucleic acids of the invention comprise a canine RNA polymerase I regulatory sequence and a transcriptional termination sequence. In certain embodiments, transcriptional termination sequences is a pol I termination sequence. In certain embodiments, transcriptional termination sequences is a human, monkey, or canine pol I termination sequence.

In certain embodiments, nucleic acids of the invention comprise a polynucleotide sequence or a functionally active fragment thereof, e.g., a canine RNA pol I regulatory sequence, that binds a human, primate, mouse or canine pol I polypeptide and is at least 100% or about 99%, 98%, 97%, 96%, 95%, 90%, 85%, 80%, 75%, 70%, or 65% identical to one or more nucleotide sequences selected from the group consisting of: SEQ ID Nos: 1-28. In one embodiment, the polynucleotide sequence or functionally active fragment thereof further retains the ability to initiate transcription, in the presence of appropriate polypeptides (e.g., human, primate, mouse or canine pol I polypeptides), of a second polynucleotide sequence operatively linked to the nucleotide sequence. In one embodiment, "functionally active fragments" of the nucleic acids set forth in SEQ ID Nos: 1-28 retain one or more functional activities described herein of the full length sequences of SEQ ID Nos: 1-28. For instance, functionally active fragments of the regulatory sequence set forth as SEQ ID NO:1 are provided whereby the regulatory sequence fragment is operably linked to a nucleic acid to be transcribed and, in the presence of suitable proteins in vitro or in vivo, is transcribed. In a particular embodiment, nucleic acids of the invention comprise a polynucleotide sequence of the nucleic acid set forth in SEQ ID NO: 26.

In certain embodiments, nucleic acids of the invention comprise a polynucleotide sequence or a fragment thereof, e.g., a canine RNA pol I regulatory sequence, that binds a human, primate, mouse or canine pol I polypeptide and/or is 100% or at least or about 99%, 98%, 97%, 96%, 95%, 90%, 85%, 80%, 75%, 70%, or 65% identical to one or more nucleotide sequences selected from the group consisting of: SEQ ID Nos: 1-28. In one embodiment, the polynucleotide sequence or fragment thereof further retains the ability to initiate transcription, in the presence of appropriate polypeptides (e.g., human, primate, mouse or canine pol I polypeptides), of a second polynucleotide sequence operatively linked to the nucleotide sequence.

In certain aspects, the present invention provides an isolated nucleic acid that comprises a canine RNA pol I promoter. Preferably, the canine RNA pol I promoter is operably linked to a nucleic acid to be transcribed, such as, e.g., an influenza genomic RNA. Introduction of the nucleic acid into a canine cell results in transcription of the influenza genomic RNA, and, in the presence of suitable influenza proteins, the RNA transcript can be packed into an infectious influenza virus. In one embodiment, isolated nucleic acids are provided which comprise a canine RNA regulatory sequence of the invention (e.g., a canine RNA pol I promoter), wherein the regulatory sequence is operably linked to a nucleic acid to be transcribed and, in the presence of suitable proteins in vitro or in vivo, is transcribed. In one embodiment, the nucleic acid operably linked to said regulatory sequence is an influenza vRNA segment.

In another aspect, the invention provides vectors and methods for producing recombinant influenza viruses in canine cell culture entirely from cloned viral DNA. For example, influenza viruses can be produced by introducing a plurality of vectors comprising cloned cDNA encoding each viral genome segment under the transcriptional control of a canine RNA regulatory sequence (e.g., a canine pol I promoter) of the invention into canine host cells, culturing the canine cells, and isolating the recombinant influenza viruses produced from the cell culture. When vectors encoding an influenza virus genome are thus introduced (e.g., by electroporation) into canine cells, recombinant viruses suitable as vaccines can be recovered by standard purification procedures. Using the vector system and methods of the invention, reassortant viruses incorporating the six internal gene segments of a strain selected for its desirable properties with respect to vaccine production, and the immunogenic HA and NA segments from a selected, e.g., pathogenic strain, can be rapidly and efficiently produced in tissue culture. Thus, the system and methods described herein are useful for the rapid production in canine cell culture of recombinant and reassortant influenza A and B viruses, including viruses suitable for use as vaccines, including live attenuated vaccines. Vaccines prepared according to methods of the invention may be delivered intranasally or intramuscularly.

Typically, a single Master Donor Virus (MDV) strain is selected for each of the A and B subtypes. In the case of a live attenuated vaccine, the Master Donor Virus strain is typically chosen for its favorable properties, e.g., temperature sensitivity, cold adaptation and/or attenuation, relative to vaccine production. For example, exemplary Master Donor Strains include such temperature sensitive, attenuated and cold adapted strains of A/Ann Arbor/6/60 and B/Ann Arbor/1/66, respectively.

For example, a selected master donor type A virus (MDV-A), or master donor type B virus (MDV-B), can be produced from a plurality of cloned viral cDNAs constituting the viral genome. In an exemplary embodiment, recombinant viruses are produced from eight cloned viral cDNAs. Eight viral cDNAs representing either the selected MDV-A or MDV-B sequences of PB2, PB 1, PA, NP, HA, NA, M and NS are cloned into an expression vector, e.g., a bi-directional expression vector such as a plasmid (e.g., pAD3000 or pAD4000), such that the viral genomic RNA can be transcribed from a canine RNA polymerase I (pol I) promoter from one strand and the viral mRNAs can be synthesized from an RNA polymerase II (pol II) promoter from the other strand. Optionally, any gene segment can be modified, including the HA segment (e.g., to remove the multi-basic cleavage site).

Infectious recombinant MDV-A or MDV-B virus is then recovered following transfection of plasmids bearing the eight viral cDNAs into appropriate host cells, e.g., MDCK cells. Using the plasmids and methods described herein, the invention is useful, e.g., for generating 6:2 reassortant influenza vaccines by co-transfection of the 6 internal genes (PB1, PB2, PA, NP, M and NS) of the selected virus (e.g., MDV-A, MDV-B, PR8) together with the HA and NA derived from different corresponding type (A or B) influenza viruses. For example, the HA segment is favorably selected from a pathogenically relevant H1, H3 or B strain, as is routinely performed for vaccine production. Similarly, the HA segment can be selected from a strain with emerging relevance as a pathogenic strain such as an H2 strain (e.g., H2N2), an H5 strain (e.g., H5N1) or an H7 strain (e.g., H7N7). Reassortants incorporating seven genome segments of the MDV and either the HA or NA gene of a selected strain (7:1 reassortants) can also be produced. In addition, this system is useful for determining the molecular basis of phenotypic characteristics, e.g., the attenuated (att), cold adapted (ca), and temperature sensitive (ts) phenotypes, relevant to vaccine production.

6.1 Definitions

Unless defined otherwise, all scientific and technical terms are understood to have the same meaning as commonly used in the art to which they pertain. For the purpose of the present invention the following terms are defined below.

The terms "nucleic acid," "polynucleotide," "polynucleotide sequence" and "nucleic acid sequence" refer to single-stranded or double-stranded deoxyribonucleotide or ribonucleotide polymers, or chimeras or analogues thereof. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention encompasses complementary sequences, in addition to the sequence explicitly indicated.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "Tissue specific" promoter or enhancer is one which regulates transcription in a specific tissue type or cell type, or types.

A "promoter" or "promoter sequence" is a DNA regulatory region capable of initiating transcription of a nucleic acid sequence to which it is operably attached, when appropriate transcription-related enzymes, e.g., RNA polymerase, are present under conditions, e.g., culture or physiological conditions, whereby the enzymes are functional. A promoter can be present upstream or downstream from the nucleic acid sequence whose transcription it initiates. A promoter sequence which is located upstream of a cDNA is bounded at its 3' terminus by a transcription initiation site and extends upstream (5' direction) to include the minimum number of bases or elements necessary to initiate transcription at levels detectable above background. A promoter sequence which is located downstream of a cDNA (to express a (−)RNA) is bounded at its 5' terminus by a transcription initiation site and extends downstream (3' direction) to include the minimum number of bases or elements necessary to initiate transcription at levels detectable above background. The bidirectional system of the invention includes both upstream and downstream promoters; the unidirectional system includes only upstream promoters. Within or adjacent to the promoter sequence will be found a transcription initiation site (conveniently defined for example, by mapping with nuclease S1), and can also include protein binding domains (consensus sequences) that promote, regulate, enhance, or are otherwise responsible for the binding of RNA polymerase.

A "canine RNA polymerase I regulatory sequence" or "canine RNA polymerase I regulatory element" (or functionally active fragments thereof), as used herein, refers to a nucleic acid sequence that is capable of increasing transcription of a nucleic acid sequence to which it is operably attached, when canine RNA polymerase I and, optionally, associated transcription factors, are present under conditions, e.g., culture or physiological conditions, whereby the enzymes are functional. Examples of canine RNA polymerase I regulatory sequences include a canine RNA polymerase I promoter, which increases transcription of a nucleic acid operably linked thereto above background, and a canine RNA polymerase I enhancer, which increases transcription of a nucleic acid operably linked to a canine RNA polymerase I promoter above the level observed in the absence of a canine RNA polymerase I enhancer. One test for identifying a canine RNA polymerase I regulatory element is to introduce the putative canine RNA polymerase I regulatory element, operably linked to a nucleic acid of interest, into a suitable canine cell, e.g., an MDCK cell, and detect transcription of the nucleic acid of interest using a conventional assay, e.g., a Northern blot. Comparison of transcription levels of the nucleic acid in the presence and absence of the putative canine RNA polymerase I regulatory element permits the skilled artisan to determine whether the nucleic acid element is a canine RNA polymerase I regulatory element.

The term "vector" refers to a nucleic acid, e.g., a plasmid, viral vector, recombinant nucleic acid or cDNA that can be used to introduce heterologous nucleic acid sequences into a cell. A vector of the invention typically will comprise a regulatory sequence of the invention. The vectors can be autonomously replicating or not autonomously replicating. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating. Most commonly, the vectors of the present invention are plasmids.

An "expression vector" is a vector, such as a plasmid, which is capable of promoting expression, e.g., transcription, of a nucleic acid incorporated therein. An expression vector of the invention typically will comprise a regulatory sequence of the invention. The expression vectors can be autonomously replicating or not autonomously replicating. Typically, the nucleic acid to be expressed is "operably linked" to a promoter and/or enhancer, and is subject to transcription regulatory control by the promoter and/or enhancer.

A "bi-directional expression vector" is typically characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs. Alternatively, the bi-directional expression vector can be an ambisense vector, in which the viral mRNA and viral genomic RNA (as a cRNA) are expressed from the same strand.

In the context of the invention, the term "isolated" refers to a biological material, such as a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids.

The term "recombinant" indicates that the material (e.g., a nucleic acid or protein) has been artificially or synthetically (non-naturally) altered by human intervention. The alteration can be performed on the material within, or removed from, its natural environment or state. Specifically, when referring to a virus, e.g., an influenza virus, the virus is recombinant when it is produced by the expression of a recombinant nucleic acid.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuraminidase, from a second parental virus. A 6:2 reassortant includes 6 genomic segments, most commonly the 6 internal genes from a first parental virus, and two complementary segments, e.g., hemagglutinin and neuraminidase, from a different parental virus.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation" and "transduction." In the context of the invention a variety of methods can be employed to introduce nucleic acids into prokaryotic cells, including electroporation, calcium phosphate precipitation, lipid mediated transfection (lipofection), etc.

The term "host cell" means a cell which can or has taken up a nucleic acid, such as a vector, and supports the replication and/or expression of the nucleic acid, and optionally production of one or more encoded products including a polypeptide and/or a virus. Host cells can be prokaryotic cells such as E. coli, or eukaryotic cells such as yeast, insect, amphibian, avian or mammalian cells, including human cells. Exemplary host cells in the context of the invention include Vero (African green monkey kidney) cells, Per.C6 cells (human embryonic retinal cells), BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells). The term host cell encompasses combinations or mixtures of cells including, e.g., mixed cultures of different cell types or cell lines (e.g., Vero and CEK cells). A co-cultivation of electroporated SF Vero cells is described for example in PCT/US04/42669 filed Dec. 22, 2004, which is incorporated by reference in their entirety.

The expression "artificially engineered" is used herein to indicate that the virus, viral nucleic acid or virally encoded product, e.g., a polypeptide, a vaccine, comprises at least one mutation introduced by recombinant methods, e.g., site directed mutagenesis, PCR mutagenesis, etc. The expression "artificially engineered" when referring to a virus (or viral component or product) comprising one or more nucleotide mutations and/or amino acid substitutions indicates that the viral genome or genome segment encoding the virus (or viral component or product) is not derived from naturally occurring sources, such as a naturally occurring or previously existing laboratory strain of virus produced by non-recombinant methods (such as progressive passage at 25° C.), e.g., a wild type or cold adapted A/Ann Arbor/6/60 or B/Ann Arbor/1/66strain.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, *J. Mol. Biol.* 215:403-10 (with special reference to the published default setting, i.e., parameters w=4, t=17) and Altschul et al., 1997, *Nucleic Acids Res.*, 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids can be found in Tijssen, 1993, *Laboratory Techniques in Biochemistry and Molecular Biology-Hybridization with Nucleic Acid Probes*, part 1, chapter 2, "Overview of principles of hybridization and the strategy of nucleic acid probe assays", Elsevier, NY; Sambrook et al., 2001, *Molecular Cloning: A Laboratory Manual*, Cold Spring Harbor Laboratory, $3^{rd}$ ed., NY; and Ausubel et al., eds., Current Edition, *Current Protocols in Molecular Biology*, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

One example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

The term "about," as used herein, unless otherwise indicated, refers to a value that is no more than 10% above or below the value being modified by the term. For example, the term "about 5 μg/kg" means a range of from 4.5 μg/kg to 5.5 μg/kg. As another example, "about 1 hour" means a range of from 48 minutes to 72 minutes.

The term "encode," as used herein, refers to the property of a nucleic acid, e.g., deoxyribonucleic acid, to transcribe a complementary nucleic acid, including a nucleic acid that can be translated into a polypeptide. For example, a deoxyribonucleic acid can encode an RNA that is transcribed from the deoxyribonucleic acid. Similarly, the deoxyribonucleic acid can encode a polypeptide translated from an RNA transcribed from the deoxyribonucleic acid.

6.2 Nucleic Acids Comprising Canine RNA Pol I Regulatory Elements

In one embodiment, isolated nucleic acids are provided which comprise a canine RNA regulatory sequence of the invention (e.g., a canine RNA pol I promoter). The regulatory sequence can, for example, be operably linked to a nucleic acid to be transcribed and can, in the presence of suitable proteins in vitro or in vivo, be transcribed. In one embodiment, the nucleic acid operably linked to said regulatory sequence is an influenza vRNA segment.

In certain aspects, the present invention provides an isolated nucleic acid that comprises a canine RNA pol I promoter. Preferably, the canine RNA pol I promoter is operably linked to a nucleic acid to be transcribed, such as, e.g., an influenza genomic RNA. Introduction of the nucleic acid into a canine cell can result in transcription of the influenza genomic RNA, and, in the presence of suitable influenza proteins, the RNA transcript or transcripts can be packed into an influenza virus, e.g., an infectious influenza virus.

In certain embodiments, nucleic acid acids of the invention comprise a canine RNA pol I regulatory sequence or fragment thereof that binds a human, primate, mouse or canine pol I polypeptide and is at least or about 99%, 98%, 97%, 96%, 95%, 94%, 93%, 92%, 91%, 90%,89%,88%,87%,86%,85%, 84%,83%,82%,81%,80% 79%,78%,77%,76%,75%, 74%, 73%, 72%, 71%, 70%, 69%, 68%, 67%, 66%, 65%, 64%, 63%, 62%, 61%, or 60% identical to one or more nucleotide sequences selected from the group consisting of: SEQ ID Nos: 1-28. In one embodiment, the RNA pol I regulatory sequence or fragment thereof further retains the ability to initiate transcription of a gene operatively linked to the nucleotide sequence. In certain embodiments, nucleic acid acids of the invention comprise a polynucleotide sequence that is at least or about 99%, 98%, 97%, 96%, 95%, 94%, 93%, 92%, 91%,90%,89%,88%,87%,86%,85%,84%,83%,82%,81%, 80% 79%,78%,77%, 76%,75%,74%,73%,72%,71%,70%, 69%,68%,67%,66%,65%,64%,63%,62%,61%, or 60% identical to the sequence of SEQ ID NO:29.

Furthermore, the nucleic acids of the invention also encompass derivative versions of nucleic acids comprising a canine RNA pol I promoter. Such derivatives can be made by any method known by one of skill in the art without limitation from the canine RNA pol I regulatory sequences identified hereinafter. For example, derivatives can be made by site-specific mutagenesis, including substitution, insertion, or deletion of one, two, three, five, ten or more nucleotides, of the nucleic acids. Alternatively, derivatives can be made by random mutagenesis. One method for randomly mutagenizing a nucleic acid comprises amplifying the nucleic acid in a PCR reaction in the presence of 0.1 mM $MnCl_2$ and unbalanced nucleotide concentrations. These conditions increase the misincorporation rate of the polymerase used in the PCR reaction and result in random mutagenesis of the amplified nucleic acid. Preferably, the derivative nucleic acids retain the ability to initiate transcription of a gene operatively linked to the nucleotide sequence. In certain embodiments, embodiments, the nucleic acid of the invention comprises at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 325, 350, 375, 400, 425, 450, 475, 500, 550, 600, 650, 700, 750, 800, 850, 900, 950, or 1000 consecutive nucleotides of one or more nucleotide sequences selected from the group consisting of: SEQ ID Nos: 1-28. Preferably, the nucleic acid comprises a sequence that can initiate transcription of a gene operatively linked to the nucleotide sequence in canine cells, and thus is a functional derivative. In one embodiment, the nucleic acid comprises a sequence that can bind canine pol I polypeptides and initiate (in vitro or in vivo) transcription of an influenza vRNA in canine cells. In one embodiment, an isolated nucleic acid sequence is provided that comprises at least 250, or at least 350, or at least 450 contiguous nucleotides of the sequence set forth as SEQ ID NO:26, wherein said nucleic acid sequence when operably linked to cDNA encoding an influenza vRNA and introduced into an MDCK cell is capable of directing the expressing of said influenza vRNA. In another embodiment, an isolated nucleic acid sequence is provided which comprises a polynucleotide having at least 80% identity to the nucleotide sequence set forth as SEQ ID NO:26, wherein said nucleic acid sequence when operably linked to cDNA encoding an influenza vRNA and introduced into an MDCK cell is capable of directing the expressing of said influenza vRNA. In another embodiment, an isolated nucleic acid sequence is provided which comprises a polynucleotide that hybridizes under stringent hybridization conditions to a nucleic acid selected from the group consisting of: SEQ ID Nos 1-26, wherein said nucleic acid sequence when operably linked to cDNA encoding an influenza vRNA and introduced into an MDCK cell is capable of directing the expressing of said influenza vRNA. In certain embodiments, nucleic acids of the invention comprises at least about 400, 500, 550, 600, 650, 700, 750, 800, 850, 900, 950, 1000, 2000, or 3000 consecutive nucleotides of SEQ ID No.29.

In certain embodiments, a nucleic acid sequence of the invention comprises, or alternatively consists of nucleotides −469 to −1 (in relation to the first nucleotide transcribed from the promoter, also known as the +1 nucleotide) of the sequence presented as SEQ ID NO:1, or a functional derivative thereof. In other embodiments, a nucleic acid sequence of the invention comprises, or alternatively consists of nucleotides −250 to −1 (in relation to the first nucleotide transcribed from the promoter, also known as the +1 nucleotide) of the sequence presented as SEQ ID NO:1, or a functional derivative thereof. The +1 nucleotide for the 18S ribosomal RNA expressed from the canine pol I regulatory sequence found in SEQ ID NO:1 is the nucleotide at position 1809 of SEQ ID NO:1. In one embodiment, a nucleic acid is provided which comprises nucleotides 1-469 of SEQ ID NO:26, the complement thereof, the reverse complement thereof, or a functionally active fragment thereof.

The present invention also provides functionally active fragments of SEQ ID NO:1 (a subsequence of the nucleotide sequence present in the deposited clone A.T.C.C. Accession No. PTA-7540). Accordingly, the present invention further provides polynucleotides having one or more nucleic acid residues deleted from the amino terminus of the nucleotide sequence of SEQ ID NO:1. N-terminal deletions of SEQ ID NO:1 can be described by the general formula m−3537, where m is an integer from 2 to 3512, where m corresponds to the position of the nucleotide identified in SEQ ID NO:1, or the nucleotide sequence present in the deposited clone (A.T.C.C. Accession No. PTA-7540). The present invention also provides polynucleotides having one or more nucleic acid residues deleted from the carboy terminus of the nucleotide sequence of SEQ ID NO:1. C-terminal deletions of SEQ ID NO:1 can be described by the general formula 1−n, where n is an integer from 2 to 3512, where n corresponds to the position of nucleotide identified in SEQ ID NO:1, or the nucleotide sequence present in the deposited clone (A.T.C.C. Accession No. PTA-7540).

The present invention also provides functionally active fragments of SEQ ID NO: 26 (a subsequence of the nucleotide sequence present in the deposited clone A.T.C.C. Accession No. PTA-7540). Accordingly, the present invention further provides polynucleotides having one or more nucleic acid residues deleted from the amino terminus of the nucleotide sequence of SEQ ID NO:26. N-terminal deletions of SEQ ID NO: 26 can be described by the general formula m−469, where m is an integer from 2 to 450, where m corresponds to the position of the nucleic acid residue identified in SEQ ID NO:26. The present invention also provides polynucleotides having one or more nucleic acid residues deleted from the carboy terminus of the nucleotide sequence of SEQ ID NO:26. C-terminal deletions of SEQ ID NO: 26 can be described by the general formula 1−n, where n is an integer from 2 to 450, where n corresponds to the position of nucleic acid residue identified in SEQ ID NO:26.

In certain embodiments, the canine pol I regulatory sequence of the invention comprises, or alternatively consists of an isolated nucleic acid (or the complement sequence thereof) that hybridizes under stringent hybridization conditions to a nucleic acid comprising a nucleic acid selected from the group consisting of: SEQ ID Nos: 1-28 and can initiate transcription of a gene operatively linked to the regulatory sequence in canine cells.

In one embodiment, the canine pol I regulatory sequence of the invention comprises a nucleic acid sequence that can bind a canine RNA pol I polypeptide and, in one embodiment, initiate transcription of a gene operatively linked to the nucleotide sequence in canine cells. In one embodiment, the nucleic acid comprises a sequence that can bind a eukaryotic pol I polypeptide and initiate (in vitro or in vivo) transcription of an influenza vRNA. In certain embodiments, binding of canine RNA pol I polypeptide to a canine pol I regulatory sequence is assayed with a nuclease protection assay. In certain embodiments, binding of canine RNA pol I polypeptide to a canine pol I regulatory sequence is assayed with a BIACORE system for assessing protein interactions (Biacore International AG, Uppsala, Sweden).

In certain embodiments, the nucleic acid comprises a sequence that binds canine RNA pol I. In certain embodiments, the sequence binds canine RNA pol I with greater affinity than an RNA polymerase selected from the group consisting of: a primate RNA pol I, a human pol I, and a mouse pol 1. In certain embodiments, the sequence binds canine RNA pol I with greater affinity than canine RNA pol II. In certain embodiments, the sequence binds canine RNA pol I with greater affinity than canine RNA pol III. In certain embodiments, binding to a canine pol I regulatory sequence is assayed with a BIACORE system for assessing protein interactions (Biacore International AG, Uppsala, Sweden).

In certain embodiments, the canine RNA pol I promoter comprises, or alternatively consists of, the following nucleotide sequence:

ATTCCCGGTGAGGCTGCCTCTGC-
CGCGCGTGGCCCTCCACCTCCCCTGGCCCGAG
CCGGGGTTGGGGACGGCGGTAG-
GCACGGGGCGGTCCTGAGGGCCGCGGGGGAC
GGCCTCCGCACGGTGCCTGCCTCCG-
GAGAACTTTGATGATTTTTCAAAGTCTCCT CCCG-
GAGATCACTGGCTTGGCGGCGTGGCG-
GCGTGGCGGCGTGGCGGCGTGGCG
GCGTGGCGGCGTGGCGTCTCCACCGAC-
CGCGTATCGCCCCTCCTCCCCTCCCCCC
CCCCCCCCGTTCCCTGGGTCGACCAGAT-
AGCCCTGGGGGCTCCGTGGGGTGGGGG
TGGGGGGGCGCCGTGGGGCAG-

GTTTTGGGGACAGTTGGCCGTGTCACGGTCCCG
GGAGGTCGCGGTGACCTGTGGCTGGTC-
CCCGCCGGCAGGCGCGGTTATTTTCTTG
CCCGAGATGAACATTTGTTGCCAGGTAGGT (SEQ ID NO: 26), which is a subsequence of the nucleotide sequence present in the deposited clone A.T.C.C. Accession No. PTA-7540.

In certain embodiments, the canine RNA pol I promoter comprises, or alternatively consists of, the following nucleotide sequence:

(SEQ ID NO:2)
TTGATGATTTTTCAAAGTCCTCCCGGAGATCACTGGCTTGGCGGCGTGGC

GGCGTGGCGGCGTGGCGGCGTGGCGGCGTGGCGGCGTGGCGTCTCCACCG

ACCCGTATCGCCCCTCCTCCCCTCCCCCCCCCCCCCGTTCCCTGGGTCG

ACCAGATAGCCCTGGGGGCTCCGTGGGGTGGGGTGGGGGGCGCCGTGG

GGCAGGTTTTGGGGACAGTTGGCCGTGTCACGGTCCCGGGAGGTCGCGGT

GACCTGTGGCTGGTCCCCGCCGGCAGGCGCGGTTATTTTCTTGCCCGAGA

TGAACATTTTTGTTGCCAGGTAGGTGCTGACA.

In certain embodiments, the canine RNA pol I promoter comprises, or alternatively consists of, the following nucleotide sequence:

(SEQ ID NO:20)
TTGATGATTTTTCAAAGTCTCCTCCCGGAGATCACTGGCTTGGCGGCGTG

GCGGCGTGGCGGCGTGGCGGCGTGGCGGCGTGGCGGCGTGGCGTCTCCAC

CGACCGCGTATCGCCCCTCCTCCCCTCCCCCCCCCCCCCCGTTCCCTGGG

TCGACCAGATAGCCCTGGGGGCTCCGTGGGGTGGGGTGGGGGGCGCCG

TGGGGCAGGTTTTGGGGACAGTTGGCCGTGTCACGGTCCCGGGAGGTCGC

GGTGACCTGTGGCTGGTCCCCGCCGGCAGGCGCGGTTATTTTCTTGCCCG

AGATGAACATTTTTGTTGCCAGGTAGGTGCTGACA.

In certain embodiments, the canine RNA pol I promoter comprises, or alternatively consists of, the following nucleotide sequence:

(SEQ ID NO:3)
GGGCTCCGTGGGGTGGGGTGGGGGGCGCCGTGGGGCAGGTTTTGGGGA

CAGTTGGCCGTGTCACGGTCCCGGGAGGTCGCGGTGACCTGTGGCTGGTC

CCCGCCGGCAGGCGCGGTTATTTTCTTGCCCGAGATGAACATTTTTGTT

GCCAGGTAGGTGCTGACA.

In certain embodiments, the canine RNA pol I promoter comprises, or alternatively consists of, the following nucleotide sequences (SEQ ID NO:4)
GCCGTGGGGCAGGTTTTGGGGACAGTTGGCCGTGTCACGGTCCCGGGAGG

TCGCGGTGACCTGTGGCTGGTCCCCGCCGGCAGGCGCGGTTATTTTCTTG

CCCGAGATGAACATTTTTGTTGCCAGGTAGGTGCTGACA.

In certain embodiments, the canine RNA pol I promoter comprises, or alternatively consists of, the following nucleotide sequence:

(SEQ ID NO:5)
TGGCCGTGTCACGGTCCCGGGAGGTCGCGGTGACCTGTGGCTGGTCCCCG

CCGGCAGGCGCGGTTATTTTCTTGCCCGAGATGAACATTTTTGTTGCCA

GGTAGGTGCTGACA.

In certain embodiments, the canine RNA pol I promoter comprises, or alternatively consists of, the following nucleotide sequence:

(SEQ ID NO:6)
GTGACCTGTGGCTGGTCCCCGCCGGCAGGCGCGGTTATTTTCTTGCCCGA

GATGAACATTTTTGTTGCCAGGTAGGTGCTGACA.

In certain embodiments, the canine RNA pol I promoter comprises, or alternatively consists of, the following nucleotide sequence:

(SEQ ID NO:7)
AGGCGCGGTTATTTTCTTGCCCGAGATGAACATTTTTGTTGCCAGGTAG

GTGCTGACA.

In certain embodiments, the canine RNA pol I promoter comprises, or alternatively consists of, the following nucleotide sequence:

(SEQ ID NO:8)
TTGATGATTTTTCAAAGTCCTCCCGGAGATCACTGGCTTGGCGGCGTGGC

GGCGTGGCGGCGTGGCGGCGTGGCGGCGTGGCGGCGTGGCGTCTCCACCG

ACCCGTATCGCCCCTCCTCCCCTCCCCCCCCCCCCCCGTTCCCTGGGTCG

ACCAGATAGCCCTG.

In certain embodiments, the canine RNA pol I promoter comprises, or alternatively consists of, the following nucleotide sequence:

(SEQ ID NO:21)
TTGATGATTTTTCAAAGTCTCCTCCCGGAGATCACTGGCTTGGCGGCGTG

GCGGCGTGGCGGCGTGGCGGCGTGGCGGCGTGGCGGCGTGGCGTCTCCAC

CGACCGCGTATCGCCCCTCCTCCCCTCCCCCCCCCCCCCCGTTCCCTGGG

TCGACCAGATAGCCCTG.

In certain embodiments, the canine RNA pol I promoter comprises, or alternatively consists of, the following nucleotide sequence:

(SEQ ID NO:9)
TTGATGATTTTTCAAAGTCCTCCCGGAGATCACTGGCTTGGCGGCGTGGC

GGCGTGGCGGCGTGGCGGCGTGGCGGCGTGGCGGCGTGGCGTCTCCACCG

ACCCGTATCGCCCCTCCTCCCCTCCCCCCCCCCCCCC.

In certain embodiments, the canine RNA pol I promoter comprises, or alternatively consists of, the following nucleotide sequence:

(SEQ ID NO:22)
TTGATGATTTTTCAAAGTCTCCTCCCGGAGATCACTGGCTTGGCGGCGTG

GCGGCGTGGCGGCGTGGCGGCGTGGCGGCGTGGCGGCGTGGCGTCTCCAC

CGACCGCGTATCGCCCCTCCTCCCCTCCCCCCCCCCCCCC.

In certain embodiments, the canine RNA pol I promoter comprises, or alternatively consists of, the following nucleotide sequence:

(SEQ ID NO:10)
TTGATGATTTTTCAAAGTCCTCCCGGAGATCACTGGCTTGGCGGCGTGGC

GGCGTGGCGGCGTGGCGGCGTGGCGGCGTGGCGGCGTGGCGTCTCCACCG

ACCCGTATC.

In certain embodiments, the canine RNA pol I promoter comprises, or alternatively consists of, the following nucleotide sequence:

(SEQ ID NO:23)
TTGATGATTTTTCAAAGTCTCCTCCCGGAGATCACTGGCTTGGCGGCGTG

GCGGCGTGGCGGCGTGGCGGCGTGGCGGCGTGGCGGCGTGGCGTCTCCAC

CGACCGCGTATC.

In certain embodiments, the canine RNA pol I promoter comprises, or alternatively consists of, the following nucleotide sequence:

(SEQ ID NO:11)
TTGATGATTTTTCAAAGTCCTCCCGGAGATCACTGGCTTGGCGGCGTGGC

GGCGT.

In certain embodiments, the canine RNA pol I promoter comprises, or alternatively consists of, the following nucleotide sequence:

(SEQ ID NO:24)
TTGATGATTTTTCAAAGTCTCCTCCCGGAGATCACTGGCTTGGCGGCGTG

GCGGCGT.

In certain embodiments, the canine RNA pol I promoter comprises, or alternatively consists of, the following nucleotide sequence:

(SEQ ID NO:12)
TTGATGATTTTTCAAAGTCCTCCCGGAGATCACTGGCTTGGCGGCGTGGC

GGCGTGGCGGCGTGGCGGCGTGGCGGCGTGGCGGCGTGGCGTCTCCACCG

ACCCGTATCGCCCCTCCTCCCCTCCCCCCCCCCCCCCGTTCCCTGGGTCG

ACCAGATAGCCCTGGGGGCTCCGTGGGGTGGGGTGGGGGGGCGCCGTGG

GGCAGGTTTTGGGGACAGTTGGCCGTGTCACGGTCCCGGGAGGTCGCGGT

GACCTGTGGCTGGTCCCCGCCGGCAGGCGCGGTTATTTTCTTGCCCGAG.

In certain embodiments, the canine RNA pol I promoter comprises, or alternatively consists of, the following nucleotide sequence:

(SEQ ID NO:25)
TTGATGATTTTTCAAAGTCTCCTCCCGGAGATCACTGGCTTGGCGGCGTG

GCGGCGTGGCGGCGTGGCGGCGTGGCGGCGTGGCGGCGTGGCGTCTCCAC

CGACCGCGTATCGCCCCTCCTCCCCTCCCCCCCCCCCCCCGTTCCCTGGG

TCGACCAGATAGCCCTGGGGGCTCCGTGGGGTGGGGTGGGGGGGCGCCG

TGGGGCAGGTTTTGGGGACAGTTGGCCGTGTCACGGTCCCGGGAGGTCGC

GGTGACCTGTGGCTGGTCCCCGCCGGCAGGCGCGGTTATTTTCTTGCCCG

AG.

In certain embodiments, the canine RNA pol I promoter comprises, or alternatively consists of, the following nucleotide sequence:

(SEQ ID NO:13)
GGCGGCGTGGCGGCGTGGCGGCGTGGCGGCGTGGCGTCTCCACCGACCCG

TATCGCCCCTCCTCCCCTCCCCCCCCCCCCCCGTTCCCTGGGTCGACCAG

ATAGCCCTGGGGGCTCCGTGGGGTGGGGTGGGGGGGCGCCGTGGGGCAG

GTTTTGGGGACAGTTGGCCGTGTCACGGTCCCGGGAGGTCGCGGTGACCT

GTGGCTGGTCCCCGCCGGCAGGCGCGGTTATTTTCTTGCCCGAG.

In certain embodiments, the canine RNA pol I promoter comprises, or alternatively consists of, the following nucleotide sequence:

(SEQ ID NO:27)
GGCGGCGTGGCGGCGTGGCGGCGTGGCGGCGTGGCGTCTCCACCGACCGC

GTATCGCCCCTCCTCCCCTCCCCCCCCCCCCCCGTTCCCTGGGTCGACCA

GATAGCCCTGGGGGCTCCGTGGGGTGGGGTGGGGGGGCGCCGTGGGGCA

GGTTTTGGGGACAGTTGGCCGTGTCACGGTCCCGGGAGGTCGCGGTGACC

TGTGGCTGGTCCCCGCCGGCAGGCGCGGTTATTTTCTTGCCCGAG.

In certain embodiments, the canine RNA pol I promoter comprises, or alternatively consists of, the following nucleotide sequence:

(SEQ ID NO:14)
GCCCCTCCTCCCCTCCCCCCCCCCCCCCGTTCCCTGGGTCGACCAGATAG

CCCTGGGGGCTCCGTGGGGTGGGGTGGGGGGGCGCCGTGGGGCAGGTTT

TGGGGACAGTTGGCCGTGTCACGGTCCCGGGAGGTCGCGGTGACCTGTGG

CTGGTCCCCGCCGGCAGGCGCGGTTATTTTCTTGCCCGAG.

In certain embodiments, the canine RNA pol I promoter comprises, or alternatively consists of, the following nucleotide sequence:

(SEQ ID NO:15)
GGGCTCCGTGGGGTGGGGTGGGGGGGCGCCGTGGGGCAGGTTTTGGGGA

CAGTTGGCCGTGTCACGGTCCCGGGAGGTCGCGGTGACCTGTGGCTGGTC

CCCGCCGGCAGGCGCGGTTATTTTCTTGCCCGAG.

In certain embodiments, the canine RNA pol I promoter comprises, or alternatively consists of, the following nucleotide sequence:

(SEQ ID NO:16)
GCCGTGGGGCAGGTTTTGGGGACAGTTGGCCGTGTCACGGTCCCGGGAGG

TCGCGGTGACCTGTGGCTGGTCCCCGCCGGCAGGCGCGGTTATTTTCTTG

CCCGAG.

In certain embodiments, the canine RNA pol I promoter comprises, or alternatively consists of, the following nucleotide sequence:

(SEQ ID NO:17)
TGGCCGTGTCACGGTCCCGGGAGGTCGCGGTGACCTGTGGCTGGTCCCCG

CCGGCAGGCGCGGTTATTTTCTTGCCCGAG.

In certain embodiments, the canine RNA pol I promoter comprises, or alternatively consists of, the following nucleotide sequence:

(SEQ ID NO:18)
GGCGTGGCGTCTCCACCGACCCGTATCGCCCCTCCTCCCCTCCCCCCCC

CCCCCGTTCCCTGGGTCGACCAGATAGCCCTGGGGGCTCCGTGGGGTGGG

GGTGGGGGGGCGCCGTGGGGCAGGTTTTGGGGACAGTTGGCCGTGTCACG

GTCCCGGGAGGTCGCGGTGACCTGTGGCTGGTCCCCGCCGGCAGGCGCGG

TTATTTTCTTGCCCGAG.

In certain embodiments, the canine RNA pol I promoter comprises, or alternatively consists of, the following nucleotide sequence:

(SEQ ID NO:28)
GGCGTGGCGTCTCCACCGACCGCGTATCGCCCCTCCTCCCCTCCCCCCCC

CCCCCCGTTCCCTGGGTCGACCAGATAGCCCTGGGGGCTCCGTGGGGTGG

GGGTGGGGGGCGCCGTGGGGCAGGTTTTGGGGACAGTTGGCCGTGTCAC

GGTCCCGGGAGGTCGCGGTGACCTGTGGCTGGTCCCCGCCGGCAGGCGCG

GTTATTTTCTTGCCCGAG.

In certain embodiments, the canine RNA pol I promoter comprises, or alternatively consists of, the following nucleotide sequence:

(SEQ ID NO:19)
TCGCGGTGACCTGTGGCTGGTCCCCGCCGGCAGGCGCGGTTATTTTCTTG

CCCGAG.

6.3 Vectors and Expression Vectors

In another aspect, the invention provides vectors that comprise a nucleic acid of the invention, including expression vectors useful for recombinantly rescuing a virus from cell culture. Generally, the expression vectors are useful for rescuing any virus known to one skilled in the art to require production of RNA with defined ends during its life-cycle. For example, as discussed above, the influenza virus genomic RNA should have a defined 5' and 3' end to be effectively replicated and packaged in a recombinant system. See, also review in Neumann et al. (2002), 83:2635-2662, which is incorporated by reference herein. The following discussion focuses on expression vectors suitable for use with influenza; however, it should be noted that other viruses can also be rescued using the vectors of the present invention.

In accordance with the present invention, in one embodiment, cDNA encoding viral genomic RNA corresponding to each of the eight genomic segments of influenza (segments may be from different influenza viruses, e.g., 6 from stain X and 2 from strain Y) can be inserted into a recombinant vector for manipulation and production of influenza viruses. A variety of vectors, including viral vectors, plasmids, cosmids, phage, and artificial chromosomes, can be employed in the context of the invention. Typically, for ease of manipulation, the cDNA is inserted into a plasmid vector, providing one or more origins of replication functional in bacterial and eukaryotic cells, and, optionally, a marker convenient for screening or selecting cells incorporating the plasmid sequence. See, e.g., Neumann et al., 1999, PNAS. USA 96:9345-9350.

In one embodiment, the vectors of the invention are bi-directional expression vectors capable of initiating transcription of a viral genomic segment from the inserted cDNA in either direction, that is, giving rise to both (+) strand and (−) strand viral RNA molecules. To effect bi-directional transcription, each of the viral genomic segments is inserted into an expression vector having at least two independent promoters, such that copies of viral genomic RNA are transcribed by a first RNA polymerase promoter (e.g., a canine RNA pol I promoter), from one strand, and viral mRNAs are synthesized from a second RNA polymerase promoter (e.g., a canine RNA Pol II promoter or other promoter that can initiate transcription by RNA pol II in canine cells). Accordingly, the two promoters can be arranged in opposite orientations flanking at least one cloning site (i.e., a restriction enzyme recognition sequence) preferably a unique cloning site, suitable for insertion of viral genomic RNA segments. Alternatively, an "ambisense" expression vector can be employed in which the (+) strand mRNA and the (−) strand viral RNA (as a cRNA) are transcribed from the same strand of the vector. As discussed above, the pol I promoter for transcribing the viral genomic RNA is preferably a canine pol I promoter.

To ensure the correct 3' end of each expressed vRNA or cRNA, each vRNA or cRNA expression vector can incorporate a ribozyme sequence or appropriate termination sequence (e.g., human, mouse, primate, or canine RNA polymerase I termination sequence) downstream of the RNA coding sequence. This may be, for example, the hepatitis delta virus genomic ribozyme sequence or a functional derivative thereof, or the murine rDNA termination sequence (Genbank Accession Number M12074). Alternatively, for example, a Pol I termination sequence may be employed (Neumann et al., 1994, Virology 202:477-479). The RNA expression vectors may be constructed in the same manner as the vRNA expression vectors described in Pleschka et al., 1996, J. Virol. 70:4188-4192; Hoffmann and Webster, 2000, J. Gen Virol. 81:2843-2847; Hoffmann et al., 2002, Vaccine 20:3165-3170; Fodor et al., 1999, J. Virol. 73:9679-9682; Neumann et al., 1999, P.N.A.S. USA 96:9345-9350; and Hoffmann et al., 2000, Virology 267:310-317, each of which is hereby incorporated by reference in its entirety.

In other systems, viral sequences transcribed by the pol I and pol II promoters can be transcribed from different expression vectors. In these embodiments, vectors encoding each of the viral genomic segments under the control of a canine regulatory sequence of the invention, e.g., a canine pol I promoter ("vRNA expression vectors") and vectors encoding one or more viral polypeptides, e.g., influenza PA, PB1, PB2, and NP polypeptides ("protein expression vectors") under the control of a pol II promoter can be used.

In either case, with regard to the pol II promoter, the influenza virus genome segment to be expressed can be operably linked to an appropriate transcription control sequence (promoter) to direct mRNA synthesis. A variety of promoters are suitable for use in expression vectors for regulating transcription of influenza virus genome segments. In certain embodiments, the cytomegalovirus (CMV) DNA dependent RNA Polymerase II (Pol II) promoter is utilized. If desired, e.g., for regulating conditional expression, other promoters can be substituted which induce RNA transcription under the specified conditions, or in the specified tissues or cells. Numerous viral and mammalian, e.g., human promoters are available, or can be isolated according to the specific application contemplated. For example, alternative promoters obtained from the genomes of animal and human viruses include such promoters as the adenovirus (such as Adenovirus 2), papilloma virus, hepatitis-B virus, and polyoma virus, and various retroviral promoters. Mammalian promoters include, among many others, the actin promoter, immunoglobulin promoters, heat-shock promoters, and the like. In a specific embodiment, the regulatory sequence comprises the adenovirus 2 major late promoter linked to the spliced tripartite leader sequence of human adenovirus 2, as described by Berg et al., Bio Techniques 14:972-978. In addition, bacteriophage promoters can be employed in conjunction with the cognate RNA polymerase, e.g., the T7 promoter.

Expression vectors used to express viral proteins, in particular viral proteins for RNP complex formation, will preferably express viral proteins homologous to the desired virus. The expression of viral proteins by these expression vectors may be regulated by any regulatory sequence known to those of skill in the art. The regulatory sequence may be a constitutive promoter, an inducible promoter or a tissue-specific promoter. Further examples of promoters which may be used to control the expression of viral proteins in protein expression vectors include, but are not limited to, the SV40 early promoter region (Bemoist and Chambon, 1981, Nature 290: 304-310), the promoter contained in the 3' long terminal repeat of Rous sarcoma virus (Yamamoto, et al, 1980, Cell 22:787-797), the herpes thymidine kinase promoter (Wagner et al., 1981, Proc. Natl. Acad. Sci. USA 78:1441-1445), the regulatory sequences of the metallothionein gene (Brinster et al., 1982, Nature 296:39-42); prokaryotic expression vectors such as the β-lactamase promoter (Villa-Kamaroff et al., 1978, Proc. Natl. Acad. Sci. USA 75:3727-3731), or the tac promoter (DeBoer et al., 1983, Proc. Natl. Acad. Sci. USA 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Omitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5: 1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, protein expression vectors of the invention comprise a promoter operably linked to a nucleic acid sequence, one or more origins of replication, and, optionally, one or more selectable markers (e.g., an antibiotic resistance gene). In another embodiment, a protein expression vector of the invention that is capable of producing bicistronic mRNA may be produced by inserting bicistronic mRNA sequence. Certain internal ribosome entry site (IRES) sequences may be utilized. Preferred IRES elements include, but are not limited to the mammalian BiP IRES and the hepatitis C virus IRES.

In one embodiment, a nucleic acid of the invention is inserted into plasmid pAD3000 or a derivative thereof. See, U.S. patent application publication 20050266026 and FIG. 10. Thus, in certain embodiments, the expression vector is a bi-directional expression vector. In certain embodiments, the expression vector comprises a SV40 polyadenylation signal flanking a segment of the influenza virus genome internal to the two promoters. In certain embodiments, the expression vector comprises the cytomegalovirus (CMV) DNA dependent RNA Pol II promoter. In one embodiment, a nucleic acid of the invention is inserted into plasmid pAD4000 or a derivative thereof. In one embodiment, nucleic acids of the invention comprise or alternatively consist of the sequence of pAD4000 presented as SEQ ID NO:29.

Vectors containing gene inserts can be identified by, e.g., three general approaches: (a) nucleic acid hybridization; (b) presence or absence of "marker" gene functions; and, in the case of expression vectors, (c) expression of inserted sequences. In the first approach, the presence of the viral gene inserted in an vector(s) can be detected by nucleic acid hybridization using probes comprising sequences that are homologous to the inserted gene(s). In the second approach, the recombinant vector/host system can be identified and selected based upon the presence or absence of certain "marker" gene functions (e.g., resistance to antibiotics or transformation phenotype) caused by the insertion of the gene(s) in the vector(s). In the third approach, expression vectors can be identified by assaying the gene product expressed. Such assays can be based, for example, on the physical or functional properties of the viral protein in in vitro assay systems, e.g., binding of viral proteins to antibodies.

In a specific embodiment, one or more protein expression vectors encode and express the viral proteins necessary for the formation of RNP complexes. In another embodiment, one or more protein expression vectors encode and express the viral proteins necessary to form viral particles. In yet another embodiment, one or more protein expression vectors encode and express the all of the viral proteins of a particular negative-strand RNA virus.

Transcription from expression vectors can optionally be increased by including an enhancer sequence. Enhancers are typically short, e.g., 10-500 bp, cis-acting DNA elements that act in concert with a promoter to increase transcription. Many enhancer sequences have been isolated from mammalian genes (hemoglobin, elastase, albumin, alpha.-fetoprotein, and insulin), and eukaryotic cell viruses. The enhancer can be spliced into the vector at a position 5' or 3' to the heterologous coding sequence, but is typically inserted at a site 5' to the promoter. Typically, the promoter, and if desired, additional transcription enhancing sequences are chosen to optimize expression in the host cell type into which the heterologous DNA is to be introduced (Scharf et al. (1994) Heat stress promoters and transcription factors *Results Probl Cell Differ* 20:125-62; Kriegler et al. (1990) Assembly of enhancers, promoters, and splice signals to control expression of transferred genes *Methods in Enzymol* 185: 512-27). Optionally, the amplicon can also contain a ribosome binding site or an internal ribosome entry site (IRES) for translation initiation.

The expression vectors of the invention can also include sequences for the termination of transcription and for stabilizing the mRNA, such as a polyadenylation site or a termination sequence (e.g., human, mouse, primate, or canine RNA polymerase I termination sequence). Such sequences are commonly available from the 5' and, occasionally 3', untranslated regions of eukaryotic or viral DNAs or cDNAs. In some embodiments, the SV40 polyadenylation sequences provide a polyadenylation signal.

In addition, as described above, the vectors optionally include one or more selectable marker genes to provide a phenotypic trait for selection of transformed host cells, in addition to genes previously listed, markers such as dihydrofolate reductase or neomycin resistance are suitable for selection in eukaryotic cell culture.

The expression vector containing the appropriate DNA sequence as described above, as well as an appropriate promoter or control sequence, can be employed to transform a host cell permitting expression of the protein. While the expression vectors of the invention can be replicated in bacterial cells, most frequently it will be desirable to introduce them into mammalian cells, e.g., Vero cells, BHK cells, MDCK cell, 293 cells, COS cells, more preferably MDCK cells, for the purpose of expression.

The expression vectors of the invention can be used to directing the expressing of genomic vRNA(s) or corresponding cRNA(s) which have one or more mutations (e.g., removal or inactivation of a polybasic cleavage site in the HA gene of particular influenza pandemic strains such as H5N1). These mutations may result in the attenuation of the virus. For example, the vRNA segments may be the vRNA segments of an influenza A virus having an attenuated base pair substitution in a pan-handle duplex promoter region, in particular, for example, the known attenuating base pair substitution of A for C and U for G at position 11-12' in the duplex region of the NA-specific vRNA (Fodor et al., 1998, J. Virol. 6923-6290). By using the methods of the invention to produce recombinant negative-strand RNA virus, new attenuating mutations may be identified.

Further, any of the expression vectors described in U.S. Pat. Nos. 6,951,754, 6,887,699, 6,649,372, 6,544,785, 6,001,634, 5,854,037, 5,824,536, 5,840,520, 5,820,871, 5,786,199, and 5,166,057 and U.S. Patent Application Publication Nos. 20060019350, 20050158342, 20050037487, 20050266026, 20050186563, 20050221489, 20050032043, 20040142003, 20030035814, and 20020164770 can be used in accordance with the present invention. Generally, the vectors described in these publications can be adapted for use in accordance with the present invention by introducing a nucleic acid of the invention (e.g., a canine regulatory sequence of the invention such as a canine poll promoter sequence) as described herein into the expression vectors to direct synthesis of viral vRNA or cRNA.

6.3.1 Additional Expression Elements

Most commonly, the genome segment encoding the influenza virus protein includes any additional sequences necessary for its expression, including translation into a functional viral protein. In other situations, a minigene, or other artificial construct encoding the viral proteins, e.g., an HA or NA protein, can be employed. In this case, it is often desirable to include specific initiation signals which aid in the efficient translation of the heterologous coding sequence. These signals can include, e.g., the ATG initiation codon and adjacent sequences. To insure translation of the entire insert, the initiation codon is inserted in the correct reading frame relative to the viral protein. Exogenous transcriptional elements and initiation codons can be of various origins, both natural and synthetic. The efficiency of expression can be enhanced by the inclusion of enhancers appropriate to the cell system in use.

If desired, polynucleotide sequences encoding additional expressed elements, such as signal sequences, secretion or localization sequences, and the like can be incorporated into the vector, usually, in-frame with the polynucleotide sequence of interest, e.g., to target polypeptide expression to a desired cellular compartment, membrane, or organelle, or into the cell culture media. Such sequences are known to those of skill, and include secretion leader peptides, organelle targeting sequences (e.g., nuclear localization sequences, ER retention signals, mitochondrial transit sequences), membrane localization/anchor sequences (e.g., stop transfer sequences, GPI anchor sequences), and the like.

6.4 Expression Vectors for Making Chimeric Viruses

The expression vectors of the invention can also be used to make chimeric viruses that express sequences heterologous to a viral genome. Expression vectors directing the expression of vRNA(s) or corresponding cRNA(s) are introduced into host cells along with expression vectors direct the expression of viral proteins to generate novel infectious recombinant negative-strand RNA viruses or chimeric viruses. See, e.g., US patent application publication no. US20040002061. Heterologous sequences which may be engineered into these viruses include antisense nucleic acids and nucleic acid such as a ribozyme. Alternatively, heterologous sequences which express a peptide or polypeptide may be engineered into these viruses. Heterologous sequences encoding the following peptides or polypeptides may be engineered into these viruses include: 1) antigens that are characteristic of a pathogen; 2) antigens that are characteristic of autoimmune disease; 3) antigens that are characteristic of an allergen; and 4) antigens that are characteristic of a tumor. For example, heterologous gene sequences that can be engineered into the chimeric viruses of the invention include, but are not limited to, epitopes of human immunodeficiency virus (HIV) such as gp160; hepatitis B virus surface antigen (HBsAg); the glycoproteins of herpes virus (e.g., gD, gE); VP1 of poliovirus; and antigenic determinants of nonviral pathogens such as bacteria and parasites to name but a few.

Antigens that are characteristic of autoimmune disease typically will be derived from the cell surface, cytoplasm, nucleus, mitochondria and the like of mammalian tissues, including antigens characteristic of diabetes mellitus, multiple sclerosis, systemic lupus erythematosus, rheumatoid arthritis, pernicious anemia, Addison's disease, scleroderma, autoimmune atrophic gastritis, juvenile diabetes, and discoid lupus erythromatosus.

Antigens that are allergens are generally proteins or glycoproteins, including antigenis derived from pollens, dust, molds, spores, dander, insects and foods.

Antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and glycoproteins. Tumors include, but are not limited to, those derived from the types of cancer: lip, nasopharynx, pharynx and oral cavity, esophagus, stomach, colon, rectum, liver, gall bladder, pancreas, larynx, lung and bronchus, melanoma of skin, breast, cervix, uterine, ovary, bladder, kidney, uterus, brain and other parts of the nervous system, thyroid, prostate, testes, Hodgkin's disease, non-Hodgkin's lymphoma, multiple myeloma and leukemia.

In one specific embodiment of the invention, the heterologous sequences are derived from the genome of human immunodeficiency virus (HIV), preferably human immunodeficiency virus-1 or human immunodeficiency virus-2. In another embodiment of the invention, the heterologous coding sequences may be inserted within an negative-strand RNA virus gene coding sequence such that a chimeric gene product is expressed which contains the heterologous peptide sequence within the viral protein. In such an embodiment of the invention, the heterologous sequences may also be derived from the genome of a human immunodeficiency virus, preferably of human immunodeficiency virus-1 or human immunodeficiency virus-2.

In instances whereby the heterologous sequences are HIV-derived, such sequences may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25) tat, rev, nef, vif, vpu, vpr, and/or vpx.

One approach for constructing these hybrid molecules is to insert the heterologous coding sequence into a DNA complement of a negative-strand RNA virus gene so that the heterologous sequence is flanked by the viral sequences required for viral polymerase activity; e.g., a canine RNA pol I promoter and a polyadenylation site. In an alternative approach, oligonucleotides encoding a canine RNA pol I promoter, e.g., the complement of the 3'-terminus or both termini of the virus genomic segments can be ligated to the heterologous coding sequence to construct the hybrid molecule. The placement of a foreign gene or segment of a foreign gene within a target sequence was formerly dictated by the presence of appropriate restriction enzyme sites within the target sequence. However, recent advances in molecular biology have lessened this problem greatly. Restriction enzyme sites can readily be placed anywhere within a target sequence through the use of site-directed mutagenesis (e.g., see, for example, the techniques described by Kunkel, 1985, Proc. Natl. Acad. Sci. U.S.A. 82:488). Variations in polymerase chain reaction (PCR) technology, described, also allow for the specific insertion of sequences (i.e., restriction enzyme sites) and allow for the facile construction of hybrid molecules. Alternatively, PCR reactions could be used to prepare recombinant templates without the need of cloning. For example, PCR reactions could be used to prepare double-stranded DNA molecules containing a DNA-directed RNA polymerase promoter (e.g., bacteriophase T3, T7 or SP6) and the hybrid sequence containing the heterologous gene and a canine RNA pol I promoter. RNA templates could then be transcribed directly from this recombinant DNA. In yet another embodiment, the recombinant vRNAs or corresponding cRNAs may be prepared by ligating RNAs specifying the negative polarity of the heterologous gene and the canine RNA pol I promoter using an RNA ligase.

Bicistronic mRNA could be constructed to permit internal initiation of translation of viral sequences and allow for the expression of foreign protein coding sequences from the regular terminal initiation site. Alternatively, a bicistronic mRNA sequence may be constructed wherein the viral sequence is translated from the regular terminal open reading frame, while the foreign sequence is initiated from an internal site. Certain internal ribosome entry site (IRES) sequences may be utilized. The IRES sequences which are chosen should be short enough to not interfere with virus packaging limitations. Thus, it is preferable that the IRES chosen for such a bicistronic approach be no more than 500 nucleotides in length, with less than 250 nucleotides being preferred. Further, it is preferable that the IRES utilized not share sequence or structural homology with picornaviral elements. Preferred IRES elements include, but are not limited to the mammalian BiP FRES and the hepatitis C virus IRES.

Alternatively, a foreign protein may be expressed from an internal transcriptional unit in which the transcriptional unit has an initiation site and polyadenylation site. In another embodiment, the foreign gene is inserted into a negative-strand RNA virus gene such that the resulting expressed protein is a fusion protein.

6.5 Methods of Generating Recombinant Viruses

The present invention provides methods of generating infectious recombinant negative-strand RNA virus by introducing protein expression vectors and vRNA or corresponding cRNA expressing expression vectors of the invention into host cells in the absence of helper virus. Preferably, the host cells are canine cells, e.g., MDCK cells. The present invention also provides methods of generating infectious recombinant negative-strand RNA virus by introducing protein expression vectors and vRNA or corresponding cRNA expressing expression vectors of the invention into host cells in the presence of helper virus. The host cells may be, e.g., canine cells (such as MDCK cells),Vero cells, Per.C6 cells, BHK cells, PCK cells, MDCK cells, MDBK cells, 293 cells (e.g., 293T cells), and COS cells Protein expression vectors and expression vectors directing the expression of vRNAs or corresponding cRNAs can be introduced into host cells using any technique known to those of skill in the art without limitation. For example, expression vectors of the invention can be introduced into host cells by employing electroporation, DEAE-dextran, calcium phosphate precipitation, liposomes, microinjection, and microparticle-bombardment (see, e.g., Sambrook et al., Molecular Cloning: A Laboratory Manual, 2 ed., 1989, Cold Spring Harbor Press, Cold Spring Harbor, N.Y.). The expression vectors of the invention may be introduced into host cells simultaneously or sequentially.

In one embodiment, one or more expression vectors directing the expression of vRNA(s) or corresponding cRNA(s) are introduced into host cells prior to the introduction of expression vectors directing the expression of viral proteins. In another embodiment, one or more expression vectors directing the expression of viral proteins are introduced into host cells prior to the introduction of the one or more expression vectors directing the expression of vRNA(s) or corresponding cRNA(s). In accordance with these embodiments, the expression vectors directing the expression of the vRNA(s) or corresponding cRNA(s) may introduced together or separately in different transfections. Further, in accordance with these embodiments, the expression vectors directing the expression of the viral proteins can be introduced together or separately in different transfections.

In another embodiment, one or more expression vectors directing the expression of vRNA(s) or corresponding cRNA(s) and one or more expression vectors directing the expression of viral proteins are introduced into host cells simultaneously. In certain embodiments, all of the expression vectors are introduced into host cells using liposomes.

In one embodiment a method for producing a recombinant influenza virus is provided comprising introducing into a population of canine cells expression vectors capable of expressing in said cells genomic vRNA segments to provide the complete genomic vRNA segments of said virus, wherein said expression vectors comprise nucleotides 1-469 of SEQ ID NO:26, or a functionally active fragment thereof; (b) introducing into said cells expression vectors capable of expressing mRNA encoding one or more polypeptides of said virus; and (c) culturing said cells whereby influenza viral particles are produced. In one embodiment, the titers of the influenza viral particles produced upon culturing said cells for 48-72 hours is at least $1.0\times10^4$ PFU/ml or at least $1.0\times10^5$ PFU/ml.

In one embodiment, a method for producing recombinant influenza viruses are provided wherein the method comprises introducing into a population of canine cells expression vectors capable of expressing in said cells genomic vRNA segments to provide the complete genomic vRNA segments of said virus, wherein said expression vectors comprise nucleotides 1-469 of SEQ ID NO:26, or a functionally active fragment thereof; (b) introducing into said cells expression vectors capable of expressing mRNA encoding one or more polypeptides of said virus; and (c) culturing said cells whereby influenza viral particles are produced. In one embodiment, the titers of the influenza viral particles produced upon culturing said cells for 48-72 hours is at least $1.0\times10^4$ PFU/ml or at least $1.0\times10^5$ PFU/ml.

Appropriate amounts and ratios of the expression vectors for carrying out a method of the invention may be determined by routine experimentation. As guidance, in the case of liposomal transfection or calcium precipitation of plasmids into the host cells, it is envisaged that each plasmid may be employed at a few μgs, e.g., 1 to 10 μg, for example, diluted to a final total DNA concentration of about 0.1 μg/ml prior to mixing with transfection reagent in conventional manner. It may be preferred to use vectors expressing NP and/or RNA-dependent RNA polymerase subunits at a higher concentration than those expressing vRNA segments. One skilled in the art will appreciate that the amounts and ratios of the expression vectors may vary depending upon the host cells.

In one embodiment, at least 0.5 μg, preferably at least 1 μg, at least 2.5 μg, at least 5 μg, at least 8 μg, at least 10 μg, at least 15 μg, at least 20 μg, at least 25 μg, or at least 50 μg of one or more protein expression vectors of the invention are introduced into host cells to generate infectious recombinant negative-strand RNA virus. In another embodiment, at least 0.5 μg, preferably at least 1 μg, at least 2.5 μg, at least 5 μg, at least 8 μg, at least 10 μg, at least 15 μg, at least 20 μg, at least 25 μg or at least 50 μg of one or more expression vectors of the invention directing the expression of vRNAs or cRNAs are introduced into host cells to generate infectious recombinant negative-strand RNA virus.

Host cells which may be used to generate the negative-strand RNA viruses of the invention include primary cells, cultured or secondary cells, and transformed or immortalized cells (e.g., 293 cells, 293T cells, CHO cells, Vero cells, PK, MDBK, OMK and MDCK cells). Host cells are preferably animal cells, more preferably mammalian cells, and most preferably canine cells. In a preferred embodiment, infectious recombinant negative-strand RNA viruses of the invention are generated in MDCK cells.

The present invention provides methods of generating infectious recombinant negative-strand RNA virus in stably transduced host cell lines. The stably transduced host cell lines of the invention may be produced by introducing cDNA controlled by appropriate expression control elements (e.g., promoter, enhancer, sequences, transcription termination sequences, polyadenylation sites, etc.), and a selectable marker into host cells. Following the introduction of the foreign DNA, the transduced cells may be allowed to grow for 1-2 days in an enriched media, and then are switched to a selective media. The selectable marker confers resistance to the cells and allows the cells to stably integrate the DNA into their chromosomes. Transduced host cells with the DNA stably integrated can be cloned and expanded into cell lines.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

The infectious recombinant negative-strand RNA viruses generated by methods of the invention which are not attenuated, may be attenuated or killed by, for example, classic methods. For example, recombinant negative-strand RNA viruses of the invention may be killed by heat or formalin treatment, so that the virus is not capable of replicating. Recombinant negative-strand RNA viruses of the invention which are not attenuated may be attenuated by, e.g., passage through unnatural hosts to produce progeny viruses which are immunogenic, but not pathogenic.

Attenuated, live or killed viruses produced in accordance with the invention may subsequently be incorporated into a vaccine composition in conventional manner or used to produce additional virus, e.g., in eggs. Where such a virus has a chimeric vRNA segment as discussed above which encodes a foreign antigen, it may be formulated to achieve vaccination against more than one pathogen simultaneously. Attenuated recombinant viruses produced in accordance with the invention which possess a chimeric vRNA segment may also be designed for other therapeutic uses, e.g., an anti-tumor agent or gene therapy tool, in which case production of the virus will be followed by its incorporation into an appropriate pharmaceutical composition together with a pharmaceutically acceptable carrier or diluent.

Helper virus free rescue in accordance with the invention is particularly favored for generation of reassortant viruses, especially reassortant influenza viruses desired for vaccine use particularly since selection methods are not needed to rid the culture of helper virus.

The methods of the present invention may be modified to incorporate aspects of methods known to those skilled in the art, in order to improve efficiency of rescue of infectious viral particles. For example, the reverse genetics technique involves the preparation of synthetic recombinant viral RNAs that contain the non-coding regions of the negative strand virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoprotein (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in U.S. Pat. No. 5,789,229 issued Aug. 4, 1998; in European Patent Publication EP 0702085A1, published Feb. 20, 1996; in U.S. patent application Ser. No. 09/152,845; in International Patent Publications PCR WO97/12032 published Apr. 3, 1997; WO96/34625 published Nov. 7, 1996; in European Patent Publication EP-A780475; WO99/02657 published Jan. 21, 1999; WO98/53078 published Nov. 26, 1998; WO98/02530 published Jan. 22, 1998; WO99/15672 published Apr. 1, 1999; WO98/13501 published Apr. 2, 1998; WO97/06720 published Feb. 20, 1997; and EPO 780 47SA1 published Jun. 25, 1997, each of which is incorporated by reference herein in its entirety.

6.5.1 Specific Segmented Negative-Strand RNA Virus Embodiments

The present invention provides a method for generating in cultured cells infectious recombinant viral particles of a segmented negative-strand RNA virus having greater than 3 genomic vRNA segments, for example an influenza virus such as an influenza A virus, said method comprising: (a) introducing into a population of cells capable of supporting growth of said virus a first set of expression vectors capable of expressing in said cells genomic vRNA segments to provide the complete genomic vRNA segments of said virus; (b) introducing into said cells a second set of expression vectors capable of expressing mRNA encoding one or more polypeptides of said virus; and (c) culturing said cells whereby said viral particles are produced. In certain embodiments, the cells are canine cells. In certain embodiments, the cells are MDCK cells. In certain embodiments, the recombinant virus is influenza A or B virus. In certain embodiments, the first set of expression vectors is contained in 1-8 plasmids. In certain embodiments, the first set of expression vectors is contained in one plasmid. In certain embodiments, the second set of expression vectors is contained in 1-8 plasmids. In certain embodiments, the second set of expression vectors is contained in one plasmid. In certain embodiments, the first, second, or both sets of expression vectors are introduced by electroporation. In certain embodiments, the first set of expression vectors encode each vRNA segment of an influenza virus. In certain embodiments, the second set of expression vectors encode the mRNA of one or more or all influenza polypeptides. In certain embodiments, the first set or second set of expression vectors (or both sets) comprise a nucleic acid of the invention, for example, a canine RNA pol I regulatory sequence of the invention (e.g., a canine RNA pol I promoter). In certain embodiments, the first set or second set of expression vectors (or both sets) encode a vRNA or mRNA of a second virus. For instance, a set of vectors comprises one or more vectors encoding the HA and/or NA mRNA and/or vRNA of a second influenza virus. In one embodiment, helper virus is used in the method. In one embodiment, the cultured cells used in the method are canine cells.

The present invention provides a method for generating in cultured cells infectious recombinant viral particles of a segmented negative-strand RNA virus having greater than 3 genomic vRNA segments, for example an influenza virus such as an influenza A virus, said method comprising: (a) introducing into a population of cells capable of supporting growth of said virus a set of expression vectors capable of both expressing in said cells genomic vRNA segments to provide the complete genomic vRNA segments of said virus and capable of expressing mRNA encoding one or more polypeptides of said virus; (b) culturing said cells whereby said viral particles are produced. In certain embodiments, the cells are canine cells. In certain embodiments, the cells are MDCK cells. In certain embodiments, the virus is influenza A or B virus. In certain embodiments, the set of expression vectors are comprised in 1-17 plasmids. In certain embodiments, the set of expression vectors is contained in 1-8 plasmid. In certain embodiments, the set of expression vectors is contained in 1-3 plasmids. In certain embodiments, the set of expression vectors is contained in one plasmid. In certain embodiments, the sets of expression vectors are introduced by electroporation. In certain embodiments, the set of expression vectors encode each vRNA segment of an influenza virus. In certain embodiments, the set of expression vectors encode the mRNA of one or more influenza polypeptide. In certain embodiments, the set of expression vectors encode each vRNA segment of an influenza virus and the mRNA of one or more influenza polypeptide. In certain embodiments, the set of expression vectors comprise a nucleic acid of the invention, for example, a canine RNA pol I regulatory sequence of the invention (e.g., a canine RNA pol I promoter). In certain embodiments, the set of expression vectors encode a vRNA or mRNA of a second virus. For instance, the set of vectors comprises one or more vectors encoding the HA and/or NA mRNA and/or vRNA of a second influenza virus. In certain embodiments, the first set or second set of expression vectors (or both sets) encode a vRNA or mRNA of a second virus. For instance, a set of vectors comprises one or more vectors encoding the HA and/or NA mRNA and/or vRNA of a second influenza virus. In one embodiment, helper virus is used in the method. In one embodiment, the cultured cells used in the method are canine cells.

The present invention provides a method for generating in cultured cells infectious recombinant viral particles of a negative-strand RNA virus, said method comprising: (a) introducing into a population of cells capable of supporting growth of said virus a first set of expression vectors capable of expressing in said cells genomic vRNA to provide the complete genomic vRNA of said virus; (b) introducing into said cells a second set of expression vectors capable of expressing mRNA encoding one or more polypeptides of said virus; and (c) culturing said cells whereby said viral particles are produced. In certain embodiments, the cells are canine cells. In certain embodiments, the cells are MDCK cells. In certain embodiments, the virus is influenza B virus. In certain embodiments, the first set of expression vectors is contained in 1-8 plasmids. In certain embodiments, the first set of expression vectors is contained in one plasmid. In certain embodiments, the second set of expression vectors is contained in 1-8 plasmids. In certain embodiments, the second set of expression vectors is contained in one plasmid. In certain embodiments, the first, second, or both sets of expression vectors are introduced by electroporation. In certain embodiments, the first set of expression vectors encode each vRNA segment of an influenza virus. In certain embodiments, the second set of expression vectors encode the mRNA of one or more influenza polypeptide. In certain embodiments, the first set or second set of expression vectors (or both sets) comprise a nucleic acid of the invention, for example, a canine RNA pol I regulatory sequence of the invention (e.g., a canine RNA pol I promoter). In one embodiment, helper virus is used in the method. In one embodiment, the cultured cells used in the method are canine cells.

The present invention provides a method for generating in cultured cells infectious viral particles of a negative-strand RNA virus, said method comprising: (a) introducing into a population of cells capable of supporting growth of said virus a set of expression vectors capable of both expressing in said cells genomic vRNA to provide the complete genomic vRNA of said virus and capable of expressing mRNA encoding one or more polypeptides of said virus; (b) culturing said cells whereby said viral particles are produced. In certain embodiments, the cells are canine cells. In certain embodiments, the cells are MDCK cells. In certain embodiments, the virus is influenza B virus. In certain embodiments, the set of expression vectors is contained in 1-17 plasmids. In certain embodiments, the set of expression vectors is contained in 1-8 plasmid. In certain embodiments, the set of expression vectors is contained in 1-3 plasmids. In certain embodiments, the sets of expression vectors are introduced by electroporation. In certain embodiments, the set of expression vectors encode each vRNA segment of an influenza virus. In certain embodiments, the set of expression vectors encode the mRNA of one or more influenza polypeptide. In certain embodiments, the set of expression vectors encode each vRNA segment of an influenza virus and the mRNA of one or more influenza polypeptide. In certain embodiments, the set of expression vectors comprise a nucleic acid of the invention, for example, a canine RNA pol I regulatory sequence of the invention (e.g., a canine RNA pol I promoter). In certain embodiments, the set of expression vectors encode a vRNA or mRNA of a second virus. For instance, the set of vectors comprises one or more vectors encoding the HA and/or NA mRNA and/or vRNA of a second influenza virus. In one embodiment, helper virus is used in the method. In one embodiment, the cultured cells used in the method are canine cells.

The present invention provides a method for generating in cultured canine cells infectious viral particles of a segmented negative-strand RNA virus having greater than 3 genomic vRNA segments, for example an influenza virus such as an influenza A virus, said method comprising: (a) providing a first population of canine cells capable of supporting growth of said virus and having introduced a first set of expression vectors capable of directly expressing in said canine cells genomic vRNA segments to provide the complete genomic vRNA segments of said virus, or the corresponding cRNAs, in the absence of a helper virus to provide any such RNA segment, said canine cells also being capable of providing a nucleoprotein and RNA-dependent RNA polymerase whereby RNP complexes containing the genomic vRNA segments of said virus can be formed and said viral particles can be assembled within said canine cells; and (b) culturing said canine cells whereby said viral particles are produced. In certain embodiments, the canine cells are MDCK cells.

The present invention also provides a method for generating in cultured canine cells infectious viral particles of a segmented negative-strand RNA virus, said method comprising: (i) providing a first population of canine cells which are capable of supporting the growth of said virus and which are modified so as to be capable of providing (a) the genomic vRNAs of said virus in the absence of a helper virus and (b) a nucleoprotein and RNA-dependent RNA polymerase whereby RNA complexes containing said genomic vRNAs can be formed and said viral particles can be assembled, said genomic vRNAs being directly expressed in said cells under the control of a canine RNA Pol I regulatory sequence, or functional derivative thereof; and (ii) culturing said canine cells whereby said viral particles are produced.

The present specification also provides a method for generating in cultured cells infectious viral particles of a segmented negative-strand RNA virus, said method comprising: (i) providing a population of canine cells which are capable of supporting the growth of said virus and which are modified so as be capable of providing (a) the genomic vRNAs of said virus in the absence of a helper virus and (b) a nucleoprotein and RNA-dependent RNA polymerase whereby RNP complex or complexes containing said genomic vRNAs can be formed and said viral particles can be assembled, said genomic RNAs being directly expressed in said canine cells under the control of a canine RNA Pol I regulatory sequence or a functional derivative thereof, e.g., a canine RNA Pol I promoter as described above; and (ii) culturing said canine cells whereby said viral particles are produced.

In a specific embodiment, an infectious recombinant negative-strand RNA virus having, at least 4, at least 5, at least 6, at least 7, or at least 8 genomic vRNA segments in a canine host cell is generated using the methods described herein.

In a specific embodiment, the present invention provides for methods of generating infectious recombinant influenza virus in host cells using expression vectors to express the vRNA segments or corresponding cRNAs and influenza virus proteins, in particular PB1, PB2, PA and NA. In accordance with this embodiment, helper virus may or may not be included to generate the infectious recombinant influenza viruses.

The infectious recombinant influenza viruses of the invention may or may not replicate and produce progeny. Preferably, the infectious recombinant influenza viruses of the invention are attenuated. Attenuated infectious recombinant influenza viruses may, for example, have a mutation in the NS1 gene.

In certain embodiments, an infectious recombinant viruses of the invention can be used to produce other viruses useful to prepare a vaccine composition of the invention. In one embodiment, recombinant or reassortant viruses produced by a method of the invention are used for the production of additional virus for use as a vaccine. For example, a population of recombinant or reassortant viruses produced by the methods of the invention which incorporate a canine RNA pol I regulatory sequence of the invention (e.g., a canine RNA pol I promoter). Subsequently, the population of viruses is grown in eggs or another culture such that additional viruses are produced for the preparation of vaccines or an immunogenic composition.

In certain embodiments, the infectious recombinant influenza viruses of the invention express heterologous (i.e., non-influenza virus) sequences. In another embodiment, the infectious recombinant influenza viruses of the invention express influenza virus proteins from different influenza strains. In yet another preferred embodiment, the infectious recombinant influenza viruses of the invention express fusion proteins.

6.5.2 Introduction of Vectors into Host Cells

Vectors comprising influenza genome segments can be introduced (e.g., transfected) into host cells according to methods well known in the art (see, e.g., US patent application publication nos. US20050266026 and 20050158342) for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as, e.g., MDCK cells, COS cells, 293T cells, or combinations thereof, using the polyamine transfection reagent TransIT-LT1 (Mirus) according to the manufacturer's instructions. Approximately 1 µg of each vector to be introduced into the population of host cells can be combined with approximately 2 µl of TransIT-LT1 diluted in 160 µl medium, preferably serum-free medium, in a total volume of 200 µl. The DNA: transfection reagent mixtures can be incubated at room temperature for 45 min followed by addition of 800 µl of medium. The transfection mixture is then added to the host cells, and the cells are cultured as described above. Accordingly, for the production of recombinant or reassortant viruses in cell culture, vectors incorporating each of the 8 genome segments, (PB2, PB1, PA, NP, M, NS, HA and NA) are mixed with approximately 20 µl TransIT-LT1 and transfected into host cells. Optionally, serum-containing medium is replaced prior to transfection with serum-free medium, e.g., Opti-MEM I, and incubated for 4-6 hours.

Alternatively, electroporation can be employed to introduce vectors incorporating influenza genome segments into host cells. See, e.g., US patent application publications US20050266026 and 20050158342, which are incorporated by reference herein. For example, plasmid vectors incorporating an influenza A or influenza B virus are introduced into MDCK cells using electroporation according to the following procedure. In brief, $5\times10^6$ MDCK cells, e.g., grown in Modified Eagle's Medium (MEM) supplemented with 10% Fetal Bovine Serum (FBS) are resuspended in 0.3 ml OptiMEM and placed in an electroporation cuvette. Twenty micrograms of DNA in a volume of up to 25 μl is added to the cells in the cuvette, which is then mixed gently by tapping. Electroporation is performed according to the manufacturer's instructions (e.g., BioRad Gene Pulser II with Capacitance Extender Plus connected) at 300 volts, 950 microFarads with a time constant of between 35-45 msec. The cells are remixed by gently tapping and approximately 1-2 minutes following electroporation 0.7 ml OPTI-MEM is added directly to the cuvette. The cells are then transferred to two wells of a standard 6 well tissue culture dish containing 2 ml OPTI-MEM without serum. The cuvette is washed to recover any remaining cells and the wash suspension is divided between the two wells. Final volume is approximately 3.5 mls. The cells are then incubated under conditions permissive for viral growth, e.g., at approximately 33° C. for cold adapted strains.

Further guidance on introduction of vectors into host cells may be found, for example, in U.S. Pat. Nos. 6,951,754, 6,887,699, 6,649,372, 6,544,785, 6,001,634, 5,854,037, 5,824,536, 5,840,520, 5,820,871, 5,786,199, and 5,166,057 and U.S. Patent Application Publication Nos. 20060019350, 20050158342, 20050037487, 20050266026, 20050186563, 20050221489, 20050032043, 20040142003, 20030035814, and 20020164770.

6.6 Cell Culture

Typically, propagation of the virus is accomplished in the media compositions in which the host cell is commonly cultured. Suitable host cells for the replication of influenza virus include, e.g., Vero cells, Per.C6 cells, BHK cells, MDCK cells, 293 cells and COS cells, including 293T cells, COS7 cells. MDCK cells are preferred in the context of the present invention. Use of non-tumorigenic MDCK cells as host cells is also an embodiment of the invention. Co-cultures including two of the above cell lines, e.g., MDCK cells and either 293T or COS cells can also be employed at a ratio, e.g., of 1:1, to improve replication efficiency. See, e.g., 20050158342. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are known to those of skill in the art. General protocols are provided, e.g., in Freshney (1983) *Culture of Animal Cells: Manual of Basic Technique*, Alan R. Liss, New York; Paul (1975) *Cell and Tissue Culture*, $5^{th}$ ed., Livingston, Edinburgh; Adams (1980) *Laboratory Techniques in Biochemistry and Molecular Biology-Cell Culture for Biochemists*, Work and Burdon (eds.) Elsevier, Amsterdam. Additional details regarding tissue culture procedures of particular interest in the production of influenza virus in vitro include, e.g., Merten et al. (1996) Production of influenza virus in cell cultures for vaccine preparation. In Cohen and Shafferman (eds) *Novel Strategies in Design and Production of Vaccines*, which is incorporated herein in its entirety. Additionally, variations in such procedures adapted to the present invention are readily determined through routine experimentation.

Cells for production of influenza virus can be cultured in serum-containing or serum free medium. In some case, e.g., for the preparation of purified viruses, it is desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Regardless of the culture volume, in the context of the present invention, the cultures can be maintained at a temperature less than or equal to 35° C., to insure efficient recovery of recombinant and/or reassortant influenza virus, particularly cold-adapted, temperature sensitive, attenuated recombinant and/or reassortant influenza virus. For example, the cells are cultured at a temperature between about 32° C. and 35° C., typically at a temperature between about 32° C. and about 34° C., usually at about 33° C.

Typically, a regulator, e.g., a thermostat, or other device for sensing and maintaining the temperature of the cell culture system is employed to insure that the temperature does not exceed 35° C. during the period of virus replication.

6.7 Recovery of Viruses

Viruses are typically recovered from the culture medium, in which infected (transfected) cells have been grown. Typically crude medium is clarified prior to concentration of influenza viruses. Common methods include filtration, ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Alternatively, the medium is filtered through a 0.8 µm cellulose acetate filter to remove intact cells and other large particulate matter. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus is concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large scale commercial applications, virus is elutriated from density gradients using a zonal-centrifuge rotor operating in continuous mode. Additional details sufficient to guide one of skill through the preparation of influenza viruses from tissue culture are provided, e.g., in Furminger. Vaccine Production, in Nicholson et al. (eds) *Textbook of Influenza* pp. 324-332; Merten et al. (1996) Production of influenza virus in cell cultures for vaccine preparation, in Cohen & Shafferman (eds) *Novel Strategies in Design and Production of Vaccines* pp. 141-151, and U.S. Pat. No. 5,690,937, U.S. publication application nos. 20040265987, 20050266026 and 20050158342, which are incorporated by reference herein. If desired, the recovered viruses can be stored at −80° C. in the presence of sucrose-phosphate-glutamate (SPG) as a stabilizer.

6.8 Influenza Viruses

The genome of influenza viruses is composed of eight segments of linear (−) strand ribonucleic acid (RNA), encoding the immunogenic hemagglutinin (HA) and neuraminidase (NA) proteins, and six internal core polypeptides: the nucleocapsid nucleoprotein (NP); matrix proteins (M); nonstructural proteins (NS); and 3 RNA polymerase (PA, PB1, PB2) proteins. During replication, the genomic viral RNA is transcribed into (+) strand messenger RNA and (−) strand genomic cRNA in the nucleus of the host cell. Each of the eight genomic segments is packaged into ribonucleoprotein complexes that contain, in addition to the RNA, NP and a polymerase complex (PB1, PB2, and PA).

Influenza viruses which may be produced by the processes of the invention in the MDCK cells of the invention include but are not limited to, reassortant viruses that incorporate selected hemagglutinin and/or neuraminidase antigens in the context of an approved attenuated, temperature sensitive master strain. For example, viruses can comprise master strains that are one or more of, e.g., temperature-sensitive (ts), cold-adapted (ca), or an attenuated (att) (e.g., A/Ann Arbor/6/60, B/Ann Arbor/1/66, PR8, B/Leningrad/14/17/55, B/14/5/1, B/USSR/60/69, B/Leningrad/179/86, B/Leningrad/14/55, B/England/2608/76, A/Puerto Rico/8/34 (i.e., PR8), etc. or antigenic variants or derivatives thereof).

6.9 Influenza Virus Vaccines

Historically, influenza virus vaccines have been produced in embryonated hens' eggs using strains of virus selected based on empirical predictions of relevant strains. More recently, reassortant viruses have been produced that incorporate selected hemagglutinin and neuraminidase antigens in the context of an approved attenuated, temperature sensitive master strain. Following culture of the virus through multiple passages in hens' eggs, influenza viruses are recovered and, optionally, inactivated, e.g., using formaldehyde and/or β-propiolactone. However, production of influenza vaccine in this manner has several significant drawbacks. Contaminants remaining from the hens' eggs are highly antigenic, pyrogenic, and frequently result in significant side effects upon administration. More importantly, strains designated for production must be selected and distributed, typically months in advance of the next flu season to allow time for production and inactivation of influenza vaccine. Attempts at producing recombinant and reassortant vaccines in cell culture have been hampered by the inability of any of the strains approved for vaccine production to grow efficiently under standard cell culture conditions.

The present invention provides a vector system, compositions, and methods for producing recombinant and reassortant viruses in culture which make it possible to rapidly produce vaccines corresponding to one or many selected antigenic strains of virus. In particular, conditions and strains are provided that result in efficient production of viruses from a multi plasmid system in cell culture. Optionally, if desired, the viruses can be further amplified in hens' eggs or cell cultures that differ from the cultures used to rescue the virus.

For example, it has not been possible to grow the influenza B master strain B/Ann Arbor/1/66 under standard cell culture conditions, e.g., at 37° C. In the methods of the present invention, multiple plasmids, each incorporating a segment of an influenza virus genome are introduced into suitable cells, and maintained in culture at a temperature less than or equal to 35° C. Typically, the cultures are maintained at between about 32° C. and 35° C., preferably between about 32° C. and about 34° C., e.g., at about 33° C.

Typically, the cultures are maintained in a system, such as a cell culture incubator, under controlled humidity and $CO_2$, at constant temperature using a temperature regulator, such as a thermostat to insure that the temperature does not exceed 35° C.

Reassortant influenza viruses can be readily obtained by introducing a subset of vectors comprising cDNA that encodes genomic segments of a master influenza virus, in combination with complementary segments derived from strains of interest (e.g., antigenic variants of interest). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity. In this context, influenza A strain ca A/Ann Arbor/6/60; influenza B strain ca B/Ann Arbor/1/66; or another strain selected for its desirable phenotypic properties, e.g., an attenuated, cold adapted, and/or temperature sensitive strain, are favorably selected as master donor strains.

In one embodiment, plasmids comprising cDNA encoding the six internal vRNA segments of the influenza master virus strain, (i.e., PB1, PB2, PA, NP, NB, M1, BM2, NS1 and NS2) are transfected into suitable host cells in combination with cDNA encoding hemagglutinin and neuraminidase vRNA segments from an antigenically desirable strain, e.g., a strain predicted to cause significant local or global influenza infection. Following replication of the reassortant virus in cell culture at appropriate temperatures for efficient recovery, e.g., equal to or less than 35° C., such as between about 32° C. and 35° C., for example between about 32° C. and about 34° C., or at about 33° C., reassortant viruses is recovered. Optionally, the recovered virus can be inactivated using a denaturing agent such as formaldehyde or β-propiolactone.

6.10 Methods and Compositions for Prophylactic Administration of Vaccines

Recombinant and reassortant viruses of the invention can be administered prophylactically in an appropriate carrier or excipient to stimulate an immune response specific for one or more strains of influenza virus. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, allantoic fluid from uninfected hens' eggs (i.e., normal allantoic fluid "NAF") or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

Generally, the influenza viruses of the invention are administered in a quantity sufficient to stimulate an immune response specific for one or more strains of influenza virus. Preferably, administration of the influenza viruses elicits a protective immune response. Dosages and methods for eliciting a protective immune response against one or more influenza strains are known to those of skill in the art. For example, inactivated influenza viruses are provided in the range of about 1-1000 $HID_{50}$ (human infectious dose), i.e., about $10^5$-$10^8$ pfu (plaque forming units) per dose administered. Alternatively, about 10-50 μg, e.g., about 15 μg HA is administered without an adjuvant, with smaller doses being administered with an adjuvant. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needleless injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. While stimulation of a protective immune response with a single dose is preferred, additional dosages can be administered, by the same or different route, to achieve the desired prophylactic effect.

Alternatively, an immune response can be stimulated by ex vivo or in vivo targeting of dendritic cells with influenza viruses. For example, proliferating dendritic cells are exposed to viruses in a sufficient amount and for a sufficient period of time to permit capture of the influenza antigens by the dendritic cells. The cells are then transferred into a subject to be vaccinated by standard intravenous transplantation methods.

Optionally, the formulation for prophylactic administration of the influenza viruses, or subunits thereof, also contains one or more adjuvants for enhancing the immune response to the influenza antigens. Suitable adjuvants include: saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvants QS-21 and MF59.

If desired, prophylactic vaccine administration of influenza viruses can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the influenza viruses, or can be administered separately. Either the protein or an expression vector encoding the protein can be administered to produce an immunostimulatory effect.

In another embodiment, the vectors of the invention including influenza genome segments can be employed to introduce heterologous nucleic acids into a host organism or host cell, such as a mammalian cell, e.g., cells derived from a human subject, in combination with a suitable pharmaceutical carrier or excipient as described above. Typically, the heterologous nucleic acid is inserted into a non-essential region of a gene or gene segment, e.g., the M gene of segment 7. The heterologous polynucleotide sequence can encode a polypeptide or peptide, or an RNA such as an antisense RNA or ribozyme. The heterologous nucleic acid is then introduced into a host or host cells by producing recombinant viruses incorporating the heterologous nucleic, and the viruses are administered as described above. In one embodiment, the heterologous polynucleotide sequence is not derived from an influenza virus.

Alternatively, a vector of the invention including a heterologous nucleic acid can be introduced and expressed in a host cells by co-transfecting the vector into a cell infected with an influenza virus. Optionally, the cells are then returned or delivered to the subject, typically to the site from which they were obtained. In some applications, the cells are grafted onto a tissue, organ, or system site (as described above) of interest, using established cell transfer or grafting procedures. For example, stem cells of the hematopoietic lineage, such as bone marrow, cord blood, or peripheral blood derived hematopoietic stem cells can be delivered to a subject using standard delivery or transfusion techniques.

Alternatively, the viruses comprising a heterologous nucleic acid can be delivered to the cells of a subject in vivo. Typically, such methods involve the administration of vector particles to a target cell population (e.g., blood cells, skin cells, liver cells, neural (including brain) cells, kidney cells, uterine cells, muscle cells, intestinal cells, cervical cells, vaginal cells, prostate cells, etc., as well as tumor cells derived from a variety of cells, tissues and/or organs. Administration can be either systemic, e.g., by intravenous administration of viral particles, or by delivering the viral particles directly to a site or sites of interest by a variety of methods, including injection (e.g., using a needle or syringe), needleless vaccine delivery, topical administration, or pushing into a tissue, organ or skin site. For example, the viral vector particles can be delivered by inhalation, orally, intravenously, subcutaneously, subdermally, intradermally, intramuscularly, intraperitoneally, intrathecally, by vaginal or rectal administration, or by placing the viral particles within a cavity or other site of the body, e.g., during surgery.

The above described methods are useful for therapeutically and/or prophylactically treating a disease or disorder by introducing a vector of the invention comprising a heterologous polynucleotide encoding a therapeutically or prophylactically effective polypeptide (or peptide) or RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences as described above in the sections entitled "Expression Vectors" and "Additional Expression Elements." Optionally, more than one heterologous coding sequence is incorporated into a single vector or virus. For example, in addition to a polynucleotide encoding a therapeutically or prophylactically active polypeptide or RNA, the vector can also include additional therapeutic or prophylactic polypeptides, e.g., antigens, co-stimulatory molecules, cytokines, antibodies, etc., and/or markers, and the like.

In one embodiment, the invention provides compositions comprising reassortant and recombinant viruses of the invention (or portions thereof) that have been treated with an agent such as benzonase, to eliminate potential oncogenes. Accordingly, an oncogene-free vaccine composition is specifically included within the embodiments of the invention.

The methods and vectors of the present invention can be used to therapeutically or prophylactically treat a wide variety of disorders, including genetic and acquired disorders, e.g., as vaccines for infectious diseases, due to viruses, bacteria, and the like.

6.11 Kits

To facilitate use of the vectors and vector systems of the invention, any of the vectors, e.g., consensus influenza virus plasmids, variant influenza polypeptide plasmids, influenza polypeptide library plasmids, etc., and additional components, such as, buffer, cells, culture medium, useful for packaging and infection of influenza viruses for experimental or therapeutic purposes, can be packaged in the form of a kit. Typically, the kit contains, in addition to the above components, additional materials which can include, e.g., instructions for performing the methods of the invention, packaging material, and a container.

6.12 Manipulation of Viral Nucleic Acids and Proteins

In the context of the invention, nucleic acids comprising canine RNA pol I regulatory sequences or other nucleic acids of the invention, expression vectors, influenza virus nucleic acids and/or proteins and the like are manipulated according to well known molecular biology techniques. Detailed protocols for numerous such procedures, including amplification, cloning, mutagenesis, transformation, and the like, are described in, e.g., in Ausubel et al. *Current Protocols in Molecular Biology* (supplemented through 2000) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Qβ-replicase amplification, and other RNA polymerase mediated techniques (e.g., NASBA), useful e.g., for amplifying cDNA probes of the invention, are found in Mullis et al. (1987) U.S. Pat. No. 4,683,202; *PCR Protocols A Guide to Methods and Applications* (Innis et al. eds) Academic Press Inc. San Diego, Calif. (1990) ("Innis"); Arnheim and Levinson (1990) *C&EN* 36; *The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomell et al. (1989) *J Clin Chem* 35:1826; Landegren et al. (1988) *Science* 241: 1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563. Additional methods, useful for cloning nucleic acids in the context of the present invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention, e.g., oligonucleotides can be synthesized utilizing various solid-phase strategies including mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3.

In lieu of synthesizing the desired sequences, essentially any nucleic acid can be custom ordered from any of a variety of commercial sources, such as The Midland Certified Reagent Company (mcrc@oligos.com), The Great American Gene Company (www.genco.com), ExpressGen, Inc. (www.expressgen.com), Operon Technologies, Inc. (www.operon.com), and many others.

In addition, substitutions of selected amino acid residues in viral polypeptides can be accomplished by, e.g., site directed mutagenesis. For example, viral polypeptides with amino acid substitutions functionally correlated with desirable phenotypic characteristic, e.g., an attenuated phenotype, cold adaptation, temperature sensitivity, can be produced by introducing specific mutations into a viral nucleic acid segment encoding the polypeptide. Methods for site directed mutagenesis are well known in the art, and described, e.g., in Ausubel, Sambrook, and Berger, supra. Numerous kits for performing site directed mutagenesis are commercially available, e.g., the Chameleon Site Directed Mutagenesis Kit (Stratagene, La Jolla), and can be used according to the manufacturers instructions to introduce, e.g., one or more amino acid substitutions, into a genome segment encoding a influenza A or B polypeptide, respectively.

6.13 Other Viruses

The nucleic acids, vectors, and methods of the present invention can also be used for expression and purification of other recombinant viruses. The following discussion provides guidance for considerations important in adapting the vectors for use with other such viruses.

If the target virus comprises a positive strand, segmented RNA genome, a canine RNA pol I promoter is, preferably, located upstream of the cDNA in the inner transcription unit (unidirectional system). In this embodiment, positive strand RNA is generated for direct incorporation into new viruses. However, embodiments wherein target viruses comprise negative strand, segmented RNA genomes are produced using the unidirectional system are within the scope of the invention.

If the target virus comprises a negative strand, segmented RNA genome, the canine RNA pol I promoter is, preferably, located downstream of the cDNA in the inner transcription unit (bidirectional system). In this embodiment, negative stranded RNA is generated for direct incorporation into new viruses. Embodiments wherein target viruses comprising positive stranded, segmented RNA genomes are produced with the bidirectional system are within the scope of the invention.

The present invention may also be used to produce viruses comprising infectious or noninfectious unsegmented RNA genomes (single stranded or double stranded). In general, simple introduction of infectious viral genomic RNA into a host cell is sufficient to cause initiation of the viral life cycle within the cell and the eventual production of complete viruses. For example, simple introduction of picornaviral genomic RNA into a host cell is sufficient to cause generation of complete picornaviruses. Initiation of the life cycle of a virus comprising uninfectious genomic RNA, typically, requires the additional introduction of other viral proteins which are usually carried within the viral particle along with the genome. For example, parainfluenza virus III carries an RNA dependent RNA polymerase whose presence is required within a newly infected host cell for initiation of viral genomic RNA replication and transcription of viral mRNAs; in the absence of the polymerase, parainfluenza III genomic RNA is not infectious. In embodiments of the present invention wherein viruses comprising infectious, unsegmented genomic RNAs are generated, simple introduction of a dual expression plasmid of the invention, carrying a nucleic acid including the viral genome, into a suitable host cell is sufficient to cause generation of complete viruses. In embodiments wherein viruses comprising uninfectious unsegmented genomic RNA are generated, additional expression plasmids may also have to be introduced into a host cell along with the dual expression plasmid carrying the viral genome. The additional plasmid should express the protein(s) required for initiation of the viral life cycle which are normally introduced into a host cell upon infection (e.g., RNA dependent RNA polymerases).

In embodiments wherein picornavirus, which comprising an infectious, unsegmented RNA genome, is produced, cDNA comprising the complete viral genome is inserted into a dual promoter expression plasmid of the invention. An upstream promoter in an outer transcription unit, preferably, a pol II promoter, directs production of a positive strand mRNA comprising the complete viral genome—a polyprotein is translated from the mRNA and individual proteins are cleaved and liberated from the polyprotein (e.g., by a protease within the polyprotein). Since the viral genome comprises positive strand RNA, a second upstream promoter in an inner transcription unit (unidirectional system), preferably canine RNA pol I, directs production of a positive stranded copy of the genome. If the viral genome comprised negative strand RNA, a second downstream promoter, in an inner transcription unit (bidirectional system), preferably canine RNA pol I, would direct production of a negative stranded copy of the genome. Embodiments wherein negative stranded, unsegmented RNA viruses are produced using the unidirectional system are within the scope of the invention. Similarly, embodiments wherein positive stranded, unsegmented RNA viruses are produced using the bidirectional system are within the scope of the invention.

Viruses comprising uninfectious, unsegmented RNA genomes wherein a polyprotein is not produced can also be generated with the present invention. For example, the present system may be used to produce rhabdoviridae viruses or paramyxoviridae viruses, preferably parainfluenza virus III, whose life cycle normally includes production of multiple monocistronic mRNAs from genomic, negative strand RNA by a virally derived RNA dependent RNA polymerase; individual proteins are expressed from the monocistronic mRNAs. In these embodiments, an outer transcription unit comprising a promoter, preferably a pol II promoter, directs production of a positive strand, polycistronic copy of the viral genome from which, generally, only the first gene (NP) is translated. Additionally, an inner transcription unit comprising a promoter, preferably a canine pol I promoter, directs expression of an RNA copy of the genome for incorporation into new viruses. Since the parainfluenza III viral genome comprises negative stranded RNA, the promoter of the inner transcription unit is preferably located downstream of the cDNA (bidirectional system). If the viral genome comprises positive strand RNA, the promoter of the inner transcription unit is preferably located upstream of the cDNA (unidirectional system). Embodiments wherein viruses comprising a positive stranded RNA genome are produced using the bidirectional system and embodiments wherein viruses comprising a negative stranded RNA genome are produced using the unidirectional system are within the scope of the invention. Additional viral proteins (other than the protein expressed from the polycistronic mRNA) are required for viral transcription and replication (L and P), and these proteins are provided individually on separate expression plasmids.

The invention may also include embodiments wherein viruses comprising double stranded, segmented RNA genomes are generated. In these embodiments, a plasmid comprising each gene in the target viral genome can be inserted into a dual promoter expression plasmid of the invention. The plasmid may be either a unidirectional plasmid or a bidirectional plasmid. A promoter in an outer transcriptional unit, preferably a pol II promoter, directs expression of an mRNA transcript of each gene which is translated into the encoded protein. A promoter in an inner transcription unit, preferably a canine pol I promoter, directs transcription of either a positive strand (unidirectional system) or a negative strand (bidirectional system). Subsequently, the first strand which is produced may act as a template for production of the complementary strand by viral RNA polymerase. The resulting double stranded RNA product is incorporated into new viruses.

7. Specific Embodiments

1. An isolated nucleic acid comprising a canine RNA polymerase I regulatory sequence.

2. The nucleic acid of embodiment 1, wherein the regulatory sequence is a promoter.

3. The nucleic acid of embodiment 1, wherein the regulatory sequence is an enhancer.

4. The nucleic acid of embodiment 1, wherein the regulatory sequence is both an enhancer and a promoter.

5. The nucleic acid of embodiment 1, wherein the RNA polymerase regulatory sequence comprises nucleotides 1 to 1808 of SEQ ID NO:1 or a functionally active fragment thereof.

6. The nucleic acid of embodiment 1, 2, 3, 4, or 5, wherein the regulatory sequence is operably linked to cDNA encoding a negative-strand viral genomic RNA or the corresponding cRNA.

7. The nucleic acid of embodiment 6, wherein the negative-strand viral genomic RNA is an influenza genomic RNA.

8. The nucleic acid of embodiment 6 or 7, wherein the nucleic acid further comprises a transcription termination sequence.

9. An expression vector comprising the nucleic acid of embodiment 1, 2, 3, 4, 5, 6, 7, or 8.

10. The expression vector of embodiment 9, wherein the expression vector comprises a bacterial origin of replication.

11. The expression vector of embodiment 9, wherein the expression vector comprises a selectable marker that can be selected in a prokaryotic cell.

12. The expression vector of embodiment 9, wherein the expression vector comprises a selectable marker that can be selected in a eukaryotic cell.

13. The expression vector of embodiment 9, wherein the expression vector comprises a multiple cloning site.

14. The expression vector of embodiment 13, wherein the multiple cloning site is oriented relative to the canine RNA polymerase I regulatory sequence to allow expression of a coding sequence introduced into the multiple cloning site from the regulatory sequence.

15. A method for producing an influenza genomic RNA, comprising transcribing the nucleic acid of embodiment 7, thereby producing an influenza genomic RNA.

16. A method for producing a recombinant influenza virus, comprising culturing a canine cell comprising the expression vector of embodiment 9, 10, 11, 12 13, or 14 and one or more expression vectors that express an mRNA encoding one or more influenza polypeptide selected from the group consisting of: PB2, PB1, PA, HA, NP, NA, M1, M2, NS1, and NS2; and isolating the recombinant influenza virus.

17. The method of embodiment 16, wherein a helper virus is used.

18. The method of embodiment 16, wherein influenza virus produced is infectious.

19. The method of embodiment 16, 17 or 18, wherein the method results in the production of at least $1\times10^3$ PFU/ml influenza viruses.

20. A cell comprising the nucleic acid of embodiment 1, 2, 3, 4, 5, 6, 7 or 8.

21. A cell comprising the expression vector of embodiment 9, 10, 11, 12, 13 or 14.

22. The cell of embodiment 20 or 21, wherein the cell is a canine cell.

23. The canine cell of embodiment 22, wherein the canine cell is a kidney cell.

24. The canine kidney cell of embodiment 23, wherein the canine kidney cell is an MDCK cell.

25. A method for generating in cultured canine cells a recombinant segmented negative-strand RNA virus having greater than 3 genomic vRNA segments, said method comprising: (a) introducing into a population of canine cells a first set of expression vectors capable of expressing in said cells genomic vRNA segments to provide the complete genomic vRNA segments of said virus; (b) introducing into said cells a second set of expression vectors capable of expressing mRNA encoding one or more polypeptides of said virus; and (c) culturing said cells whereby viral particles are produced.

26. The method of embodiment 25, wherein infectious influenza viral particles are produced.

27. The method of embodiment 25 or 26, wherein helper virus is used.

28. A method for generating in cultured canine cells infectious influenza viral particles, said method comprising: (a) introducing into a population of canine cells a set of expression vectors capable of expressing in said cells i) genomic vRNA segments to provide the complete genomic vRNA segments of said virus and (ii) mRNA encoding one or more polypeptides of said virus; (b) culturing said cells whereby said viral particles are produced.

29. A method of transcribing a vRNA segment of an influenza virus, comprising contacting a canine pol I polymerase polypeptide with a polynucleotide comprising a nucleic acid selected from the group consisting of: SEQ ID Nos: 1-28, wherein said nucleic acid is operably linked to a cDNA molecule encoding said vRNA segment of said negative strand virus; and isolating a transcribed vRNA segment.

30. The method of embodiment 29, wherein the vRNA is transcribed in a host cell.

31. The method of embodiment 16, 17, 18, 19, 25, 26, 27 or 28, wherein each expression vector is on a separate plasmid.

32. A composition comprising a plurality of vectors, wherein the plurality of vectors comprise a vector comprising a canine pol I promoter operably linked to an influenza virus PA cDNA linked to a transcription termination sequence, a vector comprising a canine pol I promoter operably linked to an influenza virus PB1 cDNA linked to a transcription termination sequence, a vector comprising a canine pol I promoter operably linked to an influenza virus PB2 cDNA linked to a transcription termination sequence, a vector comprising a canine pol I promoter operably linked to an influenza virus HA cDNA linked to a transcription termination sequence, a vector comprising a canine pol I promoter operably linked to an influenza virus NP cDNA linked to a transcription termination sequence, a vector comprising a canine pol I promoter operably linked to an influenza virus NA cDNA linked to a transcription termination sequence, a vector comprising a canine pol I promoter operably linked to an influenza virus M cDNA linked to a transcription termination sequence, and a vector comprising a canine pol I promoter operably linked to an influenza virus NS cDNA linked to a transcription termination sequence.

33. The composition of embodiment 32 further comprising one or more expression vectors that express an mRNA encoding one or more influenza polypeptide selected from the group consisting of: PB2, PB1, PA, HA, NP, NA, M1, M2, NS1, and NS2.

34. A host cell comprising the composition of embodiments 32 or 33.

35. A vaccine comprising a virus produced by the method of embodiment 16, 17, 18, 19, 25, 26, 27 or 28.

36. A vaccine comprising an immunogenic composition prepared from a virus produced from the method of embodiment 16, 17, 18, 19, 25, 26 27 or 28.

37. The composition of embodiment 35 or 36, wherein each expression vector is on a separate plasmid.

8. EXAMPLES

The following examples serve merely to illustrate the invention and are not intended to limit the invention in any way.

8.1 Example 1

Growth of Influenza Strains in MDCK Cells

This example describes characterization of several cell lines for culturing influenza. Several different cell lines and primary cells were evaluated for the production of both wild-type (wt) and genetic reassortants derived from laboratory adapted, e.g., cold adapted (ca), influenza strains, type A and type B, including MRC-5, WI-38, FRhL-2, PerC6, 293, NIH 3T3, CEF, CEK, DF-1, Vero, and MDCK. While many of the cell types supported the replication of some cold-adapted influenza strains to a limited extent, only MDCK consistently produced high titers of both type A and type B viruses. For example, PerC6 cells were found to support the replication of certain wt and ca type B viruses to a similar level as that seen in MDCK cells although the growth kinetics are different (see FIG. 1). In contrast, PerC6 was unable to support the replication of a number of ca type A viruses. FIG. 2 shows the growth curves for wt and ca A/Sydney/05/97 and A/Beijing/262/95 viruses. In both cases the ca strain does not replicate well in PerC6 cells. Likewise, FIG. 3 shows the growth curves for wt and ca A/Ann Arbor/6/60 demonstrating that the ca strain does not replicate efficiently in PerC6 cells and the replication of wt A/Ann Arbor/6/60 is not as robust as in MDCK cells. Real time PCR analysis of influenza virus replication in PerC6 cells showed that viral RNA (VRNA) of both the ca and wt A influenza virus strains increased during the first 24 hours post infection however only the wt strains continued to increase out to 120 hours, the ca strains did not. In contrast, both wt and ca vRNA increased and reached plateau at day 3 in MDCK cells. See FIG. 4.

The MDCK cells were also tested for their ability to support replication of a potential pandemic vaccine, ca A/Vietnam/1203/2004. MDCK cells were infected at a low multiplicity of infection with ca A/Vietnam/1203/2004 and virus in the supernatant was quantified at various times post infection. By 48 hours post infection, the titers of ca A/Vietnam/1203/2004 reached approximately 8 $\log_{10}$ $TCID_{50}$/mL and remained stable for the next 3 to 4 days. See FIG. 5.

In the experiments, MDCK cells obtained from the ATCC (Accession No. CCL-34) were expanded a limited number of times in either media containing 10% fetal bovine serum sourced from the United States or in an appropriate serum free media (e.g., SFMV 100) to produce pre-master cell stocks for initial characterization studies. Appropriate serum-free media are described in U.S. Provisional Application No. 60/638,166, filed Dec. 23, 2004; U.S. Provisional Application No. 60/641,139, filed Jan. 5, 2005; and U.S. application Ser. No. 11/304,589 filed Dec. 16, 2005, each of which is hereby incorporated by reference in its entirety. Cells were readily grown in both types of media and both stocks of cells supported the replication of cold-adapted vaccine strains and pandemic strains as shown in Table 1, below, and in FIG. 5, respectively.

TABLE 1

Comparison of productivity of cold-adapted influenza strains in serum and serum free grown MDCK cells.

| Virus strain (6:2 reassortant) | $TCID_{50}$/mL ($\log_{10}$) | |
|---|---|---|
| | MDCK with serum | MDCK w/out serum |
| A/New Caledonia/20/99 (H1N1) | 8.1 | 7.8 |
| A/Panama/20/99 (H3N2) | 6.8 | 6.4 |
| A/Sydney/05/97 (H3N2) | 7.0 | 6.5 |
| B/Brisbane/32/2002 | 7.2 | 7.5 |

TABLE 1-continued

Comparison of productivity of cold-adapted influenza strains in serum and serum free grown MDCK cells.

| Virus strain (6:2 reassortant) | $TCID_{50}$/mL ($\log_{10}$) | |
|---|---|---|
| | MDCK with serum | MDCK w/out serum |
| B/Hong Kong/330/2001 | 7.2 | 7.4 |
| B/Victoria/504/2000 | 6.9 | 7.5 |

To investigate the gene segments responsible for the restricted growth in PerC6 cells the eight-plasmid rescue technique was employed to generate a 7:1 reassortant for each gene segment of the influenza A/AA/6/60 strain. See, e.g., U.S. Pat. No. 6,951,754 for a representative description of the eight-plasmid influenza rescue system. FIG. 6 shows a schematic diagram and the naming strategy for each 7:1 reassortant. The resulting reassortants were then assayed for their ability to replicate in PerC6 cells. See FIG. 7. The growth restriction phenotype appears to map to the PB2 and PB1 gene segments. Fine detail mapping of the exact location responsible for this phenotype can be performed using methods well know in the art. For example, sequence comparison of wt and ca strains in the identified gene segments will allow for the identification of specific differences which can then be back mutated in either a wt or ca strain. Such mutants are then analyzed for their ability to grow in PerC6 cells. Any mutation that either prevents growth of a wt strain or allows growth of a ca strain is identified as one that contributes to the growth restriction phenotype.

8.2 Example 2

Tumorigenicity of MDCK Cell Lines

The potential tumorigenicity of the two pre-master cell stocks of MDCK cells, one grown in media containing serum and the other in serum free media, were evaluated in the athymic nude mouse model at a stage that would represent 5 cell passages after that expected to be used for vaccine production. To evaluate tumorigenicity, $10^7$ cells were injected subcutaneously into groups of 10 mice and after 84 days the animals were sacrificed and examined. Neoplasias were observed in six of the 10 animals inoculated with the cells passaged in serum free media. In contrast, there was no evidence of neoplasia in any of the animals inoculated with cells passaged in media supplemented with 10% fetal bovine serum; although some fibrosarcomas were observed at the site of inoculation, cells passaged in serum were not tumorigenic as shown in Table 2.

TABLE 2

Tumorigenicity and Karyology of MDCK cells passed in two different media

| | Serum free | | 10% Serum | |
|---|---|---|---|---|
| | Passage 4 | Passage 20 | Passage 4 | Passage 20 |
| Tumorigenicity | ND | Neoplasias noted | ND | No neoplasias. Fibrosarcomas at injection site |
| Estimated $TP_{50}$* (no animals with tumors/total animals) | ND | ~$10^7$ (6/10) | ND | Not estimable (>$10^7$) (0/10) |

TABLE 2-continued

Tumorigenicity and Karyology of MDCK cells passed in two different media

| | Serum free | | 10% Serum | |
| --- | --- | --- | --- | --- |
| | Passage 4 | Passage 20 | Passage 4 | Passage 20 |
| Karyology Median number; comments | 78; Large distribution of cells with chromosome number of 52 to 82 | 78; Large distribution of cells with chromosome number of 52-82 | 78; Few cells with anomalous chromosome number (70 to 82) | 78; Few cells with anomalous chromosome number (70 to 82) |

*$TP_{50}$: Number of cells required to induce tumors in 50% of animals
ND: Not done As shown in Table 2, karyotype analyses were also performed on these two premaster cell stocks at both the fourth and twentieth passage in their respective media. The non-tumorigenic cells passaged in 10% FCS had a median number of 78 metaphase chromosomes with relatively limited distribution of cells with other chromosome numbers (70 to 82). While the cells passaged in serum free media also had a median number of 78 metaphase chromosomes, significantly more cells were observed with an aneuploid chromosome number ranging from 52 to 82 metaphase chromosomes. In both cases, the karyology did not change following passage.

8.3 Example 3

Adapting MDCK Cells to Grow in Serum Free Media

MDCK cells from the ATCC are passaged in media containing gamma irradiated FBS. These cells are then passaged a limited number of times in a serum free media formulation chosen to support cell bank production. Serum free media are described in U.S. Provisional Application Nos. 60/638,166 and 60/641,139, and U.S. patent application Ser. No. 11/304,589. These additional passages may be performed at either 37° C. or 33° C. Passage of MDCK cells in three media containing plant-derived supplements rather than serum yielded cells with karyotypes similar to that of MDCK cells passaged in FCS containing media (data not shown).

8.4 Example 4

Cloning of MDCK Cells

Cells were biologically cloned through limiting dilution in order to ensure that the production cells are derived from a unique genetic constellation. Clones were screened for various phenotypic properties including doubling time and relative tumorigenicity, as well as viral production. In an initial proof of concept experiment, fifty-four MDCK clones were obtained in media containing FCS. These clones were passaged and each was infected with a low multiplicity of infection of ca A/New Caledonia/20/99. Several days after infection, the supernatant was removed and the quantity of virus in the supernatant was measured by $TCID_{50}$. A minority of the clones produced relatively high titers of virus, greater than was produced in the non-cloned parental cells. Clones with superior biological and physiological properties are used to establish a Master Cell Bank (MCB) as described below.

8.5 Example 5

Testing and Characterization of a Master Cell Bank

The MCB is extensively tested to ensure that there is no evidence of adventitious agents. For example, one or more of several PCR and/or antibody-specific tests for available viral agents are conducted, as shown in Table 3, below.

TABLE 3

Testing regimen for the MCB

| General tests | PCR*/Ab specific |
| --- | --- |
| Sterility | AAV Types 1&2 |
| Mycoplasma | HCMV |
| Adventitious agents in vitro (multiple cell lines) | EBV |
| Adventitious agents in vivo | HSV |
| PERT | Hepatitis B, C & E |
| Co-cultivation | HHV 6, 7 & 8 |
| Karyology | HIV 1&2 |
| Electron microscopy | HPV |
| Tumorigenicity intact cells ($TP_{50}$) | HTLV I & II |
| Oncogenicity of cellular DNA | Polyoma (BK and JC viruses) |
| Oncogenicity of cellular lysate | Circovirus |
| Bovine viruses per 9CFR | Canine Parvovirus |
| Porcine viruses per 9CFR | Canine distemper Adenovirus SV40 |

8.6 Example 6

Preclinical Characterization of Cell Culture-Derived Influenza Virus

This example describes characterization of influenza strains produced from cell culture as well as from eggs and compares the viruses produced from the systems. Generally, the influenza viruses are suitable for use as vaccines in humans, and have biological properties that make the viruses suitable for such use. In this example, the influenza viruses are cold-adapted (ca; have the ability to replicate efficiently at lower temperatures), temperature sensitive (ts; have restricted replication in vitro at higher temperatures), and attenuated (att; no detectable replication in lung tissues of ferrets), and are referred to herein as catsatt strains. The comparison includes: biochemical, antigenic, and genetic evaluation (sequencing) of viral product; biological and biochemical characterization of the virus following replication in human cells; replication in a permissive animal model; and immunogenicity in a permissive animal model.

8.6.1 Genetic, Biochemical and Antigenic Comparability

Ca ts att strains of type A/H1N1, A/H5N1, A/H3N2 and B replicated to relatively high titers in MDCK cells. In addition, passaging these ca ts att strains in MDCK cells did not alter their genomic sequence. Three ca ts att strains, ca A/Sydney/05/97, ca A/Beijing/262/95, and ca B/Ann Arbor/1/94 were passaged once or twice in MDCK cells and the entire coding regions of all 6 internal genes were sequenced and compared to the starting material. No nucleotide changes were observed, demonstrating that this passaging through this substrate did not change the genetic composition of these strains. Further sequence characterizations is performed on different vaccine strains produced in MDCK cells under conditions that are expected to mimic the production process including media composition, input dose (moi), temperature of incubation and time of harvest. Based on the preliminary data, it is expected that there will be no changes in the genomic sequence of MDCK-produced virus.

Because the genome was genetically stable following passage in MDCK cell, the biological traits of the vaccine produced in eggs or MDCK cells are expected to be indistinguishable. However, the primary viral product from cell culture may have some subtle differences compared to the egg based product, particularly with respect to post-translational modification of viral proteins including HA and NA, or composition of lipids in the viral membrane; both of which could potentially change the overall physical properties of the virion. Preliminary preclinical data on the antigenicity of cell culture produced and egg produced vaccine demonstrated that there were no detectable differences in this important parameter. Egg stocks of several vaccine strains were passaged through MDCK cells and the antigenicity of both products was determined by measuring the HAI titers using reference antisera. As show in Table 4, all the HAI titers were within 2-fold of one another, indicating that replication of the vaccine in cells did not change the antigenicity of the vaccine compared to egg derived material.

TABLE 4

HAI Titers of strains produced in eggs and MDCK cells

| Strain | HAI Titer | |
|---|---|---|
| | Egg derived | MDCK derived |
| A/Panama/20/99 | 256 | 256 |
| A/Wuhan/359/95 | 1024 | 2048 |
| A/Wyoming/03/2003 | 512 | 1024 |
| B/Jilin/20/2003 | 64 | 32 |
| B/Hong Kong/330/01 | 64 | 64 |
| B/Jiangsu/10/2003 | 128 | 128 |

8.7 Example 7

Infection of Human Epithelial Cells in Culture

In one embodiment, to evaluate the biochemical, biological, and structural similarities following replication of the MDCK and egg produced vaccines in cells of human origin, vaccines may be passaged once in relevant diploid human cells, such as normal human bronchial epithelial cells (NHBE). This passage will serve to mimic a single infection event in the human airway and then enable comparison of the progeny virus, the virus that is ultimately responsible for eliciting an effective immune response. Studies of the vaccines' hemagglutinin (binding and fusion) and neuraminidase activities can be measured on these materials as well as other biochemical and structural studies including electron microscopy, infectious to total particle ratios, and viral genome equivalents can be evaluated. Overall, these comparisons will serve to demonstrate the comparability of the cell-derived vaccine to the effective and safe egg produced vaccine. A summary of analytical studies is summarized in Table 5.

TABLE 5

Preclinical studies to compare cell and egg produced vaccines

| In vivo (ferrets) | In vitro* |
|---|---|
| Attenuation/Replication | Virus binding |
| Extent of replication in upper airway | Hemagglutination titer |
| Kinetics of replication in upper airway | Binding of different sialic acids |
| Immunogenicity | Physical properties |
| Cross-reactivity | Morphology by EM |
| Kinetics | Infectious: Total particles (genomes) |
| Infectivity | Fusion activity |
| Dose required for detectable replication | pH optimum |
| Dose required for antibody response | temperature optimum |
| | Genomic sequence |
| | Neuraminidase activity |

*Compare primary products and after one passage in human cells 8.8 Example 8

Preclinical Animal Models

The ferret is a robust animal model used to evaluate the attenuation and immunogenicity of attenuated influenza vaccines and component vaccine strains. The performance of cell-derived influenza strains produced from the MCB are compared to the same strains produced in eggs. Head to head comparison of these materials in controlled studies enables a high level of assurance of the comparability of these viral products.

In order to evaluate the ability of the two vaccines to infect or achieve a "take" in the ferret, animals are lightly anesthetized and inoculated intranasally with either the cell or egg produced viral preparations. Nasal wash material is collected at several time points following inoculation and the quantity of virus is evaluated by one of several available methods in order to evaluate the kinetics and extent of viral replication in the animals' upper respiratory tract. Experiments are performed with a range of doses and include multiple strains and different trivalent mixtures to generalize the relative infectivity of cell culture grown strains to egg produced strains. These same studies are also used to evaluate the immunogenicity of the influenza strains, a property that is inherently linked to the ability of the virus to initiate infection. Animals are bled and nasal washes are harvested at various points (weeks) post inoculation; these specimens are used to assess the serum antibody and nasal IgA responses to infection. The culmination of these data, infectivity, serum antibody and mucosal antibody responses, will be used to compare and evaluate the relative infectivity of the cell-produced vaccine to the egg produced vaccine. The most likely outcome is predicted to be that the cell and egg produced vaccine strains have similar infectivity and immunogenicity. If the cell derived vaccine appeared to be more infective or more immunogenic than the egg-derived product, further studies evaluating the possibility of lower dosage are performed.

A number of immunogenicity and replication studies are performed in the ferret model to evaluate the cell culture-derived vaccines with a single unit human dose. Infection with ca ts att strains generally elicits strong and rapid antibody responses in ferrets. In addition, individual ca ts att strains are routinely tested and shown to express the attenuated (att) phenotype by replicating to relatively high titers in the nasopharynx but to undetectable levels in the lung of these animals. The impact of cell culture growth on these biological traits is also assessed. However, it is unlikely that any differences will be seen, since the att phenotype is an integral part of the genetic composition of these strains. The growth kinetics and crossreactivity of these strains is evaluated following administration of a single human dose in these animals. This elicits serum antibodies that cross-react with multiple strains within a genetic lineage; and it is expected that a cell-derived vaccine will have the same capability.

These comparability evaluations should provide significant insight into potential biochemical and/or biophysical differences of the primary virus product and demonstrate the impact of these epigenetic differences on the performance of the ca ts att strains measured by first passaging the virus in human cells or animal studies. Based on the sequence information to date, there is no expected impact on the ca ts att strains immunogenic performance resulting from production on MDCK cells.

Ferrets are a well document animal model for influenza and are used routinely to evaluate the attenuation phenotype and immunogenicity of ca ts att strains. In general, 8-10 week old animals are used to assess attenuation; typically study designs evaluate n=3-5 animals per test or control group. Immunogenicity studies are evaluated in animals from 8 weeks to 6 months of age and generally require n=3-5 animals per test article or control group. These numbers provide sufficient information to obtain statistically valid or observationally important comparisons between groups. During most studies Influenza-like signs may be noticed, but are not likely. Ferrets do not display signs of decrease in appetite or weight, nasal or ocular discharge; observing signs of influenza-like illness is a necessary part of the study and interventions such as analgesics are not warranted. Other signs of discomfort, such as open sores or significant weight loss, would result in appropriate disposition of the animal following discussion with the attending veterinarian.

8.9 Example 9

Master Virus Seed (MVS) Development

Currently influenza vaccine strains are generated by co-infecting avian cells with a wild type virus and either the type A or type B MDV and isolating and screening the progeny for the desired 6:2 genetic constellation. This process requires several passages of the virus through avian cell cultures and/or SPF eggs. Recently, plasmid rescue has been introduced for producing influenza viral preparation. In this process, Vero (African green monkey) cells from an extensively tested and characterized cell bank are electroporated with, e.g., 8 DNA plasmids, each containing a cDNA copy of one of the 8 influenza RNA segments. Several days after electroporation the supernatant of these electroporated cells contains influenza virus. The supernatants are then inoculated into SPF eggs to amplify and biologically clone the vaccine strain. Both of these procedures result in a vaccine strain that is inoculated into SPF eggs to produce the MVS. While plasmid rescue has several advantages including more reliable timing, more genetically accurate gene segments and less potential contamination with adventitious agents from the wild type isolate, individual MVS's generated by these two methods are indistinguishable from one another and can be used to initiate bulk vaccine production. Using the methods and composition of the invention, this method is adapted to use MDCK cells instead of the Vero cells for plasmid rescue.

Final amplification of the vaccine strains is conducted in cells derived from the MDCK cell banks. This final amplification can be achievable with small-scale cultures (<20L) of MDCK cells. The supernatant from these cells is collected, concentrated and characterized/tested to produce the MVS.

8.10 Example 10

Cloning of Canine RNA Pol I Regulatory Sequences

This example describes cloning of the canine 18S ribosomal RNA gene and the nucleic acid sequences 5' to this gene.

First, genomic DNA from MDCK cells (Accession No. CCL-34, ATCC) was isolated using a MasterPure DNA Purification kit (EPICENTRE Biotechnologies; Madison, Wis.). Sequence alignment indicates that 18S rRNA gene is about 90% identical in dog, human, mouse, rat, and chicken. A pair of primers were designed based on the sequences in the conserved region near the 5' end of 18S rRNA gene for PCR to amplify a ~500 bp region from MDCK genomic DNA as a probe to detect the digestion fragments on the membrane which has complementary sequences through Southern hybridization. A single restriction fragment was identified in genomic DNA digested separately with BamH I (~2.2 kb) and EcoR I (~7.4 kb). Both fragments were cloned into the pGEM 7 vector (Promega Corp.; Madison, Wis.) for further analysis. The plasmid containing the EcoR I fragment was submitted for deposit with the American Type Culture Collection on Apr. 19, 2006, and was assigned A.T.C.C. Accession No. PTA-7540 and the deposit date of Apr. 20, 2006.

The two clones obtained by restriction digestion analysis were aligned and the orientation of the two clones was confirmed by sequencing both ends of the two clones. A restriction map of the Eco RI fragment is presented as FIG. 8. Next, the complete nucleic acid sequences of the fragment between the 5' EcoR I site and the next BamH I site in the 3' direction was determined and assembled into a nucleotide sequence containing about 3536 bases. This sequence is presented as FIGS. 9A-C (SEQ ID NO:1).

Next, primer extension experiments were performed to identify the initial nucleotide of transcripts expressed from the canine RNA pol I regulatory elements. Briefly, total RNA was isolated from MDCK cells. A labeled oligonucleotide primer was annealed to the RNA and used to prime DNA synthesis towards the 5' end of the 18s rRNA. To identify the first nucleotide in the transcript, the same primer was used to sequence the rRNA using a conventional dideoxynucleotide-based protocol By comparing the length of the nucleic acid obtained in the primer extension to the various nucleic acids obtained in the sequencing reaction, the first base of the 18s rRNA could be identified. The first transcribed nucleotide (the +1 position) is at base 1809 of the nucleotide sequence presented as FIGS. 9A-C.

To confirm that the sequences upstream from this nucleotide contain sufficient regulatory elements to direct transcription of downstream genes, a construct comprising an EGFP gene under control of the regulatory sequences was constructed using standard techniques. The EGFP gene used in this construct is the EGFP gene described in Hoffmann et al. (2000) "Ambisense" approach for the generation of influenza A virus: vRNA and mRNA synthesis from one template *Virology* 15:267(2):310-7). This construct was then was transfected into MDCK cells using conventional techniques. 24 hours following transfection, RNA was isolated from the transfected cells and subjected to Northern blot analysis with a labeled DNA encoding an EGFP gene. Detection of appropriately sized transcripts confirmed that the plasmids transfected into the MDCK cells contained regulatory sequences that directed transcription of the sequences 3' to the regulatory elements.

8.11 Example 11

Identification of Canine RNA Polymerase I Regulatory Elements

This example describes identification and characterization of a canine RNA polymerase I regulatory element, the canine RNA polymerase I promoter.

Canine RNA pol I promoters and other regulatory regions are identified by inspecting sequences 5' to the initiation of transcription of the 18s rRNA for canonical promoter sequences. Further, simple deletion experiments are performed to identify the sequences required for efficient transcriptional initiation. In one such deletion experiment, a restriction site is introduced into or identified in a plasmid encoding the nucleotide sequence of FIGS. 9A-C by site directed mutagenesis. The restriction site is introduced about 50 nucleotides 3' from the +1 nucleotide identified above, nucleotide 1809 in the sequence presented as FIGS. 9A-C. Another restriction site 5' to the nucleotide sequence of FIGS. 9A-C relative to the +1 position is identified or introduced by site-directed mutagenesis.

The vectors containing these restriction sites are then linearized by digestion with the appropriate restriction enzyme. Next, an appropriate nuclease (e.g., Exonuclease I, Exonuclease III, and the like) is used to digest the linear nucleic acids. By stopping the reaction at different time points, different sizes of deletions in the regions 5' to the start of transcription can be obtained. Next, the linear plasmids are recircularized and transformed into appropriate host cells, then screened to identify plasmids containing the desired deletions. Alternately, appropriate oligonucleotides can be synthesized that contain sequences flanking a deletion to be introduced. Such oligonucleotides are then used to make derivatives containing loop-out deletions using standard techniques. Oligonucleotides can also be used to make site-directed substitutions using standard techniques.

The ability of the different deletion or substitution mutants to initiate transcription is determined by transfecting the plasmids into MDCK cells and detecting RNA transcribed from the plasmids by Northern Blot as described above. By comparing the sequences of plasmids that allow transcription with those that do not allow transcription, the sequence of the canine RNA polymerase I promoter is identified. Conventional techniques are then used to clone a nucleic acid encoding this sequence.

Alternately, the canine RNA pol I promoter can be mapped from the nucleic acid provided as SEQ ID NO:1 by other methods known in the art, e.g., by using a minigenome approach. See, e.g., published U.S. application 20050266026 for use of an influenza minigenome reporter designated pFlu-CAT, which contained the negative sense CAT gene cloned under the control of the pol I promoter. Also see, EGFP minigenome in Hoffmann et al. (2000) "Ambisense" approach for the generation of influenza A virus: vRNA and mRNA synthesis from one template *Virology* 15:267(2):310-7); and CAT minigenome system pPOLI-CAT-RT in Pleschka et al. (1996) J. Virol. 70(6):4188-4192.

To use these systems to identify and characterize the sequences required for efficient transcriptional initiation, the different deletion/substitution mutants described above or other subsequences of SEQ ID NO:1 are introduced into the reporter plasmid selected (e.g., PFlu-CAT, the EGFP minigenome) such that transcription of a negative-sense copy of the reporter gene depends on initiation of transcription by the deletion or substitution mutant. The EGFP-containing construct described above can conveniently be used to make such deletion or substitution mutants. Next, viral RNA-dependent RNA polymerase synthesizes positive-strand mRNA from the negative-strand RNA transcribed from the reporter plasmid. This positive-strand mRNA is then translated by the cellular machinery so that the reporter protein (either EGFP or CAT) activity can be detected.

In the assays, a set of expression plasmids that contains the cDNAs of PB1, PB2, PA and NP or PB1, PA, NP (−PB2 as a negative control) is transfected into MDCK cells together with a plasmid comprising an influenza A virus EGFP minigenome or the pFlu-CAT reporter under the control of a putative canine Pol I regulatory sequence. The cells are then cultured under conditions that permit transcription and translation of the reporter sequence.

Activity of the reporter protein is detected using conventional techniques. In the case of EGFP, the transfected cells are observed under phase contrast microscope or fluorescence microscope at 48 hours post-transfection. Alternatively, flow cytometry is employed to detect EGFP expression. In assays with a minigenome comprising the CAT gene, designated pFlu-CAT is utilized to measure polymerase activity. In such an assay, CAT expression is measured by detecting the CAT protein directly (e.g., by ELISA), by detecting mRNA encoding CAT (e.g., by Northern blot), or by detecting CAT activity (e.g., detecting transfer of radiolabeled acetyl groups to an appropriate substrate) as an indicator of reporter activity.

For example, the DNA fragments from the MDCK clone which had exhibited promoter activity (see primer extension and transcription assays above) were cloned upstream of an insert which contained influenza 5' and 3' untranslated regions fused to the 5' and 3' ends, respectively, of a negative sense EGFP gene followed by a murine Pol I terminator (See, FIG. 11). Three separate constructs were made which differed in the inserted MDCK sequences: MDCK sequences 1-1807 (−1), 1-1808 (+1) and 1-1809 (+2) of SEQ ID NO:1. Each of these constructs were separately combined with expression plasmids for influenza replication proteins (PB1, PB2, PA and NP) and electroporated into MDCK cells. At 24 hours post-electroporation, the cells were examined by fluorescence microscopy. As shown in FIG. 12, all three MDCK fragments, −1, +1 and +2 (top left, middle and right, respectively) resulted in EGFP fluorescence while the construct lacking promoter activity exhibited only background fluorescence (bottom left). The 1-1808 (+1) fragment resulted in the highest level of fluorescence. A plasmid with a CMV promoter driving expression of EGFP is used as a positive control (bottom right).

Influenza replication proteins will only replicate authentic influenza vRNA ends. The EGFP signal from each of the plasmids containing an MDCK pol I sequence indicates that the canine regulatory sequence fragments contained promoter activity which produced a RNA with correct influenza vRNA ends capable of supporting influenza replication.

Other assays useful for identifying and characterizing the canine RNA pol I regulatory sequences include RNA footprinting experiments. In such procedures, RNA molecules comprising, e.g., the sequence presented in FIGS. 9A-C, are contacted to one or more subunits of canine RNA polymerase I. The one or more subunits of canine RNA pol I bind to appropriate RNA sequences according to their particular affinities. Next, an RNAse, e.g., RNAse I, is used to degrade RNA unprotected by the one or more subunits of canine RNA polymerase. The RNAse is then inactivated and the protected RNA fragments isolated from the protecting one or more subunits of RNA polymerase 1. The isolated fragments contain sequences bound by the one or more subunits of RNA polymerase I and are excellent candidates for sequences having promoter/enhancer activity. Further, these foot-printing experiments can be performed in the presence of different subunits of canine RNA polymerase I to identify which subunit binds which RNA sequence. These experiments can help to determine the activity of the different bound sequences by, e.g., comparing the sequences of the different canine Pol I polymerase subunits to RNA polymerase I subunits from other species with known sequences and binding specificities.

In vitro techniques can also be used to monitor transcription from putative canine pol I regulatory sequences. In these techniques, the different deletion/substitution mutants described above or other subsequences of SEQ ID NO:1 or 26 are operably linked to a transcript of interest. The set of canine RNA polymerase I proteins required for transcription are then added to the transcripts. Effective transcription is detected by detecting the RNA transcript made by the canine RNA polymerase I proteins by, e.g., Northern blotting.

Similar assays can be used to identify other canine RNA pol I regulatory elements, e.g., enhancer, repressor, or other elements that affect transcription by RNA pol I. Generally, in such assays, expression levels from reporter constructs comprising deletions, substitutions, or subsequences of SEQ ID NO.: 1 are compared to expression levels from a minimal RNA pol I promoter identified as described above. By comparing the expression levels, the presence of an element associated with enhanced or decreased transcription can be identified.

8.12 Example 12

Influenza Rescue in MDCK Cells

This example describes use canine RNA pol 1 regulatory elements cloned in Example 10 to rescue influenza virus in MDCK cell culture.

Eight expression vectors encoding viral genomic RNAs under the control of the canine RNA pol I promoter were constructed using conventional molecular biology techniques. In particular, the plasmid expression vector pAD4000 (SEQ ID NO:29, FIG. 13) was constructed from a pAD3000 vector (Hoffman et al. PNAS (2002), 99(17): 11411-11416, FIG. 10) by replacing the 213 bp human Pol I promoter sequences in pAD3000 with a 469 bp fragment (bases 1-469 in pAD4000) from the MDCK EcoRI-BamHI subclone (bases 1808-1340 of SEQ ID NO:1). Note: the 469 bp fragment in FIG. 13 is shown as bases 1-469, but in reverse complement orientation. The 469 bp MDCK fragment contains a functional canine Pol l promoter. In addition, the 18 bp linker sequence in pAD3000 AGGAGACGGTACCGTCTC (SEQ ID NO:30) was replaced with the 24 bp linker sequence AGAGTCTTCTCGAGTAGAAGACCG (SEQ ID NO:31) in pAD4000.

Eight influenza segments encoding the MDV B genome, two of which (the NS, SEQ ID NO: 32 and PB1, SEQ ID NO: 40) contained silent mutations (SEQ ID NOS: 33 and 41, respectively, and FIG. 16) were cloned into eight separate pAD4000 expression vectors (under the control of a functional canine Pol I promoter). The eight expression vectors were then electroporated into MDCK cells in serum free Opti-MEM® I media (Invitrogen) and supernatants from the cells were used to inoculate eggs. After 72 hrs incubation at 33° C. virus was harvested from HA positive eggs. RT-PCR reactions were performed (see, primer sequences (SEQ ID NOS: 34-39) and annealing positions in FIGS. 14 and 15) on RNA extracted from the virus followed by nucleotide sequence analysis of the PCR products. Based on the presence of PB1 and NS segments containing the silent mutations, it was determined that live infectious influenza virus had been rescued in MDCK cells.

Surprisingly high titers of rescued viruses (both of MDV-B and MDV-Bm [MDV-B with silent mutations]) were found in the supernatants. See, Table 6. For instance, 4-5 $\log_{10}$ PFU/ml of virus was measured at day 3. Typically, titers of viruses rescued using human polI promoter systems based on Vero cells are only <=100 pfu at days 2 to 3. Accordingly, the canine polI plasmid rescue system described herein appears to much more efficient that existing plasmid rescue technology described by others.

TABLE 6

| | HAI Titer PFU/mL | |
|---|---|---|
| | MDV-B | MDV-Bm |
| Day 2 | 1.48E+03 | 2.22E+02 |
| Day 3 | 6.60E+05 | 9.80E+04 |
| Day 4 | 2.28E+07 | 5.20E+06 |
| Day 5 | 1.90E+07 | 1.80E+07 |
| Day 6 | 3.60E+06 | 3.20E+06 |
| Day 7 | 2.62E+06 | 2.96E+06 |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method for producing a recombinant influenza virus, comprising:
   i) introducing expression vectors into a population of canine cells wherein said expression vectors are
      a. capable of expressing in said cells genomic vRNA segments to provide the complete genomic vRNA segments of said virus, wherein one or more of said expression vectors comprise nucleotides 1-469 of SEQ ID NO:26, or a functionally active fragment thereof, wherein said fragment is capable of directing the expression of influenza vRNA, and
      b. also capable of expressing in said cells one or more mRNA encoding an influenza polypeptide selected from the group consisting of: PB2, PB1, PA, HA, NP, NA, M1, M2, NS1, and NS2; and
   ii) culturing said cells whereby influenza viral particles are produced.

2. The method of claim 1, wherein the titer of the influenza viral particles produced upon culturing said cells for 48-72 hours is at least $1.0 \times 10^4$ PFU/ml.

3. The method of claim 1, wherein the titer of the influenza viral particles produced upon culturing said cells for 48-72 hours is at least $1.0 \times 10^5$ PFU/ml.

4. The method of claim 1, wherein the canine cells are kidney cells.

5. The method of claim 1, wherein the canine cells are MDCK cells.

6. The method of claim 1, wherein the recombinant influenza virus is a reassortant virus.

7. The method of claim 1, wherein influenza viral particles produced are infectious.

8. The method of claim 1 or 6, wherein the one or more mRNA encode the HA and/or the NA from a pathogenic influenza strain.

9. The method of claim 8, wherein the one or more mRNA additionally encode the PB2, PB1, PA, NP, M1, M2, NS1, and/or NS2 from an attenuated influenza strain.

10. The method of claim 9, wherein the attenuated influenza strain is selected from the group consisting of A/Ann Arbor/6/60, B/Ann Arbor/1/66, and A/Puerto Rico/8/34.

11. The method of claim 1 or 6, wherein the recombinant virus is selected from the group consisting of a cold-adapted influenza virus, an attenuated influenza virus, a temperature sensitive influenza virus, and an attenuated, temperature sensitive, cold-adapted influenza virus.

* * * * *